United States Patent
Brinkmann et al.

(10) Patent No.: US 12,312,386 B2
(45) Date of Patent: May 27, 2025

(54) TARGETED INTRACELLULAR DELIVERY OF LARGE NUCLEIC ACIDS

(71) Applicant: Hoffmann-La Roche Inc., Little Falls, NJ (US)

(72) Inventors: Ulrich Brinkmann, Weilheim (DE); Tobias Killian, Penzberg (DE)

(73) Assignee: Hoffmann-La Roche Inc., Little Fall, NJ (US)

( * ) Notice: Subject to any disclaimer, the term of this patent is extended or adjusted under 35 U.S.C. 154(b) by 1034 days.

(21) Appl. No.: 16/950,646

(22) Filed: Nov. 17, 2020

(65) Prior Publication Data

US 2021/0061867 A1  Mar. 4, 2021

Related U.S. Application Data

(63) Continuation of application No. PCT/EP2019/062417, filed on May 15, 2019.

(30) Foreign Application Priority Data

May 18, 2018 (EP) .................................... 18173087
Oct. 15, 2018 (EP) .................................... 18200414

(51) Int. Cl.
*C12N 15/80* (2006.01)
*C07K 14/47* (2006.01)
*C07K 16/44* (2006.01)
*C12N 15/113* (2010.01)

(52) U.S. Cl.
CPC .............. *C07K 14/47* (2013.01); *C07K 16/44* (2013.01); *C12N 15/113* (2013.01); *C07K 2317/31* (2013.01); *C12N 2310/20* (2017.05)

(58) Field of Classification Search
CPC .... C12N 15/79; C12N 2310/20; C12N 15/87; A61K 2039/507; G01N 33/541
USPC ....................................................... 435/69.1
See application file for complete search history.

(56) References Cited

U.S. PATENT DOCUMENTS 5,670,347 A  9/1997  Gopal et al.

FOREIGN PATENT DOCUMENTS

| EP | 0 779 365 A2 | 6/1997 |
|---|---|---|
| JP | 11-21255 | 2/1999 |
| JP | 2004-350502 | 12/2004 |
| WO | 00/40742 A1 | 7/2000 |
| WO | 01/38547 A3 | 5/2001 |
| WO | 01/81370 A3 | 11/2001 |
| WO | 02/055721 A2 | 7/2002 |
| WO | 2008/031598 A1 | 3/2008 |
| WO | 2011/003557 A1 | 1/2011 |
| WO | 2011/003780 A1 | 1/2011 |
| WO | 2011/113050 A1 | 9/2011 |
| WO | 2011/157715 A1 | 12/2011 |
| WO | 2013/056132 A3 | 4/2013 |
| WO | 2014/064258 A1 | 5/2014 |
| WO | 2018/060238 A1 | 4/2018 |

OTHER PUBLICATIONS

Adami et al., "Stability of Peptide-Condensed Plasmid DNA Formulations" J. Pharm. Sci. 87(6):678-683 ( 1998).
Balicki et al., "Histone H2A Significantly Enhances In Vitro DNA Transfection" Mol. Med. 3:782-787 ( 1997).
Bartneck et al., "Therapeutic targeting of liver inflammation and fibrosis by nanomedicine" Hepatobiliary Surg. Nutr. 3(6):364-376 ( 2014).
Blau and Springer et al., "Molecular Medicine Muscle-Mediated Gene Therapy" N. Engl. J. Med 333(23):1554-1556 ( 1995).
Bongartz et al., "Improved biological activity of antisense oligonucleotides conjugated to a fusogenic peptide" Nucleic Acids Res. 22:4681-4688 ( 1994).
Boulikas et al., "Nuclear Localization Signals (NLS)" Institute of Molecular Medical Sciences 3(3):193-227 ( 1993).
Budker et al., "Protein/Amphipathic Polyamine Complexes Enable Highly Efficient Transfection with Minimal Toxicity" Bio Techniques 23(1):139-147 ( 1997).
Cervia et al., "Distinct effects of endosomal escape and inhibition of endosomal trafficking on gene delivery via electrotransfection" PLoS ONE 12(2):e0171699 ( 2017).
Chen et al., "Design of a genetic immunotoxin to eliminate toxin immunogenicity" Gene Therapy 2:116-123 ( 1995).
Chen et al., "Galactosylated Histone-Mediated G e n e Transfer a n d Expression" Hum. Gene Ther. 5:429-435 ( 1994).
Cohen et al., "Naked DNA points way to vaccines" Science 259:1691-1692 ( 1993).
Cristiano et al., "Epidermal growth factor mediated DNA delivery into lung cancer cells via the epidermal growth factor receptor" Cancer Gene Therapy 3(1):4-10 ( 1996).
Dengl et al., "Engineered hapten-binding antibody derivatives for modulation of pharmacokinetic properties of small molecules and targeted payload delivery" Immunol. Rev. 270:165-177 ( 2016).
Duguid et al., "A Physicochemical Approach for Predicting the Effectiveness of PeptideBased Gene Delivery Systems for Use in Plasmid-Based Gene Therapy" Biophys. J. 74:2802-2814 ( 1998).
Felgner et al., "Nomenclature for synthetic gene delivery systems" Hum. Gene Ther. 8:511-512 ( 1997).
Felgner et al., "Nonviral Strategies for Many drawbacks of viral gene delivery agents might be overcome by nonviral systems. Studies in patients suggest these systems have potential as therapies and as vaccines" Sci. Am. 276:102-106 ( 1997).

(Continued)

*Primary Examiner* — Robert B Mondesi
*Assistant Examiner* — Mohammad Y Meah
(74) *Attorney, Agent, or Firm* — Nicole M. Fortuné

(57) ABSTRACT

Herein is reported a composition for the targeted delivery of large nucleic acids to the nucleus of a eukaryotic cell comprising non-covalent complexes of histones in form of assembled nucleosomes, a large nucleic acid, a hapten, and a bispecific binder that has a first binding specificity to the hapten and a second binding specificity to a cell-surface target present on the eukaryotic cell, wherein the histone and/or the nucleic acid is/are covalently bound/conjugated to the hapten, the histone and the large nucleic acid are associated (non-covalently) with each other/form a non-covalent complex, and the hapten and the bispecific binder are associated with each other/bound to each other by the first binding specificity of the bispecific binder.

12 Claims, 23 Drawing Sheets

Specification includes a Sequence Listing.

(56) References Cited

OTHER PUBLICATIONS

Friedler et al., "Modulation of Binding of DNA to the C-Terminal Domain of p53 by Acetylation" Structure 13:629-636 (2005).
Fritz et al., "Gene Transfer into Mammalian Cells using Histone-C+ondensed Plasmid DNA" Hum. Gene Ther. 7:1395-1404 (1996).
Gorlich et al., "Transport into and out of the cell nucleus" The EBRO Journal 17(10):2721-2727 (1998).
Haas et al., "Human-protein-derived peptides for intracellular delivery of biomolecules" Biochem. J. 442:583-593 (2012).
Hagstrom et al., "Complexes of non-cationic liposomes and histone HI mediate efficient transfection of DNA without encapsulation" Biochim. Biophys. Acta 1284:47-55 (1996).
Ibraheem et al., "Gene therapy and DNA delivery systems" Int. J. Pharm. 459:70-83 (2014).
International Preliminary Report on Patentability for PCT/EP2019/062417 issued on Nov. 24, 2020.
International Search Report for PCT/EP2019/062417 mailed on Jul. 2, 2019.
Killian et al., "Disruption of diphthamide synthesis genes and resulting toxin resistance as a robust technology for quantifying and optimizing CRISPR/Cas9-mediated gene editing" Sci Reports 7(1):15480 (Nov. 13, 2017).
Kim et al., "Targeted gene therapy of LS174 T human colon carcinoma by anti-TAG-72 immunoliposomes" Cancer Gene Therapy 15:331-340 (2008).
Mann et al., "Linear Short Histidine and Cysteine Modified Arginine Peptides Constitute a Potential Class of DNA Delivery Agents" Mol. Pharm. 11:683-696 (2014).
Mayer, K., et al., "TriFabs—Trivalent IgG-Shaped Bispecific Antibody Derivatives: Design, Generation, Characterization and Application for Targeted Payload Delivery" Int J Mol Sci 16(12):27497-27507 (Nov. 15, 2015).
McCaskill et al., "Efficient Biodistribution and Gene Silencing in the Lung epithelium via Intravenous Liposomal Delivery of siRNA" Mol. Ther. Nucleic Acids 2:E96 (2013).
Mingozzi et al., "Immune responses to AAV vectors: overcoming barriers to successful gene therapy" Blood 122(1):23-36 (2013).
Moffatt et al., "Successful in vivo tumor targeting of prostate-specific membrane antigen with a highly efficient J591/PEI/ DNA molecular conjugate" Gene Ther. 13:761-772 (2006).
Mosammaparast et al., "Nuclear Import of Histone H2A and H2B Is Mediated by a Network of Karyopherins" J. Cell Biol. 153(2):251-262 (2001).
Munch et al., "Displaying high-affinity ligands on adeno-associated viral vectors enables tumor cell-specific and safe gene transfer" Mol. Ther. 21(1):109-118 (2013).
Murphy et al., "A combinatorial approach to the discovery of efficient cationic peptoid reagents for gene delivery" Proc. Natl. Acad. Sci. USA 95:1517-1522 (1998).
Nagasaki et al., "Can Nuclear Localization Signals Enhance Nuclear Localization of Plasmid DNA?" Bioconjugate. Chem. 14:282-286 (2003).
Nayak et al., "Progress and prospects: immune responses to viral vectors" Gene Therapy 17:295-304 (2010).
Niidome et al., "Binding of Cationic a-Helical Peptides to Plasmid DNA and Their Gene Transfer Abilities into Cells" J. Biol. Chem. 272(24):15307-15312 (1997).
Novo et al., "Decationized polyplexes for gene delivery" Exp. Opin. Drug Deliv. 12(4):507-512 (2015).
Rosenbluh et al., "Non-endocytic penetration of core histones into petunia protoplastsand cultured cells: a novel mechanism for the introduction ofmacromolecules into plant cells" Biochim. Biophys. Acta 1664:230-240 (2004).
Rosenbluh et al., "Translocation of Histone Proteins Across Lipid Bilayers and Mycoplasma Membranes" J. Mol. Biol. 345:387-400 (2005).
Sanders et al., "Extracellular barriers in respiratory gene therapy" Adv. Drug Deliv. Rev. 61:115-127 (2009).
Schatzlein et al., "Targeting of Synthetic Gene Delivery Systems" J. Biomed. Biotechnol. 2:149-158 (2003).
Schneider et al., "Targeted siRNA Delivery and mRNA Knockdown Mediated by Bispecific Digoxigenin-binding Antibodies" Molecular Therapy-Nucleic Acids 1(e46):1-11 (2012).
Shimizu et al., "Immunogene approach toward cancer therapy using erythrocyte growth factor receptor-mediated gene delivery" Canger Gene Therapy 3(2):113-120 (1996).
Sternberg et al., "New structures in complex formation between DNA and cation liposomes visualized by freeze-fracture electron microscopy" FEBS Lett. 356:361-366 (1994).
Subramanian et al., "Nuclear targeting peptide scaffolds for lipofection of nondividing mammalian cells" Nat. Biotechnol. 17:873-877 (1999).
Varkouhi et al., "Endosomal escape pathways for delivery of biologicals" J. Cont. Rel. 151:220-228 (2011).
Veldwijk et al., "Differential expression of a recombinant adeno-associated virus 2 vector in human CD341 cells and breast cancer cells" Cancer Gene Ther. 7(4):597-604 (2000).
Wadhwa et al., "Peptide-Mediated Gene Delivery: Influence of Peptide Structure on Gene Expression" Bioconjugate. Chem. 8:81-88 (1997).
Wagstaff et al., "Efficient gene delivery using reconstituted chromatin enhanced for nuclear targeting" FASEB J. 22:2232-2242 (2008).
Wagstaff et al., "Histone-mediated Transduction as an EfficientMeans for Gene Delivery" Mol. Ther. 15(4):721-731 (2007).
Ward et al., "The rate of internalization of different receptor-ligand complexes in alveolar macrophages is receptor-specific" Biochem. J. 270:369-374 (1990).
Wilke et al., "Efficacy of a peptide-based gene delivery system depends on mitotic activity" Gene Ther. 3:1133-1142 (1996).
Wolff et al., "Breaking the Bonds: Non-viral Vectors Become Chemically Dynamic" Gene Ther. 16:8-15 (2008).
Wolff et al., "Direct Gene Transfer into Mouse Muscle in Vivo" Science 247:1465-1468 (1990).
Xu et al., "Tumor-targeted p53-gene therapy enhances the efficacy of conventional chemo/ radiotherapy" J. Contr. Rel. 74:115-128 (2001).
Zhang et al., "Near Complete Rescue of Experimental Parkinson's Disease with Intravenous, Non-viral GDNF Gene Therapy" Pharm. Res. 26(5):1059-1063 (May 2009).

A see peptide comparison in ‚C'

B

E phase fluorescence overlay

SEQUENCE LISTING

<160> NUMBER OF SEQ ID NOS: 74

<210> SEQ ID NO 1
<211> LENGTH: 130
<212> TYPE: PRT
<213> ORGANISM: Homo sapiens

<400> SEQUENCE: 1

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

```
Arg Leu Leu Arg Lys Gly Asn Tyr Ala Glu Arg Val Gly Ala Gly Ala
            35                  40                  45

Pro Val Tyr Leu Ala Ala Val Leu Glu Tyr Leu Thr Ala Glu Ile Leu
 50                  55                  60

Glu Leu Ala Gly Asn Ala Ala Arg Asp Asn Lys Lys Thr Arg Ile Ile
 65                  70                  75                  80

Pro Arg His Leu Gln Leu Ala Ile Arg Asn Asp Glu Glu Leu Asn Lys
                 85                  90                  95

Leu Leu Gly Lys Val Thr Ile Ala Gln Gly Gly Val Leu Pro Asn Ile
                100                 105                 110

Gln Ala Val Leu Leu Pro Lys Lys Thr Glu Ser His His Lys Ala Lys
            115                 120                 125

Gly Lys
    130

<210> SEQ ID NO 2
<211> LENGTH: 130
<212> TYPE: PRT
<213> ORGANISM: Bos taurus

<400> SEQUENCE: 2

Met Ser Gly Arg Gly Lys Gln Gly Gly Lys Ala Arg Ala Lys Ala Lys
 1               5                  10                  15

Thr Arg Ser Ser Arg Ala Gly Leu Gln Phe Pro Val Gly Arg Val His
            20                  25                  30

Arg Leu Leu Arg Lys Gly Asn Tyr Ala Glu Arg Val Gly Ala Gly Ala
            35                  40                  45

Pro Val Tyr Leu Ala Ala Val Leu Glu Tyr Leu Thr Ala Glu Ile Leu
 50                  55                  60

Glu Leu Ala Gly Asn Ala Ala Arg Asp Asn Lys Lys Thr Arg Ile Ile
 65                  70                  75                  80

Pro Arg His Leu Gln Leu Ala Ile Arg Asn Asp Glu Glu Leu Asn Lys
                 85                  90                  95

Leu Leu Gly Lys Val Thr Ile Ala Gln Gly Gly Val Leu Pro Asn Ile
                100                 105                 110

Gln Ala Val Leu Leu Pro Lys Lys Thr Glu Ser His His Lys Ala Lys
            115                 120                 125

Gly Lys
    130

<210> SEQ ID NO 3
<211> LENGTH: 129
<212> TYPE: PRT
<213> ORGANISM: Gallus gallus

<400> SEQUENCE: 3

Met Ser Gly Arg Gly Lys Gln Gly Gly Lys Ala Arg Ala Lys Ala Lys
 1               5                  10                  15

Ser Arg Ser Ser Arg Ala Gly Leu Gln Phe Pro Val Gly Arg Val His
            20                  25                  30

Arg Leu Leu Arg Lys Gly Asn Tyr Ala Glu Arg Val Gly Ala Gly Ala
            35                  40                  45

Pro Val Tyr Leu Ala Ala Val Leu Glu Tyr Leu Thr Ala Glu Ile Leu
 50                  55                  60

Glu Leu Ala Gly Asn Ala Ala Arg Asp Asn Lys Lys Thr Arg Ile Ile
 65                  70                  75                  80
```

```
Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile
            100                 105                 110

Gln Ala Val Leu Leu Pro Lys Lys Thr Asp Ser His Lys Ala Lys Ala
        115                 120                 125

Lys
```

<210> SEQ ID NO 4
<211> LENGTH: 126
<212> TYPE: PRT
<213> ORGANISM: Homo sapiens

<400> SEQUENCE: 4

```
Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
            20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125
```

<210> SEQ ID NO 5
<211> LENGTH: 126
<212> TYPE: PRT
<213> ORGANISM: Bos taurus

<400> SEQUENCE: 5

```
Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
            20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125
```

<210> SEQ ID NO 6
<211> LENGTH: 126
<212> TYPE: PRT

<213> ORGANISM: Gallus gallus

<400> SEQUENCE: 6

```
Met Pro Glu Pro Ala Lys Ser Ala Pro Ala Pro Lys Lys Gly Ser Lys
1               5                   10                  15

Lys Ala Val Thr Lys Thr Gln Lys Lys Gly Asp Lys Lys Arg Lys Lys
            20                  25                  30

Ser Arg Lys Glu Ser Tyr Ser Ile Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125
```

<210> SEQ ID NO 7
<211> LENGTH: 136
<212> TYPE: PRT
<213> ORGANISM: Homo sapiens

<400> SEQUENCE: 7

```
Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135
```

<210> SEQ ID NO 8
<211> LENGTH: 136
<212> TYPE: PRT
<213> ORGANISM: Homo sapiens

<400> SEQUENCE: 8

```
Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45
```

-continued

Leu Arg Glu Ile Arg Arg Tyr Gln Lys Ser Thr Glu Leu Leu Ile Arg
         50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ala Ala Ile Gly Ala Leu Gln Glu Ala
                 85                  90                  95

Ser Glu Ala Tyr Leu Val Gly Leu Phe Glu Asp Thr Asn Leu Cys Ala
                100                 105                 110

Ile His Ala Lys Arg Val Thr Ile Met Pro Lys Asp Ile Gln Leu Ala
                115                 120                 125

Arg Arg Ile Arg Gly Glu Arg Ala
            130                 135

<210> SEQ ID NO 9
<211> LENGTH: 136
<212> TYPE: PRT
<213> ORGANISM: Bos taurus

<400> SEQUENCE: 9

Met Ala Arg Thr Lys Gln Thr Ala Arg Lys Ser Thr Gly Gly Lys Ala
 1               5                  10                  15

Pro Arg Lys Gln Leu Ala Thr Lys Ala Ala Arg Lys Ser Ala Pro Ser
                 20                  25                  30

Thr Gly Gly Val Lys Lys Pro His Arg Tyr Arg Pro Gly Thr Val Ala
             35                  40                  45

Leu Arg Glu Ile Arg Arg Tyr Gln Lys Ser Thr Glu Leu Leu Ile Arg
         50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ala Ala Ile Gly Ala Leu Gln Glu Ala
                 85                  90                  95

Ser Glu Ala Tyr Leu Val Gly Leu Phe Glu Asp Thr Asn Leu Cys Ala
                100                 105                 110

Ile His Ala Lys Arg Val Thr Ile Met Pro Lys Asp Ile Gln Leu Ala
                115                 120                 125

Arg Arg Ile Arg Gly Glu Arg Ala
            130                 135

<210> SEQ ID NO 10
<211> LENGTH: 136
<212> TYPE: PRT
<213> ORGANISM: Gallus gallus

<400> SEQUENCE: 10

Met Ala Arg Thr Lys Gln Thr Ala Arg Lys Ser Thr Gly Gly Lys Ala
 1               5                  10                  15

Pro Arg Lys Gln Leu Ala Thr Lys Ala Ala Arg Lys Ser Ala Pro Ser
                 20                  25                  30

Thr Gly Gly Val Lys Lys Pro His Arg Tyr Arg Pro Gly Thr Val Ala
             35                  40                  45

Leu Arg Glu Ile Arg Arg Tyr Gln Lys Ser Thr Glu Leu Leu Ile Arg
         50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ala Ala Ile Gly Ala Leu Gln Glu Ala
                 85                  90                  95

-continued

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
            115                 120                 125

Arg Arg Ile Arg Gly Glu Arg Ala
            130                 135

<210> SEQ ID NO 11
<211> LENGTH: 103
<212> TYPE: PRT
<213> ORGANISM: Homo sapiens

<400> SEQUENCE: 11

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 12
<211> LENGTH: 103
<212> TYPE: PRT
<213> ORGANISM: Bos taurus

<400> SEQUENCE: 12

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 13
<211> LENGTH: 103
<212> TYPE: PRT
<213> ORGANISM: Gallus gallus

<400> SEQUENCE: 13

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
                20                  25                  30

Pro Ala Ile Arg Arg Leu Ala Arg Arg Gly Gly Val Lys Arg Ile Ser
            35                  40                  45

Gly Leu Ile Tyr Glu Glu Thr Arg Gly Val Leu Lys Val Phe Leu Glu
        50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
                100

<210> SEQ ID NO 14
<211> LENGTH: 441
<212> TYPE: PRT
<213> ORGANISM: Homo sapiens

<400> SEQUENCE: 14

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

```
Ser Lys Cys Gly Ser Lys Asp Asn Ile Lys His Val Pro Gly Gly Gly
        290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
            340                 345                 350
Lys Ile Gly Ser Leu Asp Asn Ile Thr His Val Pro Gly Gly Gly Asn
        355                 360                 365
Lys Lys Ile Glu Thr His Lys Leu Thr Phe Arg Glu Asn Ala Lys Ala
    370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
            420                 425                 430
Ser Ala Ser Leu Ala Lys Gln Gly Leu
        435                 440

<210> SEQ ID NO 15
<211> LENGTH: 5
<212> TYPE: PRT
<213> ORGANISM: Artificial Sequence
<220> FEATURE:
<223> OTHER INFORMATION: humanized anti-digoxigenin antibody HVR-H1

<400> SEQUENCE: 15

Asp Tyr Ala Met Ser
1               5

<210> SEQ ID NO 16
<211> LENGTH: 17
<212> TYPE: PRT
<213> ORGANISM: Artificial Sequence
<220> FEATURE:
<223> OTHER INFORMATION: humanized anti-digoxigenin antibody HVR-H2

<400> SEQUENCE: 16

Ser Ile Asn Ile Gly Ala Thr Tyr Ile Tyr Tyr Ala Asp Ser Val Lys
1               5                   10                  15
Gly

<210> SEQ ID NO 17
<211> LENGTH: 16
<212> TYPE: PRT
<213> ORGANISM: Artificial Sequence
<220> FEATURE:
<223> OTHER INFORMATION: humanized anti-digoxigenin antibody HVR-H3

<400> SEQUENCE: 17

Pro Gly Ser Pro Tyr Glu Tyr Asp Lys Ala Tyr Tyr Ser Met Ala Tyr
1               5                   10                  15

<210> SEQ ID NO 18
<211> LENGTH: 125
<212> TYPE: PRT
<213> ORGANISM: Artificial Sequence
<220> FEATURE:
<223> OTHER INFORMATION: humanized anti-digoxigenin antibody VH
```

<400> SEQUENCE: 18

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser
        115                 120                 125
```

<210> SEQ ID NO 19
<211> LENGTH: 11
<212> TYPE: PRT
<213> ORGANISM: Artificial Sequence
<220> FEATURE:
<223> OTHER INFORMATION: humanized anti-digoxigenin antibody HVR-L1

<400> SEQUENCE: 19

```
Arg Ala Ser Gln Asp Ile Lys Asn Tyr Leu Asn
1               5                   10
```

<210> SEQ ID NO 20
<211> LENGTH: 7
<212> TYPE: PRT
<213> ORGANISM: Artificial Sequence
<220> FEATURE:
<223> OTHER INFORMATION: humanized anti-digoxigenin antibody HVR-L2

<400> SEQUENCE: 20

```
Tyr Ser Ser Thr Leu Leu Ser
1               5
```

<210> SEQ ID NO 21
<211> LENGTH: 9
<212> TYPE: PRT
<213> ORGANISM: Artificial Sequence
<220> FEATURE:
<223> OTHER INFORMATION: humanized anti-digoxigenin antibody HVR-L3

<400> SEQUENCE: 21

```
Gln Gln Ser Ile Thr Leu Pro Pro Thr
1               5
```

<210> SEQ ID NO 22
<211> LENGTH: 108
<212> TYPE: PRT
<213> ORGANISM: Artificial Sequence
<220> FEATURE:
<223> OTHER INFORMATION: humanized anti-digoxigenin antibody VL

<400> SEQUENCE: 22

```
Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg
            100                 105

<210> SEQ ID NO 23
<211> LENGTH: 5
<212> TYPE: PRT
<213> ORGANISM: Artificial Sequence
<220> FEATURE:
<223> OTHER INFORMATION: humanized anti-biotin antibody HVR-H1

<400> SEQUENCE: 23

Asp Thr Phe Phe Gln
1               5

<210> SEQ ID NO 24
<211> LENGTH: 17
<212> TYPE: PRT
<213> ORGANISM: Artificial Sequence
<220> FEATURE:
<223> OTHER INFORMATION: humanized anti-biotin antibody HVR-H2

<400> SEQUENCE: 24

Arg Ile Asp Pro Ala Asn Gly Phe Thr Lys Tyr Ala Gln Lys Phe Gln
1               5                   10                  15

Gly

<210> SEQ ID NO 25
<211> LENGTH: 11
<212> TYPE: PRT
<213> ORGANISM: Artificial Sequence
<220> FEATURE:
<223> OTHER INFORMATION: humanized anti-biotin antibody HVR-H3

<400> SEQUENCE: 25

Trp Asp Thr Tyr Gly Ala Ala Trp Phe Ala Tyr
1               5                   10

<210> SEQ ID NO 26
<211> LENGTH: 120
<212> TYPE: PRT
<213> ORGANISM: Artificial Sequence
<220> FEATURE:
<223> OTHER INFORMATION: humanized anti-biotin antibody VH

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
```

```
                50               55                   60
Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser
        115                 120

<210> SEQ ID NO 27
<211> LENGTH: 11
<212> TYPE: PRT
<213> ORGANISM: Artificial Sequence
<220> FEATURE:
<223> OTHER INFORMATION: humanized anti-biotin antibody HVR-L1

<400> SEQUENCE: 27

Arg Ala Ser Gly Asn Ile His Asn Tyr Leu Ser
 1               5                  10

<210> SEQ ID NO 28
<211> LENGTH: 7
<212> TYPE: PRT
<213> ORGANISM: Artificial Sequence
<220> FEATURE:
<223> OTHER INFORMATION: humanized anti-biotin antibody HVR-L2

<400> SEQUENCE: 28

Ser Ala Lys Thr Leu Ala Asp
 1               5

<210> SEQ ID NO 29
<211> LENGTH: 9
<212> TYPE: PRT
<213> ORGANISM: Artificial Sequence
<220> FEATURE:
<223> OTHER INFORMATION: humanized anti-biotin antibody HVR-L3

<400> SEQUENCE: 29

Gln His Phe Trp Ser Ser Ile Tyr Thr
 1               5

<210> SEQ ID NO 30
<211> LENGTH: 107
<212> TYPE: PRT
<213> ORGANISM: Artificial Sequence
<220> FEATURE:
<223> OTHER INFORMATION: humanized anti-biotin antibody VL

<400> SEQUENCE: 30

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Tyr
            20                  25                  30

Leu Ser Trp Tyr Gln Gln Lys Pro Gly Lys Val Pro Lys Leu Leu Ile
         35                  40                  45

Tyr Ser Ala Lys Thr Leu Ala Asp Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln His Phe Trp Ser Ser Ile Tyr
```

85                  90                  95

Thr Phe Gly Gln Gly Thr Lys Leu Glu Ile Lys
                100                 105

<210> SEQ ID NO 31
<211> LENGTH: 6
<212> TYPE: PRT
<213> ORGANISM: Artificial Sequence
<220> FEATURE:
<223> OTHER INFORMATION: humanized anti-theophylline antibody HVR-H1

<400> SEQUENCE: 31

Ser Asp Tyr Ala Trp Asn
1               5

<210> SEQ ID NO 32
<211> LENGTH: 16
<212> TYPE: PRT
<213> ORGANISM: Artificial Sequence
<220> FEATURE:
<223> OTHER INFORMATION: humanized anti-theophylline antibody HVR-H2

<400> SEQUENCE: 32

Tyr Ile Arg Tyr Ser Gly His Thr Gly Tyr Asn Pro Ser Leu Lys Ser
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: humanized anti-theophylline antibody HVR-H3

<400> SEQUENCE: 33

Trp Val Asp Tyr Phe Asp Tyr
1               5

<210> SEQ ID NO 34
<211> LENGTH: 116
<212> TYPE: PRT
<213> ORGANISM: Artificial Sequence
<220> FEATURE:
<223> OTHER INFORMATION: humanized anti-theophylline antibody VH

<400> SEQUENCE: 34

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
                20                  25                  30

Tyr Ala Trp Asn Trp Ile Arg Gln His Pro Gly Lys Gly Leu Glu Trp
            35                  40                  45

Ile Gly Tyr Ile Arg Tyr Ser Gly His Thr Gly Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Val Asp Tyr Phe Asp Tyr Trp Gly Gln Gly Thr Leu Val
                100                 105                 110

Thr Val Ser Ser
        115

```
<210> SEQ ID NO 35
<211> LENGTH: 16
<212> TYPE: PRT
<213> ORGANISM: Artificial Sequence
<220> FEATURE:
<223> OTHER INFORMATION: humanized anti-theophylline antibody HVR-L1

<400> SEQUENCE: 35

Arg Ser Ser Gln Ser Ile Val Tyr Asn Asn Arg Tyr Thr Tyr Leu Glu
1               5                   10                  15

<210> SEQ ID NO 36
<211> LENGTH: 7
<212> TYPE: PRT
<213> ORGANISM: Artificial Sequence
<220> FEATURE:
<223> OTHER INFORMATION: humanized anti-theophylline antibody HVR-L2

<400> SEQUENCE: 36

Gly Val Ser Asn Arg Phe Ser
1               5

<210> SEQ ID NO 37
<211> LENGTH: 9
<212> TYPE: PRT
<213> ORGANISM: Artificial Sequence
<220> FEATURE:
<223> OTHER INFORMATION: humanized anti-theophylline antibody HVR-L3

<400> SEQUENCE: 37

Tyr Gln Gly Thr His Ala Pro Tyr Thr
1               5

<210> SEQ ID NO 38
<211> LENGTH: 112
<212> TYPE: PRT
<213> ORGANISM: Artificial Sequence
<220> FEATURE:
<223> OTHER INFORMATION: humanized anti-theophylline antibody VL

<400> SEQUENCE: 38

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Tyr Asn
                20                  25                  30

Asn Arg Tyr Thr Tyr Leu Glu Trp Phe Gln Gln Arg Pro Gly Gln Ser
            35                  40                  45

Pro Arg Leu Leu Ile Tyr Gly Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Gly
                85                  90                  95

Thr His Ala Pro Tyr Thr Phe Gly Gln Gly Thr Lys Leu Glu Ile Lys
            100                 105                 110

<210> SEQ ID NO 39
<211> LENGTH: 5
<212> TYPE: PRT
<213> ORGANISM: Mus musculus

<400> SEQUENCE: 39

His Tyr Trp Met Asn
1               5
```

<210> SEQ ID NO 40
<211> LENGTH: 19
<212> TYPE: PRT
<213> ORGANISM: Mus musculus

<400> SEQUENCE: 40

Gln Phe Arg Asn Lys Pro Tyr Asn Tyr Glu Thr Tyr Tyr Ser Asp Ser
1               5                   10                  15

Val Lys Gly

<210> SEQ ID NO 41
<211> LENGTH: 7
<212> TYPE: PRT
<213> ORGANISM: Mus musculus

<400> SEQUENCE: 41

Ala Ser Tyr Gly Met Glu Tyr
1               5

<210> SEQ ID NO 42
<211> LENGTH: 118
<212> TYPE: PRT
<213> ORGANISM: Mus musculus

<400> SEQUENCE: 42

Gly Val Lys Leu Asp Glu Thr Gly Gly Leu Val Gln Pro Gly Gly
1               5                   10                  15

Ala Met Lys Leu Ser Cys Val Thr Ser Gly Phe Thr Phe Gly His Tyr
            20                  25                  30

Trp Met Asn Trp Val Arg Gln Ser Pro Glu Lys Gly Leu Glu Trp Val
        35                  40                  45

Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser
        115

<210> SEQ ID NO 43
<211> LENGTH: 16
<212> TYPE: PRT
<213> ORGANISM: Mus musculus

<400> SEQUENCE: 43

Arg Ser Ser Gln Ser Leu Val His Ser Asn Gly Asn Thr Tyr Leu Arg
1               5                   10                  15

<210> SEQ ID NO 44
<211> LENGTH: 7
<212> TYPE: PRT
<213> ORGANISM: Mus musculus

<400> SEQUENCE: 44

Lys Val Ser Asn Arg Val Ser
1               5

<210> SEQ ID NO 45
<211> LENGTH: 9
<212> TYPE: PRT
<213> ORGANISM: Mus musculus

<400> SEQUENCE: 45

Ser Gln Ser Thr His Val Pro Trp Thr
1               5

<210> SEQ ID NO 46
<211> LENGTH: 120
<212> TYPE: PRT
<213> ORGANISM: Mus musculus

<400> SEQUENCE: 46

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Thr His Val Pro Trp Thr Phe Gly Gly Thr Lys Leu Glu Ile Lys
            100                 105                 110

Arg Thr Val Ala Ala Pro Ser Val
        115                 120

<210> SEQ ID NO 47
<211> LENGTH: 5
<212> TYPE: PRT
<213> ORGANISM: Mus musculus

<400> SEQUENCE: 47

Glu Tyr Pro Ile His
1               5

<210> SEQ ID NO 48
<211> LENGTH: 17
<212> TYPE: PRT
<213> ORGANISM: Artificial Sequence
<220> FEATURE:
<223> OTHER INFORMATION: humanized CDR-H2

<400> SEQUENCE: 48

Gly Ile Val Pro Asn Asn Gly Phe Thr Phe Tyr Ala Gln Lys Leu Gln
1               5                   10                  15

Gly

<210> SEQ ID NO 49
<211> LENGTH: 10
<212> TYPE: PRT
<213> ORGANISM: Mus musculus

<400> SEQUENCE: 49

Lys Asn Leu Gly Ser Ser Pro Leu Asp Tyr
1               5                   10

```
<210> SEQ ID NO 50
<211> LENGTH: 119
<212> TYPE: PRT
<213> ORGANISM: Artificial Sequence
<220> FEATURE:
<223> OTHER INFORMATION: humanized heavy chain variable domain

<400> SEQUENCE: 50
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Glu Tyr
            20                  25                  30

Pro Ile His Trp Val Arg Gln Ala Pro Gly Gln Gly Leu Glu Trp Met
        35                  40                  45

Gly Gly Ile Val Pro Asn Asn Gly Phe Thr Phe Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Lys Asn Leu Gly Ser Ser Pro Leu Asp Tyr Trp Gly Gln Gly
            100                 105                 110

Thr Thr Val Thr Val Ser Ser
        115

```
<210> SEQ ID NO 51
<211> LENGTH: 11
<212> TYPE: PRT
<213> ORGANISM: Mus musculus

<400> SEQUENCE: 51
```

Arg Ala Ser Gln Ser Ile Gly Thr Ser Ile His
1               5                   10

```
<210> SEQ ID NO 52
<211> LENGTH: 7
<212> TYPE: PRT
<213> ORGANISM: Mus musculus

<400> SEQUENCE: 52
```

Tyr Ala Ser Glu Ser Ile Ser
1               5

```
<210> SEQ ID NO 53
<211> LENGTH: 9
<212> TYPE: PRT
<213> ORGANISM: Mus musculus

<400> SEQUENCE: 53
```

Gln Gln Ser Asn Arg Trp Pro Leu Thr
1               5

```
<210> SEQ ID NO 54
<211> LENGTH: 107
<212> TYPE: PRT
<213> ORGANISM: Artificial Sequence
<220> FEATURE:
<223> OTHER INFORMATION: humanized light chain variable domain

<400> SEQUENCE: 54
```

Glu Ile Val Met Thr Gln Ser Pro Ala Thr Leu Ser Val Ser Pro Gly

```
            1               5                  10                 15
          Glu Arg Ala Thr Leu Ser Cys Arg Ala Ser Gln Ser Ile Gly Thr Ser
                         20                 25                 30

Ile His Trp Tyr Gln Gln Lys Pro Gly Gln Ala Pro Arg Leu Leu Ile
                         35                 40                 45

Lys Tyr Ala Ser Glu Ser Ile Ser Gly Ile Pro Ala Arg Phe Ser Gly
                         50                 55                 60

Ser Gly Ser Gly Thr Glu Phe Thr Leu Thr Ile Ser Ser Leu Gln Ser
           65                 70                 75                 80

Glu Asp Phe Ala Val Tyr Tyr Cys Gln Gln Ser Asn Arg Trp Pro Leu
                             85                 90                 95

Thr Leu Gly Gln Gly Thr Lys Leu Glu Ile Lys
                         100                105
```

<210> SEQ ID NO 55
<211> LENGTH: 109
<212> TYPE: PRT
<213> ORGANISM: Artificial Sequence
<220> FEATURE:
<223> OTHER INFORMATION: anti-helicar antibody VH

<400> SEQUENCE: 55

```
          Gln Ala Val Val Thr Gln Glu Pro Ser Leu Thr Val Ser Pro Gly Gly
           1               5                  10                 15

Thr Val Thr Leu Thr Cys Gly Ser Ser Thr Gly Ala Val Thr Thr Ser
                         20                 25                 30

Asn Tyr Ala Ser Trp Val Gln Gln Lys Pro Gly Gln Ala Phe Thr Gly
                         35                 40                 45

Leu Ile Gly Gly Thr Asn Asn Arg Ala Pro Trp Thr Pro Ala Arg Phe
                         50                 55                 60

Ser Gly Ser Leu Leu Gly Gly Lys Ala Ala Leu Thr Leu Ser Gly Ala
           65                 70                 75                 80

Gln Pro Glu Asp Glu Ala Glu Tyr Tyr Cys Ala Leu Trp Tyr Ser Asn
                             85                 90                 95

His Trp Val Phe Gly Gly Gly Thr Lys Leu Thr Val Leu
                         100                105
```

<210> SEQ ID NO 56
<211> LENGTH: 109
<212> TYPE: PRT
<213> ORGANISM: Artificial Sequence
<220> FEATURE:
<223> OTHER INFORMATION: anti-helicar antibody VL

<400> SEQUENCE: 56

```
          Asp Ala Val Val Thr Gln Glu Ser Ala Leu Thr Thr Ser Pro Gly Glu
           1               5                  10                 15

Thr Val Thr Leu Thr Cys Arg Ser Ser Thr Gly Ala Val Thr Thr Ser
                         20                 25                 30

Asn Tyr Ala Ser Trp Val Gln Glu Lys Pro Asp His Leu Phe Thr Gly
                         35                 40                 45

Leu Ile Gly Gly Thr Asn Asn Arg Ala Pro Gly Val Pro Ala Arg Phe
                         50                 55                 60

Ser Gly Ser Leu Ile Gly Asp Lys Ala Ala Leu Thr Ile Thr Gly Ala
           65                 70                 75                 80

Gln Thr Glu Asp Glu Ala Ile Tyr Phe Cys Ala Leu Trp Tyr Ser Asn
                             85                 90                 95
```

His Trp Val Phe Gly Gly Gly Thr Lys Leu Thr Val Leu
            100                 105

<210> SEQ ID NO 57
<211> LENGTH: 12
<212> TYPE: PRT
<213> ORGANISM: Saccharomyces cerevisiae

<400> SEQUENCE: 57

Ala His Leu Glu Asn Glu Val Ala Arg Leu Lys Lys
1               5                   10

<210> SEQ ID NO 58
<211> LENGTH: 4
<212> TYPE: PRT
<213> ORGANISM: Artificial Sequence
<220> FEATURE:
<223> OTHER INFORMATION: peptidic linker

<400> SEQUENCE: 58

Gly Gly Gly Ser
1

<210> SEQ ID NO 59
<211> LENGTH: 5
<212> TYPE: PRT
<213> ORGANISM: Artificial Sequence
<220> FEATURE:
<223> OTHER INFORMATION: peptidic linker

<400> SEQUENCE: 59

Gly Gly Gly Gly Ser
1               5

<210> SEQ ID NO 60
<211> LENGTH: 4
<212> TYPE: PRT
<213> ORGANISM: Artificial Sequence
<220> FEATURE:
<223> OTHER INFORMATION: peptidic linker

<400> SEQUENCE: 60

Gln Gln Gln Gly
1

<210> SEQ ID NO 61
<211> LENGTH: 5
<212> TYPE: PRT
<213> ORGANISM: Artificial Sequence
<220> FEATURE:
<223> OTHER INFORMATION: peptidic linker

<400> SEQUENCE: 61

Gln Gln Gln Gln Gly
1               5

<210> SEQ ID NO 62
<211> LENGTH: 4
<212> TYPE: PRT
<213> ORGANISM: Artificial Sequence
<220> FEATURE:
<223> OTHER INFORMATION: peptidic linker

<400> SEQUENCE: 62

Ser Ser Ser Gly
1

<210> SEQ ID NO 63
<211> LENGTH: 5
<212> TYPE: PRT
<213> ORGANISM: Artificial Sequence
<220> FEATURE:
<223> OTHER INFORMATION: peptidic linker

<400> SEQUENCE: 63

Ser Ser Ser Ser Gly
1               5

<210> SEQ ID NO 64
<211> LENGTH: 8
<212> TYPE: PRT
<213> ORGANISM: Artificial Sequence
<220> FEATURE:
<223> OTHER INFORMATION: peptidic linker

<400> SEQUENCE: 64

Gly Gly Gly Ser Gly Gly Gly Ser
1               5

<210> SEQ ID NO 65
<211> LENGTH: 12
<212> TYPE: PRT
<213> ORGANISM: Artificial Sequence
<220> FEATURE:
<223> OTHER INFORMATION: peptidic linker

<400> SEQUENCE: 65

Gly Gly Gly Ser Gly Gly Gly Ser Gly Gly Gly Ser
1               5                   10

<210> SEQ ID NO 66
<211> LENGTH: 16
<212> TYPE: PRT
<213> ORGANISM: Artificial Sequence
<220> FEATURE:
<223> OTHER INFORMATION: peptidic linker

<400> SEQUENCE: 66

Gly Gly Gly Ser Gly Gly Gly Ser Gly Gly Gly Ser Gly Gly Gly Ser
1               5                   10                  15

<210> SEQ ID NO 67
<211> LENGTH: 20
<212> TYPE: PRT
<213> ORGANISM: Artificial Sequence
<220> FEATURE:
<223> OTHER INFORMATION: peptidic linker

<400> SEQUENCE: 67

Gly Gly Gly Ser Gly Gly Gly Ser Gly Gly Gly Ser Gly Gly Gly Ser
1               5                   10                  15

Gly Gly Gly Ser
            20

<210> SEQ ID NO 68
<211> LENGTH: 10
<212> TYPE: PRT
<213> ORGANISM: Artificial Sequence
<220> FEATURE:
<223> OTHER INFORMATION: peptidic linker

<400> SEQUENCE: 68

Gly Gly Gly Gly Ser Gly Gly Gly Gly Ser

```
<210> SEQ ID NO 69
<211> LENGTH: 15
<212> TYPE: PRT
<213> ORGANISM: Artificial Sequence
<220> FEATURE:
<223> OTHER INFORMATION: peptidic linker

<400> SEQUENCE: 69

Gly Gly Gly Gly Ser Gly Gly Gly Gly Ser Gly Gly Gly Gly Ser
1               5                   10                  15

<210> SEQ ID NO 70
<211> LENGTH: 20
<212> TYPE: PRT
<213> ORGANISM: Artificial Sequence
<220> FEATURE:
<223> OTHER INFORMATION: peptidic linker

<400> SEQUENCE: 70

Gly Gly Gly Gly Ser Gly Gly Gly Gly Ser Gly Gly Gly Gly Ser Gly
1               5                   10                  15

Gly Gly Gly Ser
            20

<210> SEQ ID NO 71
<211> LENGTH: 17
<212> TYPE: PRT
<213> ORGANISM: Artificial Sequence
<220> FEATURE:
<223> OTHER INFORMATION: peptidic linker

<400> SEQUENCE: 71

Gly Ser Ser Ser Ser Ser Ser Ser Ser Ser Ser Ser Ser Ser Ser Ser
1               5                   10                  15

Gly

<210> SEQ ID NO 72
<211> LENGTH: 17
<212> TYPE: PRT
<213> ORGANISM: Artificial Sequence
<220> FEATURE:
<223> OTHER INFORMATION: peptidic linker

<400> SEQUENCE: 72

Gly Gly Gly Gly Gly Gly Ser Gly Gly Gly Gly Ser Gly Gly Gly Gly
1               5                   10                  15

Ser

<210> SEQ ID NO 73
<211> LENGTH: 22
<212> TYPE: PRT
<213> ORGANISM: Artificial Sequence
<220> FEATURE:
<223> OTHER INFORMATION: peptidic linker

<400> SEQUENCE: 73

Gly Gly Gly Gly Ser Gly Gly Gly Gly Ser Gly Gly Gly Gly Ser Gly
1               5                   10                  15

Gly Gly Gly Ser Gly Gly
            20

<210> SEQ ID NO 74
```

```
<211> LENGTH: 30
<212> TYPE: PRT
<213> ORGANISM: Artificial Sequence
<220> FEATURE:
<223> OTHER INFORMATION: peptidic linker

<400> SEQUENCE: 74

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

TARGETED INTRACELLULAR DELIVERY OF LARGE NUCLEIC ACIDS

CROSS REFERENCE TO RELATED APPLICATIONS

This application is a continuation of International Application No. PCT/EP2019/062417, filed May 15, 2019, claiming priority to foreign application No. EP 18173087.0 filed May 18, 2018 and foreign Application No. EP 18200414.3 filed Oct. 15, 2018, which are incorporated herein by reference in their entirety.

SEQUENCE LISTING

This application contains a Sequence Listing which has been submitted electronically in ASCII format and is hereby incorporated by reference in its entirety. Said ASCII copy, created on Nov. 11, 2020 is named Sequence_Listing.txt and is 42,002 bytes in size.

The current invention is in the field of nucleic acid delivery. Herein is reported a composition for the targeted delivery of large nucleic acids to the nucleus of a eukaryotic cell comprising a non-covalent complex of a histone, a large nucleic acid, a hapten, and a bispecific binder that has a first binding specificity to the hapten and a second binding specificity to a cell-surface target present on the eukaryotic cell.

BACKGROUND

Genetic material is active in the nucleus. The transport there can occur coincidentally during cell division when the nuclear envelope temporarily disintegrates in the course of mitosis or it has to be carried out actively. Thus, the active transport into the nucleus of living cells is necessary for the transfer of genetic material into all of those cells that do not divide in the period before the intended expression of the genetic material. A nuclear transport system for nucleic acids is very important because it is effective to allow the efficient transfer of DNA into those cells that divide rarely or not at all. Most primary cells belong to this group. Primary cells are of the highest scientific interest for two reasons. First, these cells that have freshly been isolated from the organism much better reflect the functional state of the cell type than cell lines derived from them. Second, they are the target cells for gene therapy. In addition, a nuclear transport system increases the efficiency of DNA transfer into established cell lines by enabling those cells to express transferred genetic material that have not divided in the period of time between start of transfer and analysis.

The bilayer membrane that envelops the nucleus includes pores. Small molecules can traverse these pores by diffusion. In order to be able to enter the nucleus, proteins larger than about 50 kDa need a nuclear localization signal (NLS) that has to be recognized by the transport machinery. An NLS is a signal peptide that mediates transfer of a cargo, which may be another peptide, from the cytoplasm into the nucleus of a cell. Typically, a functional signal consists of four to eight amino acids, is rich in positive amino acids arginine and lysine and contains proline. It is strongly conserved in evolution so that mammalian NLS also function in yeast. A classical NLS is, for example, the SV40 large T-antigen core sequence PKKKRKV. Heterologous NLS may also be used as a tool to transport target molecules into the nucleus. For this purpose, NLS can be incorporated into the sequences of cytoplasmic proteins at relatively random positions or NLS peptides can be coupled chemically to proteins or even gold particles (reviewed in Gorlich, D., EMBO J. 17 (1998) 2721-2727). An overview of NLS is given by Boulikas (Boulikas, T., Crit. Rev. Eukaryot. Gene Expr. 3 (1993) 193-227).

Targeted gene delivery is a therapeutic approach to address acquired or inherited diseases by providing gene products or by modifying the genetic setup of patients. To date, most nucleic acid delivery approaches for gene therapy are based upon either viral vectors or on cationic lipids and polymers with transfection-like properties. Antibodies or antibody derivatives (such as scFvs) or other cell or tissue-binding entities can be connected to such liposomal or viral delivery entities with the objective to improve targeting specificity and efficacy of nucleic acid delivery (see e.g. Kim, K. S., et al., Cancer Gene. Ther. 15 (2008) 331-340; Zhang, Y. & Pardridge, W. M., Pharm. Res. 26 (2009) 1059-1063; Xu, L., Pirollo, K. F. & Chang, E. H., J. Contr. Rel. 74 (2001) 115-128).

Gene delivery via virus-derived entities involves complex procedures to generate delivery systems. It involves viral components which can be recognized by the human immune system. Immunogenicity presents as potential safety and PK issue and can interfere with efficacy of targeted gene delivery (Nayak, S. & Herzog, R. W., Gene Ther. 17 (2010) 295-304; Mingozzi, F. & High, K. A., Blood 122 (2012) 23-36).

Synthetic delivery complexes such as DNA combined with lipids or polymers are less complex and do not harbor viral components. They are, however, frequently less effective than gene delivery via virus-derived entities. Inherent nonspecific membrane interaction properties of nanoparticles and/or entities with transfection like functionalities also generate potential safety/PK issues (Bartneck, M., Warzecha, K. T. & Tacke, F., Hepatobiliary Surg. Nutr. 3 (2014) 364-376).

Current state of the art delivery vehicles, virus—as well as lipid/polymer-derived, inherently interact with biological membranes. This is necessary to enable intracellular uptake and/or endosome escape of nucleic acids. Membrane interacting properties can support accumulation in and delivery to membrane-rich organs such as liver or lung. It does on the other hand provide an obstacle for delivery to other target organs, tissues or cells.

The efficacy of histones in DNA transfection has been described (Balicki and Beutler, Mol. Med. 3 (1997) 782-787; Budker et al., BioTechniques 23 (1997) 139-147; Chen et al., Hum. Gene Ther. 5 (1994) 429-435; Fritz et al., Hum. Gene Ther. 7 (1996) 1395-1404; Hagstrom et al., Biochim. Biophys. Acta 1284 (1996) 47-55). Histone H2A was by far the most efficient of all histone subclasses in mediating DNA transfection (Balicki and Beutler, supra, 1991).

Nagasaki et al. (Bioconjug. Chem. 14 (2003) 282-286) demonstrated that nuclear localization of plasmid DNA cannot be achieved by injecting conjugates of DNA and classical cationic NLS into the cytoplasm of cells. On the other hand, several artificial systems have been described that are supposed to increase transfection efficiency with the help of peptides or proteins containing nuclear localization signals.

Subramanian et al. (Nat. Biotechnol. 17 (1999) 873-877) disclosed a conjugate of a non-classical NLS and a cationic peptide scaffold derived from a scrambled sequence of the SV40 T-antigen consensus NLS in order to improve the final step of nuclear import with lipofection of non-dividing cells.

U.S. Pat. No. 5,670,347 disclosed a peptide that consists of a DNA-binding basic region, a flexible hinge region and an NLS. As DNA binding is achieved by the amino acids' positive charges also in this case, the reagent forms complexes with the DNA that are meant to serve for the transport across the cellular membrane at the same time. It is not evident why the NLS sequence should not participate in the binding of DNA, so that the actual signal for the nuclear transport proteins is likely to be masked by the DNA as long as the peptide is linked to it. Moreover, the complexes generated may become very large, what would impair transport through the nuclear pores.

WO 2000/40742 disclosed a nuclear transport agent comprising a DNA-binding part that binds specifically to DNA and an extended nuclear localization signal that has a substantially neutral net charge.

WO 2001/38547 disclosed polypeptides for transfer of molecules into eukaryotic cells that comprise at least two peptide monomers which each include a nuclear localization signal or a protein transduction domain. The nuclear localization signals used are classical NLS that naturally occur in proteins.

WO 2001/81370 disclosed a gene delivery system in which a gene delivery facilitating peptide, generally derived from Histone H2A, is complexed with a nucleic acid for efficient and stable delivery of the nucleic acid into a cell, ultimately to the nucleus. Such peptide-mediated gene delivery is based on the principal that non-neutralized positive charges on the histone are bound electrostatically both by the negatively charged phosphate backbone of DNA and that nuclear targeting signals in histones improve trafficking of the DNA to the nucleus for transcription. It is further disclosed an isolated gene delivery facilitating peptide comprising at least 7 amino acids, preferably 17 amino acids, derived from the N-terminal region of his tone H2A, wherein the peptide exhibits transfection activity and nuclear localization activity. Also disclosed is a complex comprising such a peptide complexed with a nucleic acid. Further, a solution comprising the complex and a transfection enhancing medium is disclosed.

It was disclosed in WO 2001/81370 that all of the cationic polymers tested bound to DNA, as demonstrated by agarose gel electrophoresis but DNA binding alone was insufficient for transfection, and that there is something particular to the sequence of amino acids in histone H2A that is responsible for its remarkable capacity to efficiently mediate gene delivery. It was further disclosed in WO 2001/81370 that the active portion of H2A in facilitating transfection and nuclear localization spans residues 1-36 and possesses both the nuclear localization signal (NLS) and the DNA clip properties.

WO 2002/055721 disclosed a modular transfection system comprising a protein that is capable of forming nucleoprotein filaments (NPFs) if loaded onto a nucleic acid to be transfected. The NPF-forming protein may be modified with a nuclear localization signal in order to improve transport of the nucleic acid into the nucleus of eukaryotic cells.

WO 2008/031598 disclosed a transport agent for transporting nucleic acids into eukaryotic cells and a method for producing said agent. The transport agent comprises a complex forming moiety that is capable of forming complexes with at least one nucleic acid molecule and condensing said nucleic acid molecule, and at least one nuclear localization moiety comprising at least one nuclear localization signal and having an approximately neutral net charge. It is disclosed in WO 2008/031598 that the combination of a moiety that binds and condenses nucleic acid molecules with a moiety that comprises an NLS but has a substantially neutral net charge leads to an effective transport agent which allows for a highly efficient transfer of molecules into eukaryotic cells.

But it is a drawback of classical nuclear localization signals that they tend toward binding of nucleic acids via their positive charges so that these charges are masked and their function as signals for the nuclear transport machinery is significantly impaired.

Cristiano, R. J., et al. disclosed epidermal growth factor mediated DNA delivery into lung cancer cells via the epidermal growth factor receptor (Cancer Gene Ther. 3 (1996) 4-10). Viruses are used for intracellular delivery into the cytoplasm or nucleus in the approach of Cristiano et al. Non-specific, charge-mediated interactions via poly-lysines are used to attach modifications to the DNA (EGF or virus).

Schneider, B., et al. disclosed targeted siRNA delivery and mRNA knockdown mediated by bispecific digoxigenin-binding antibodies (Mol. Ther. Nucleic Acids 1 (2012) e46). Lipids, chemically-generated nanoparticles or complexes with cell-penetrating peptides are used for intracellular delivery of small siRNA molecules into the cytoplasm or nucleus in the approach of Schneider et al.

EP 0 779 365 A2 disclosed methods to introduce nucleic acid into cells for therapeutic or diagnostic uses. These methods are based on complexes formed of chemically-modified DNA with an antibody. Domains of viral or bacterial origin are used for intracellular delivery into the cytoplasm or nucleus in the approach of EP 0 779 365 A2.

SUMMARY

Herein is reported a composition for the introduction of large nucleic acids into eukaryotic cells. The method is not suitable for small nucleic acids, such as siRNA or LNA. The introduced large nucleic acid can foster the transient or stable expression of a polypeptide encoded by a structural gene comprised on said large nucleic acid.

The current invention is based at least on part on the finding that only correctly assembled and functional chromatin successfully targets large nucleic acids into cells. It has further been found that neither not-correctly assembled chromatin nor non-specific histone-aggregates work in the targeted delivery of large nucleic acids.

The entities for the targeted delivery of large nucleic acid according to the current invention are more efficient in the intracellular delivery of large nucleic acid compared to non-specifically assembled complexes of histones or cell-penetrating-peptides or the like.

The entities and methods according to the current invention are free of compounds or entities of viral, bacterial or chemical-synthetic origin.

Thus, it has been found that for efficient intracellular delivery of large nucleic acids histones first have to be assembled into correctly folded and functional chromatin and second have to be combined with targeting domains/entities.

The defined assembly of histones into functional chromatin results in defined interactions with the large nucleic acid to be delivered and is essential for the intracellular delivery of large nucleic acids.

Known from the art are "transfections" with peptides or polypeptides in, e.g. transfection enhancing medium or buffer. The composition as reported herein is suitable for targeted uptake in conventional medium. No design of a specific medium is required making the use of the composition as reported herein easy.

Known from the art are "transfections" without targeting and, thus, specificity, i.e. all cells present in a solution are transfected independent of their phenotype. Thus, with the methods known from the art it is not possible to select specific sub-populations of a cell population for transfection. With the composition as reported herein this is not the case. By the targeting it is possible to selectively identify sub-populations of cells positive for one or more specific cell surface markers, i.e. cell-surface targets, within a larger population of cells. Thereby unwanted "side-effect" when applied in vivo can be avoided. It has to be pointed out that the composition as reported herein is inactive, i.e. non-transfecting, in the absence of cells presenting the respective cell-surface target. This provides for additional safety during in vivo use.

The current invention is based, at least in part, on the finding that with the composition as reported herein a target specific delivery of a large nucleic acid can be achieved.

Known from the art are non-defined complexes comprising histones and DNA. The composition as reported herein is a (stoichiometrically) defined composition. The composition as reported herein is based on correctly and defined assembled nucleosomes. This results in an improved transfection efficiency.

The current invention is based, at least in part, of the finding that with the composition as reported herein the addition of transfection enhancing agents is not required, i.e. can be omitted. Thereby, for example, the impact on cell viability, if any, after transfection is reduced or even negligible.

The current invention is based, at least in part, on the finding that with the composition as reported herein the transfection efficiency compared to known methods under comparable conditions is improved.

The current invention comprises entities for the targeted intracellular delivery and intracellular functionality of large nucleic acids incl. expression plasmids. These entities comprise (i) the nucleic acid to be delivered, such as e.g. a plasmid,
(ii) one or more histones functionally assembled with the nucleic acid to form one or more nucleosomes, and
(iii) a cell-surface targeting entity conjugated to the plasmid-nucleosome assemblies (this cell-surface targeting entity enables specific delivery to and into a defined population of cells).

The conjugation of the cell-surface targeting entity to the nucleic acid-nucleosome complexes can be achieved in different ways. One possibility is by attaching haptens to the histone (e.g. via chemical or genetic conjugation-) or the plasmid DNA (e.g. via DNA binding peptides) followed by complexation with hapten-binding bispecific antibodies (bs-Abs). Another possibility is by direct recombinant fusion or chemical conjugation of the cell-surface targeting entity to the histone.

The new delivery entities according to the current invention do not contain viral components. Additionally, these entities carry a low immunogenicity risk as their protein components are generated from human sequences (human histones and humanized antibody derivatives). Furthermore, these delivery entities display no or only very low non-specific membrane interacting properties. This has been evidenced by lack of uptake into cells not recognized by the cell-surface targeting entity. Efficacy of gene delivery into cells that express surface antigen recognized by the cell-surface targeting entity reaches levels comparable to viral delivery and is more efficient compared to transfection-like nanoparticle/polymer methods.

One aspect as reported herein is a composition for the targeted delivery of large nucleic acids to the nucleus of a eukaryotic cell comprising a histone (one or more histone polypeptides),
a large nucleic acid,
a hapten, and
a bispecific binder that has a first binding specificity (a first binding site that specifically binds) to the hapten and a second binding specificity (a second binding site) to an antigen (a cell-surface target present) on the eukaryotic cell, wherein the histone and/or the nucleic acid is/are covalently bound/conjugated to the hapten,
the histone and the large nucleic acid are associated (non-covalently) with each other/form a non-covalent complex/form a functional chromatin complex/form a (one or more) nucleosome, and
the hapten and the bispecific binder are associated with each other/bound to each other by the first binding specificity of the bispecific binder.

In one embodiment the histone and the large nucleic acid form (functional) chromatin.

In one embodiment the composition is free of bacterial proteins.

In one embodiment the composition if free of viral elements except for the large nucleic acid.

In one embodiment the elements of the composition form a (stoichiometrically) defined and/or stable and/or isolatable complex.

In one embodiment the composition has an efficiency of at least 2-times the efficiency of a composition comprising non-defined/non-specific histone-nucleic acid complexes, i.e. non-functional chromatin.

In one embodiment the composition further comprises a sufficient number of histone polypeptides in order to assemble the large nucleic acid into one or more nucleosomes. In one embodiment the composition comprises at most/approximately/about 1 nucleosome per 150 bp of the large nucleic acid.

In one embodiment the composition further comprises about 8 histone polypeptides per at most 150 bp of the large nucleic acid.

In one embodiment the composition further comprises about one nucleosome per at most 150 bp of the large nucleic acid.

In one embodiment the histone in the composition is a mixture of two or more different histones. In one embodiment the mixture is a mixture of histones H2A, H2B, H3 and H4.

In one embodiment the histone/histones in the composition is/are calf thymus histones, chicken erythrocyte histones, recombinant human histones, or mixtures thereof.

In one embodiment the histone/histones in the composition is/are a mixture of histone H2A and histone H3 polypeptides.

In one embodiment the histone in the composition is recombinant human histone H3.

In one embodiment the histone in the composition is recombinant human histone H3.1 or H3.3.

The different histones identified in the embodiments above have the following amino acid sequences:

| histone | species | SEQ ID NO: | Uniprot ID |
| --- | --- | --- | --- |
| H2A | human | 01 | P0C0S8 |
| | bovine | 02 | P0C0S9 |
| | chicken | 03 | P02263 |
| H2B | human | 04 | P62807 |
| | bovine | 05 | P62808 |
| | chicken | 06 | P0C1H3 |
| H3 | human H3.1 | 07 | P68431 |
| | human H3.3 | 08 | P84243 |
| | bovine H3.3 | 09 | P68432 |
| | chicken H3.3 | 10 | P84247 |
| H4 | human | 11 | P62805 |
| | bovine | 12 | P62803 |
| | chicken | 13 | P62801 |

In one embodiment the large nucleic acid is exactly one large nucleic acid molecule.

In one embodiment the large nucleic acid is selected from an expression plasmid comprising at least one expression cassette and an isolated expression cassette.

In one embodiment the large nucleic acid comprises between 1,000 and 100,000 nucleotides or base pairs. In another embodiment the large nucleic acid comprises between 1,250 and 20,000 nucleotides or base pairs. In a further embodiment the large nucleic acid comprises between 1,500 and 10,000 nucleotides or base pairs.

In one embodiment the histone is human histone H3.1 or H3.3 or calf thymus histone. In one embodiment the human histone is not chemically derivatized. In one embodiment the human histone is not conjugated to a hapten.

In one embodiment the histone is calf thymus histone and about 2 µg histone per µg large nucleic acid is used.

In one embodiment the histone is recombinant human histone and about 0.8-1 µg histone per µg large nucleic acid is used.

In one embodiment the histone is chicken erythrocyte histone and about 1 µg histone per µg large nucleic acid is used.

In one embodiment the composition further comprises at least one hapten molecule. In one embodiment the composition comprises two or more hapten molecules and the two or more hapten molecules are the same hapten molecule or different hapten molecules. In one embodiment hapten/hapten molecule is selected from biotin, digoxygenin, theophylline, bromodeoxyuridine, fluorescein, DOTAM and helicar motif polypeptides.

In one embodiment of the composition the hapten is further chemically conjugated to the histone or large nucleic acid.

In one embodiment of the composition the hapten is further conjugated to a DNA binding peptide, which is attached to the large nucleic acid.

In one embodiment of the composition the/each histone polypeptide is further conjugated to a single hapten molecule and/or the large nucleic acid molecule is further conjugated to at least one hapten molecule.

In one embodiment of the composition the bispecific binder is selected from a bispecific antibody, a bispecific scaffold, a bispecific peptide, a bispecific aptamer, a bispecific low-molecular-weight-structure. In one embodiment the bispecific antibody is selected from a bispecific full-length antibody, a bispecific CrossMab, a bispecific T-cell bispecific, a DAF, and a DutaMab. In one embodiment the bispecific antibody is a bispecific antibody fragment. In one embodiment the bispecific antibody fragment is selected from a DutaFab, a F(ab')2, tandem scFv, diabody, tandAb, scFv2-CH1/CL, and VHH2-CH1/CL.

In one embodiment of the composition the cell-surface target is an internalizing cell-surface receptor. In one embodiment the cell surface target is an internalizing cell-surface receptor that is selected from the group consisting of cell type specific carbohydrates, receptor tyrosine kinases such as HER1, HER2, HER3, IGF1R, cell type specific antigens, such as Mesothelin, PSMA, CD19, CD20, CD44, TfR, LRPs, IL-receptors.

In one embodiment the composition further comprises exactly one bispecific binder or two or more copies of the bispecific binder.

In one embodiment of the composition the hapten is biotin, the bispecific binder is a bispecific antibody and the first binding specificity is a pair of an antibody light chain variable domain and an antibody heavy chain variable domain comprising (a) a HVR-H1 comprising the amino acid sequence of SEQ ID NO: 23, (b) a HVR-H2 comprising the amino acid sequence of SEQ ID NO: 24, (c) a HVR-H3 comprising the amino acid sequence of SEQ ID NO: 25, (d) a HVR-L1 comprising the amino acid sequence of SEQ ID NO: 27, (e) a HVR-L2 comprising the amino acid sequence of SEQ ID NO: 28, and (f) a HVR-L3 comprising the amino acid sequence of SEQ ID NO: 29.

In one embodiment of the composition the hapten is digoxygenin, the bispecific binder is a bispecific antibody and the first binding specificity is a pair of an antibody light chain variable domain and an antibody heavy chain variable domain comprising (a) a HVR-H1 comprising the amino acid sequence of SEQ ID NO: 15, (b) a HVR-H2 comprising the amino acid sequence of SEQ ID NO: 16, (c) a HVR-H3 comprising the amino acid sequence of SEQ ID NO: 17, (d) a HVR-L1 comprising the amino acid sequence of SEQ ID NO: 19, (e) a HVR-L2 comprising the amino acid sequence of SEQ ID NO: 20, and (f) a HVR-L3 comprising the amino acid sequence of SEQ ID NO: 21.

In one embodiment of the composition the hapten is theophylline, the bispecific binder is a bispecific antibody and the first binding specificity is a pair of an antibody light chain variable domain and an antibody heavy chain variable domain comprising (a) a HVR-H1 comprising the amino acid sequence of SEQ ID NO: 31, (b) a HVR-H2 comprising the amino acid sequence of SEQ ID NO: 32, (c) a HVR-H3 comprising the amino acid sequence of SEQ ID NO: 33, (d) a HVR-L1 comprising the amino acid sequence of SEQ ID NO: 35, (e) a HVR-L2 comprising the amino acid sequence of SEQ ID NO: 36, and (f) a HVR-L3 comprising the amino acid sequence of SEQ ID NO: 37.

In one embodiment of the composition the hapten is fluorescein, the bispecific binder is a bispecific antibody and the first binding specificity is a pair of an antibody light chain variable domain and an antibody heavy chain variable domain comprising (a) a HVR-H1 comprising the amino acid sequence of SEQ ID NO: 39, (b) a HVR-H2 comprising the amino acid sequence of SEQ ID NO: 40, (c) a HVR-H3 comprising the amino acid sequence of SEQ ID NO: 41, (d) a HVR-L1 comprising the amino acid sequence of SEQ ID NO: 43, (e) a HVR-L2 comprising the amino acid sequence of SEQ ID NO: 44 and (f) a HVR-L3 comprising the amino acid sequence of SEQ ID NO: 45.

In one embodiment of the composition the hapten is bromodeoxyuridine, the bispecific binder is a bispecific antibody and the first binding specificity is a pair of an antibody light chain variable domain and an antibody heavy chain variable domain comprising (a) a HVR-H1 comprising the amino acid sequence of SEQ ID NO: 47, (b) a HVR-H2 comprising the amino acid sequence of SEQ ID NO: 48, (c) a HVR-H3 comprising the amino acid sequence of SEQ ID NO: 49, (d) a HVR-L1 comprising the amino acid sequence of SEQ ID NO: 51, (e) a HVR-L2 comprising the amino acid sequence of SEQ ID NO: 52, and (f) a HVR-L3 comprising the amino acid sequence of SEQ ID NO: 53.

In one embodiment of the composition the hapten is a helicar motif polypeptide of SEQ ID NO: 57, the bispecific binder is a bispecific antibody and the first binding specificity is a pair of an antibody light chain variable domain and an antibody heavy chain variable domain comprising a HVR-H1, a HVR-H2 and a HVR-H3 of SEQ ID NO: 55, and a HVR-L1, a HVR-L2 and a HVR-L3 of SEQ ID NO: 56.

In one embodiment of the composition each hapten is further specifically bound by one/a single bispecific binder.

In one embodiment of the composition the large nucleic acid encodes CRISPR/Cas9.

In one embodiment of the composition the large nucleic acid further comprises:
CRISPR/Cas-system nucleic acids, and/or
an expression cassette for an polypeptide endogenous to the mammalian cell, and/or
an expression cassette for polypeptides that encodes enzymes or other proteins/peptides with therapeutic function, and/or
a transcription system for non-coding RNA with therapeutic function like micro RNA, short interfering RNA, long non-coding RNA, RNA decoys, RNA aptamers and ribozymes.

In one embodiment the histone is naturally-occurring histone with wild-type amino acid sequence.

In one embodiment the composition is free of compounds of viral or bacterial origin except for the sequence of the large nucleic acid to be delivered.

One aspect as reported herein is a pharmaceutical formulation comprising the composition as reported herein and a pharmaceutically acceptable carrier.

In one embodiment the pharmaceutical formulation is further for use as a medicament.

In one embodiment the pharmaceutical formulation is further for use in gene therapy.

One aspect as reported herein is the use of the composition as reported herein in the manufacture of a medicament.

One aspect as reported herein is a method of treating an individual having a genetic disease comprising administering to the individual an effective amount of the composition as reported herein, wherein the large nucleic acid comprises (within an expression cassette) a structural gene encoding a polypeptide required to treat the genetic disease.

One aspect as reported herein is a method of modifying gene expression in the cells of an individual comprising administering to the individual an effective amount of the composition as reported herein, wherein the large nucleic acid comprises either (within an expression cassette) a structural gene encoding a polypeptide required to modify the gene expression or a therapeutic nucleic acid.

One aspect as reported herein is a method for preparing a composition as reported herein comprising the following steps:
a) incubating the large nucleic acid and the histone to form a large-nucleic-acid-histone-complex, wherein either the large nucleic acid or the histone or both are conjugated to at least one hapten molecule,
b) incubating complex formed in a) with a bispecific binder to generate a bispecific-binder-large-nucleic-acid-histone-complex,
c) isolating and/or purifying the complex formed in step b) and thereby producing the composition as reported herein.

One aspect as reported herein is a method for introducing a large nucleic acid into a eukaryotic cell comprising the following step(s):
a) incubating a eukaryotic cell with a composition as reported herein under conditions suitable for the binding of the bispecific binder to the cell-surface target,
b) isolating a cell comprising the large nucleic acid or a functional fragment thereof, and thereby introducing a large nucleic acid into a eukaryotic cell.

One aspect as reported herein is a method for transfecting a eukaryotic cell comprising the following step(s):
a) incubating a eukaryotic cell with a composition as reported herein under conditions suitable for the binding of the bispecific binder to the cell-surface target,
b) isolating a cell comprising the large nucleic acid or a functional fragment thereof, and thereby transfecting a eukaryotic cell.

One aspect as reported herein is a method for transporting a nucleic acid into a eukaryotic cell comprising the following step(s):
a) incubating a eukaryotic cell with a composition as reported herein under conditions suitable for the binding of the bispecific binder to the cell-surface target,
b) isolating a cell comprising the large nucleic acid or a functional fragment thereof, and thereby transporting a large nucleic acid into a eukaryotic cell.

One aspect as reported herein is a method for transporting a nucleic acid into the nucleus of a eukaryotic cell comprising the following step(s):
a) incubating a eukaryotic cell with a composition as reported herein under conditions suitable for the binding of the bispecific binder to the cell-surface target,
b) isolating a cell comprising the large nucleic acid or a functional fragment thereof, and thereby transporting a large nucleic acid into the nucleus of a eukaryotic cell.

One aspect as reported herein is the use of a composition as reported herein for the targeted delivery of a large nucleic acid into a eukaryotic cell.

One aspect as reported herein is the use of a composition as reported herein for the introduction of a large nucleic acid or a functional fragment thereof into the nucleus of a eukaryotic cell.

In one embodiment the composition is further for the introduction of a large nucleic acid or a functional fragment thereof into a eukaryotic cell.

In one embodiment the composition is further for the transfection of a eukaryotic cell with a large nucleic acid or functional fragment thereof.

One aspect as reported herein is a cell obtained with a method using a composition as reported herein and the progeny thereof.

One aspect as reported herein is a method for transfecting a defined subpopulation of a population of eukaryotic cells comprising the following step:
incubating a population of eukaryotic cells comprising at least two subpopulations differing in at least one cell-surface antigen with a composition as reported herein, wherein the second binding specificity of the bispecific binder specifically binds to a cell-surface antigen that is specific for a (single) subpopulation of the population of eukaryotic cells, and thereby transfecting a defined subpopulation of a population of eukaryotic cells.

Beside haptens as outlined above also other means for linking the targeting entity to the large nucleic acid can be used. These include, without limitation,

- conjugates or fusions to histones,
- conjugates or fusions of haptens or binding entities to DNA-binding entities/peptides,
- bi- or multispecific entities that bind histone (e.g. anti-histone bsAb),
- bi- or multispecific entities that bind DNA (e.g. anti-DNA bsAb),
- bi- or multispecific entities that bind modified nucleotides (e.g. anti-BrdU bsAb).

Advantages of the composition according to the invention are a minimum of toxicity to the recipient cell or organism, with cellular access, intracellular trafficking and nuclear retention of plasmids.

The composition according to the current invention can serve to facilitate the nuclear localization of therapeutic peptides/nucleic acids while conferring the advantages of plasmid retention, lack of endosomal entrapment and protection from nucleases and the like cellular processes.

Provision of the composition/transport agent according to the current invention is also an essential step toward a completely artificial gene transfer system for gene therapy. Such a gene transfer system must possess three functional components: one component for the passage of DNA through the cellular membrane, a second component for the transfer of the DNA into the nucleus of the (usually non-dividing) target cells and a third component that mediates the integration of the DNA into the genome. A completely artificial gene transfer composition that can be employed in gene therapy will in all likelihood be easier and less expensive to produce and easier to handle than the viral systems currently applied, and it is not subject to the immanent risks of these systems.

The composition according to the present invention also increases the transfection efficiency in cultured cells.

In a preferred embodiment of the invention, the above method(s) are accomplished with eukaryotic cells that are resting, slowly dividing or non-dividing cells, preferably primary cells and or at least one DNA molecule as nucleic acid.

DETAILED DESCRIPTION OF EMBODIMENTS OF THE INVENTION

The current invention is based, at least in part, on the finding that with the composition as reported herein the transfection of eukaryotic cells with peptide- or polypeptide-encoding large nucleic acids can be achieved in conventional medium.

The current invention is based, at least in part, on the finding that with the composition as reported herein the targeted transfection of sub-populations with a eukaryotic cell population is possible depending on their phenotype. By the targeting it is possible to selectively identify sub-populations of cells positive for one or more specific cell surface markers, i.e. cell-surface targets, within a larger population of cells. Thereby unwanted "side-effect" when applied in vivo can be avoided. This provides for additional safety during in vivo use.

The current invention is based, at least in part, on the finding that with the composition as reported herein a target specific delivery of a large nucleic acid can be achieved.

The current invention is based, at least in part, of the finding that with the composition as reported herein the addition of transfection enhancing agents is not required, i.e. can be omitted. Thereby, for example, the impact on cell viability, if any, after transfection is reduced or even negligible.

The current invention is based, at least in part, on the finding that with the composition as reported herein the transfection efficiency compared to known methods under comparable conditions is improved.

Definitions

The knobs into holes dimerization modules and their use in antibody engineering are described in Carter P.; Ridgway J. B. B.; Presta L. G.: Immunotechnology, Volume 2, Number 1, February 1996, pp. 73-73(1).

The CH3 domains in the heavy chains of an antibody can be altered by the "knob-into-holes" technology, which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of these two CH3 domains and thereby of the polypeptide comprising them. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield. But this is absent in the molecules of the current invention.

The mutation T366W in the CH3 domain (of an antibody heavy chain) is denoted as "knob-mutation" or "mutation knob" and the mutations T366S, L368A, Y407V in the CH3 domain (of an antibody heavy chain) are denoted as "hole-mutations" or "mutations hole" (numbering according to Kabat EU index). An additional inter-chain disulfide bridge between the CH3 domains can also be used (Merchant, A. M., et al., Nature Biotech. 16 (1998) 677-681) e.g. by introducing a S354C mutation into the CH3 domain of the heavy chain with the "knob-mutation" (denotes as "knob-cys-mutations" or "mutations knob-cys") and by introducing a Y349C mutation into the CH3 domain of the heavy chain with the "hole-mutations" (denotes as "hole-cys-mutations" or "mutations hole-cys") (numbering according to Kabat EU index). But this is absent in the molecules of the current invention.

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R I., Culture of Animal Cells: A Manual of Basic Technique, second edition, Alan R. Liss, Inc., N.Y. (1987).

The use of recombinant DNA technology enables the generation of derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

An "antibody fragment" refers to a molecule other than an intact antibody that comprises a portion of an intact antibody that binds the antigen to which the intact antibody binds. Examples of antibody fragments include but are not limited to Fv, scFv, Fab, scFab, Fab', Fab'-SH, F(ab')2; diabodies; linear antibodies; single-chain antibody molecules (e.g. scFv); and multispecific antibodies formed from antibody fragments. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. Nos. 5,571,894 and 5,587,458.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g. E. coli or phage).

The term "antibody fragment" also includes a "Dual Acting Fab" or "DAF" comprising an antigen binding site that binds to two different antigens (see, US 2008/0069820, for example).

The term "binding (to an antigen)" denotes the binding of an antibody in an in vitro assay. In one embodiment binding is determined in a binding assay in which the antibody is bound to a surface and binding of the antigen to the antibody is measured by Surface Plasmon Resonance (SPR). Binding means e.g. a binding affinity (KD) of $10^{-8}$ M or less, in some embodiments of $10^{-13}$ to $10^{-8}$ M, in some embodiments of $10^{-13}$ to $10^{-9}$ M. The term "binding" also includes the term "specifically binding".

For example, in one possible embodiment of the BIAcore® assay the antigen is bound to a surface and binding of the antibody binding site is measured by surface plasmon resonance (SPR). The affinity of the binding is defined by the terms ka (association constant: rate constant for the association to form a complex), kd (dissociation constant; rate constant for the dissociation of the complex), and KD (kd/ka). Alternatively, the binding signal of a SPR sensorgram can be compared directly to the response signal of a reference, with respect to the resonance signal height and the dissociation behaviors.

The term "binding site" as used herein denotes a polypeptide or a pair of polypeptides that can specifically bind to a second polypeptide. In one embodiment the binding site is selected from the group of polypeptides consisting of an antibody heavy chain variable domain, an antibody light chain variable domain, a pair of an antibody heavy chain and an antibody light chain variable domains, a receptor or functional fragment thereof, a ligand or a functional fragment thereof, an enzyme or its substrate. The term "comprising" also includes the term "consisting of".

An "effective amount" of an agent, e.g., a pharmaceutical formulation, refers to an amount effective, at dosages and for periods of time necessary, to achieve the desired therapeutic or prophylactic result.

The terms "full length antibody", "intact antibody", and "whole antibody" are used herein interchangeably to refer to an antibody having a structure substantially similar to a native antibody structure.

The term "full length antibody" denotes an antibody having a structure substantially similar to a native antibody structure. A full length antibody comprises two full length antibody light chains each comprising a light chain variable domain and a light chain constant domain, and two full length antibody heavy chains each comprising a heavy chain variable domain, a first constant domain, a hinge region, a second constant domain and a third constant domain. A full length antibody may comprise further domains, such as e.g. additional scFv or a scFab conjugated to one or more of the chains of the full length antibody. These conjugates are also encompassed by the term full length antibody.

The terms "eukaryotic cell", "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "humanized" antibody refers to an antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, MD (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" composition is one which has been separated from a component of its natural environment. In some embodiments, a composition is purified to greater than 95% or 99% purity as determined by, for example, electrophoretic (e.g., SDS-PAGE, isoelectric focusing (IEF), capillary electrophoresis) or chromatographic (e.g., size exclusion chromatography or ion exchange or reverse phase HPLC). For review of methods for assessment of e.g. antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "monospecific antibody" denotes an antibody that has a single binding specificity for one antigen. Monospecific antibodies can be prepared as full-length antibodies or antibody fragments (e.g. F(ab')2) or combinations thereof (e.g. full length antibody plus additional scFv or Fab fragments).

A "multispecific antibody" denotes an antibody that has binding specificities for at least two different epitopes on the same antigen or two different antigens. Multispecific antibodies can be prepared as full-length antibodies or antibody fragments (e.g. F(ab')2 bispecific antibodies) or combinations thereof (e.g. full length antibody plus additional scFv or Fab fragments). Engineered antibodies with two, three or more (e.g. four) functional antigen binding sites have also been reported (see, e.g., US 2002/0004587 A1). One multispecific antibody is a bispecific antibody. Multi-specific antibodies may also be made by engineering electrostatic steering effects for making antibody Fc-heterodimeric molecules (WO 2009/089004).

A "naked multispecific antibody" refers to a multispecific antibody that is not conjugated to a moiety (e.g., a cytotoxic moiety) or radiolabel. The naked multispecific antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), whereby between the first and the second constant domain a hinge region is located. Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "nucleosome" denotes a particle comprising DNA and histones. Chromatin is the macromolecular state in which nuclear DNA is packaged within the cell. Nucleosomes are the structural units of chromatin. Each nucleosome is composed of about 150 bp double stranded DNA and a histone octamer which contains two copies of each core histone (H2A, H2B, H3 and H4). Histone H1, a linker histone, is involved in binding between nucleosomes to further compact the chromatin (Luger, K., et al. Nature 389 (1997) 251-260; Chakravarthy, S., et al. FEBS Lett. 579 (2005) 895-898). Thus, in eukaryotes a nucleosome is the basic unit of DNA packing. The nucleosome core particle comprises approximately 150 base pairs (bp) of DNA wrapped in left-handed superhelical turns around a histone octamer. For example, the histone octamer may consist of 2 copies each of the histones H2A, H2B, H3, and H4. Core particles are generally connected by stretches of so called "linker DNA". This linker DNA can comprise up to about 80 bps. Herein the term "nucleosome" denotes the core particle optionally plus one of the linker DNAs. The presence of one or more nucleosomes is the requirement for functional chromatin.

The term "package insert" is used to refer to instructions customarily included in commercial packages of therapeutic products, that contain information about the indications, usage, dosage, administration, combination therapy, contraindications and/or warnings concerning the use of such therapeutic products.

The term "paratope" refers to that part of a given antibody molecule that is required for specific binding between a target and a binding site. A paratope may be continuous, i.e. formed by adjacent amino acid residues present in the binding site, or discontinuous, i.e. formed by amino acid residues that are at different positions in the primary sequence of the amino acid residues, such as in the amino acid sequence of the CDRs of the amino acid residues, but in close proximity in the three-dimensional structure, which the binding site adopts.

The term "peptidic linker" denotes a linker of natural and/or synthetic origin. A peptidic linker consists of a linear chain of amino acids wherein the 20 naturally occurring amino acids are the monomeric building blocks which are connected by peptide bonds. The chain has a length of from 1 to 50 amino acid residues, preferred between 1 and 28 amino acid residues, especially preferred between 3 and 25 amino acid residues. The peptidic linker may contain repetitive amino acid sequences or sequences of naturally occurring polypeptides. The peptidic linker has the function to ensure that the domains of a circular fusion polypeptide can perform their biological activity by allowing the domains to fold correctly and to be presented properly. Preferably the peptidic linker is a "synthetic peptidic linker" that is designated to be rich in glycine, glutamine, and/or serine residues. These residues are arranged e.g. in small repetitive units of up to five amino acids, such as GGGS (SEQ ID NO: 58), GGGGS (SEQ ID NO: 59), QQQG (SEQ ID NO: 60), QQQQG (SEQ ID NO: 61), SSSG (SEQ ID NO: 62) or SSSSG (SEQ ID NO: 63). This small repetitive unit may be repeated for two to five times to form a multimeric unit, such as e.g. (GGGS)2 (SEQ ID NO: 64), (GGGS)3 (SEQ ID NO: 65), (GGGS)4 (SEQ ID NO: 66), (GGGS)5 (SEQ ID NO: 67), (GGGGS)2 (SEQ ID NO: 68), (GGGGS)3 (SEQ ID NO: 69), (GGGGS)4 (SEQ ID NO: 70), (GGGGS)4GG (SEQ ID NO: 73), GG(GGGGS)3 (SEQ ID NO: 72) and (GGGGS)6 (SEQ ID NO: 74). At the amino- and/or carboxy-terminal ends of the multimeric unit up to six additional arbitrary, naturally occurring amino acids may be added. Other synthetic peptidic linkers are composed of a single amino acid, that is repeated between 10 to 20 times and may comprise at the amino- and/or carboxy-terminal end up to six additional arbitrary, naturally occurring amino acids, such as e.g. serine in the linker GSSSSSSSSSSSSSSSG (SEQ ID NO: 71). All peptidic linkers can be encoded by a nucleic acid molecule and therefore can be recombinantly expressed. As the linkers are themselves peptides, the antifusogenic peptide is connected to the linker via a peptide bond that is formed between two amino acids.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "recombinant antibody", as used herein, denotes all antibodies (chimeric, humanized and human) that are prepared, expressed, created or isolated by recombinant means. This includes antibodies isolated from a host cell such as a NSO, HEK, BHK or CHO cell or from an animal (e.g. a mouse) that is transgenic for human immunoglobulin genes or antibodies expressed using a recombinant expression plasmid transfected into a host cell. Such recombinant antibodies have variable and constant regions in a rearranged form. The recombinant antibodies as reported herein can be subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein as reported herein are in one preferred embodiment "bivalent".

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "domain crossover" as used herein denotes that in a pair of an antibody heavy chain VH-CH1 fragment and its corresponding cognate antibody light chain, i.e. in an antibody binding arm (i.e. in the Fab fragment), the domain sequence deviates from the natural sequence in that at least one heavy chain domain is substituted by its corresponding light chain domain and vice versa. There are three general types of domain crossovers, (i) the crossover of the CH1 and the CL domains, which leads to domain crossover light chain with a VL-CH1 domain sequence and a domain crossover heavy chain fragment with a VH-CL domain sequence (or a full length antibody heavy chain with a VH-CL-hinge-CH2-CH3 domain sequence), (ii) the domain crossover of the VH and the VL domains, which leads to domain crossover light chain with a VH-CL domain sequence and a domain crossover heavy chain fragment with a VL-CH1 domain sequence, and (iii) the domain crossover of the complete light chain (VL-CL) and the complete VH-CH1 heavy chain fragment ("Fab crossover"), which leads to a domain crossover light chain with a VH-CH1 domain sequence and a domain crossover heavy chain fragment with a VL-CL domain sequence (all aforementioned domain sequences are indicated in N-terminal to C-terminal direction).

As used herein the term "replaced by each other" with respect to corresponding heavy and light chain domains refers to the aforementioned domain crossovers. As such, when CH1 and CL domains are "replaced by each other" it is referred to the domain crossover mentioned under item (i) and the resulting heavy and light chain domain sequence. Accordingly, when VH and VL are "replaced by each other" it is referred to the domain crossover mentioned under item (ii); and when the CH1 and CL domains are "replaced by each other" and the VH1 and VL domains are "replaced by each other" it is referred to the domain crossover mentioned under item (iii). Bispecific antibodies including domain crossovers are reported, e.g. in WO 2009/080251, WO 2009/080252, WO 2009/080253, WO 2009/080254 and Schaefer, W., et al, Proc. Natl. Acad. Sci USA 108 (2011) 11187-11192.

Multispecific antibody produced with a method as reported herein can also comprises Fab fragments including a domain crossover of the CH1 and the CL domains as mentioned under item (i) above, or a domain crossover of the VH and the VL domains as mentioned under item (ii) above. The Fab fragments specifically binding to the same antigen(s) are constructed to be of the same domain sequence. Hence, in case more than one Fab fragment with a domain crossover is contained in the multispecific antibody, said Fab fragment(s) specifically bind to the same antigen.

The term "binding site" as used herein denotes a polypeptide that can specifically bind to or can be specifically bound by a second polypeptide. In one embodiment the binding site is selected from the group of polypeptides consisting of an antibody heavy chain variable domain, an antibody light chain variable domain, a pair of an antibody heavy chain and an antibody light chain variable domains, a receptor or functional fragment thereof, a ligand or a functional fragment thereof, an enzyme or its substrate.

Gene Transfer

A receptor-mediated endocytosis process that results in the movement of receptors from the plasma membrane to the inside of the cell. The process begins when cell surface receptors are mono-ubiquitinated following ligand-induced activation. Receptors are subsequently taken up into endocytic vesicles from where they are either targeted to the lysosome or vacuole for degradation or recycled back to the plasma membrane.

Non-viral gene transfer as described in the present invention provides an alternative method of efficient gene delivery intended to result in lower levels of toxicity. The goal of non-viral gene therapy is mimicking the successful viral mechanisms for overcoming cellular barriers that block efficient expression of the target gene while minimizing the toxicities associated with gene delivery. The capabilities of a synthetic non-viral vector could include specific binding to the cell surface, entry, endosomal escape, translocation to the nucleus, and stable integration into the target cell genome.

The rate limiting step of non-viral gene delivery techniques is the transfer of encapsulated plasmids from the endosomes to the nucleus (Felgner, Sci. Am. 276 (1997) 102-106). In this setting, plasmids are endocytosed by cells into the endosomal compartment. The acidity of this compartment together with its nuclease activity, would be expected to rapidly degrade plasmids (Felgner, Sci. Am. 276 (1997) 102-106). Chloroquine is known to raise the acidic pH of endosomes, and is used in certain gene therapy protocols to promote endosomal release (Fritz et al., Hum. Gene Ther. 7 (1996) 1395-1404).

The present invention provides for non-viral gene transfer that overcomes the inherent disadvantages associated with chemical and physical methods, including DEAEdextran, polybrene and the mineral calcium phosphate, microinjection and electroporation. The present invention further is more useful than liposome gene transfer. While liposomal gene transfer has several advantages including lack of immunogenicity, ease of preparation, and the ability to package large DNA molecules, the ratio of liposome/DNA must be carefully controlled to circumvent the development of toxic aggregates. In addition, liposomes have a limited efficiency of delivery and gene expression, and they have potentially adverse interactions with negatively charged macromolecules.

Complex formation with DNA in protein and peptide gene transfer, i.e., polyplex formation (Feigner et al., Hum. Gene Ther. 8 (1997) 511-512), is mediated through electrostatic interactions between the positively charged lysine and arginine residues and the negatively charged phosphates in the DNA backbone (Sternberg et al., FEBS Lett. 356 (1994) 361-366). Examples of peptide gene transfer exploit the physiological cellular process of receptor-mediated endocytosis for internalization.

Receptor-mediated gene delivery constructs contain a receptor-binding ligand and a DNA-binding moiety, usually poly-L-lysine. Cells have been targeted using a number of different ligands including transferrin, asialoglycoprotein, immunoglobulins, insulin, the EGF receptor, and an integrin binding-peptide. DNA binding elements include protamines, histones H1, H2A, H3 and H4, poly-L-lysine, and cationic amphiphilic alpha-helical oligopeptides with repeated sequences (Niidome et al., J. Biol. Chem. 272 (1997) 15307-15312).

The potential advantages of protein/peptide gene transfer of the present invention include ease of use, production, and mutagenesis, purity, homogeneity, ability to target nucleic acids to specific cell types, cost effective large-scale manufacture, modular attachment of targeting ligands, and the lack of limitation on the size or type of the nucleic acid that can be delivered.

The critical step for efficient gene delivery is the formation of the polyplex; analyses on the interactions between proteins/peptides and plasmids including particle size, protein/peptide/DNA charge ratio, buffering medium, and the like are underway to optimize the conditions for polyplex formation (Adami et al., J. Pharm. Sci. 87 (1998) 678-683; Duguid et al., Biophys. J. 74 (1998) 2802-2814; Murphy et al., Proc. Natl. Acad. Sci. USA 95 (1998) 1517-1522; Wadhwa et al., Bioconjug. Chem. 8 (1997) 81-88). In contrast to the currently available methods of gene delivery which include calcium phosphate precipitation, DEAE dextran, electroporation, lipid systems, protein/peptide gene transfer involves the creation of a delivery vehicle whose properties can be predicted and controlled, and which could serve to enhance the activities required for the entry and persistent expression of exogenous nucleic acids. In addition, DNA condensation mediated via proteins/peptides stabilizes the polyplex during formulation and preserves its structure in serum, unlike many cationic liposomes (Adami et al., J. Pharm. Sci. 87 (1998) 678-683; Wilke et al., Gene Ther. 3 (1996) 1133-1142). Once active peptide motifs are identified, they can be combined to obtain a multifunctional complex with functions analogous to those of viral capsids.

DNA, larger in size than oligonucleotides, is not readily endocytosed and must therefore be packaged into a vehicle capable of efficient entry into cells (Bongartz et al., Nucleic Acids Res. 22 (1994) 4681-4688; Feigner, Sci. Am. 276 (1997) 102-106). The principal obstacle to cellular DNA uptake is charge (Feigner, Sci. Am. 276 (1997) 102-106). In an aqueous solution DNA has a net negative charge. DNA tends to be repelled from cell membranes, because they, too, are negatively charged. There are a few exceptions where cells appear to be able to assimilate naked DNA; this includes the successful target protein expression after direct muscular injections in mice (Blau and Springer, N. Engl. J. Med. 333 (1995) 1554-1556; Cohen, Science, 259 (1993) 1691-1692; Feigner, Sci. Am. 276 (1997) 102-106; Wolff et al., Science 247 (1990) 1465-1468). Most cells are quite resistant to transfection unless a carrier is used.

Compositions and Methods

Herein is reported a novel system for highly efficient and specific targeted gene delivery to and into cells. Plasmid DNA and core histones have been assembled to chromatin by salt gradient dialysis. To enable antibody mediated targeting of such 'plasmid-chromatin', bispecific antibody derivatives and chromatin were connected, e.g. via a nucleic acid binding peptide bridge. With such a composition/complex chromatin-assembled plasmid DNA can be targeted with high efficiency to cells.

It has been found that application of antibody-targeted plasmid-chromatin to cells in nM concentrations under normal intracellular culturing conditions enables intracellular delivery and nuclear (expression) functionality in >90% of cells. Targeting and transgene functionality was observed with absolute specificity and without detectable cytotoxicity for different cell lines and different antibody targets. Examples for targeted transgene delivery and intracellular functionality include reporter constructs as well as transgenes encoding CRISPR/Cas9 gene editing, demonstrating broad applicability of this targeted gene delivery approach.

Generation and Composition of Vehicles for Targeted Delivery of Large Nucleic Acids Applying Hapten-Binding bsAbs An exemplary, non-limiting overview of the entities applied as well as the process steps and of different options for generating delivery entities according to the current invention that enable specifically targeted and efficient intracellular delivery of large nucleic acids, such as plasmids, is provided in FIG. 1.

As the targeted delivery entities and methods as reported herein are especially suited for the delivery of large nucleic acids, such as e.g. expression plasmids, the following exemplary description is done using an expression plasmid. This shall not be construed as limiting the scope of the current invention. It is merely done to exemplify the invention. The true scope of the invention is set forth in the appended claims.

Plasmid DNA encoding the desired sequences, genes or expression cassettes were assembled with histones to form nucleosomes resulting in 'plasmid-chromatin'.

Thereafter, haptens were either attached by chemical conjugation of activated hapten reagents (such as NHS-hapten or maleimide-hapten or other hapten-derivatives) to nucleosomes as shown in the left panel 'A' of FIG. 1. Another method to attach haptens to nucleosome-plasmid complexes is shown in the right panel 'B' of FIG. 1. Here, haptenylated human peptides with DNA-binding functionality were added to nucleosome-assembled plasmids to form haptenylated plasmid-nucleosome-peptide complexes.

Finally, bispecific antibodies that recognize the used hapten as well as a cell surface antigen were added to the haptenylated plasmid-chromatin (haptenylated by A or B of FIG. 1). These bispecific antibodies become conjugated to the haptenylated plasmid nucleosomes by their hapten-binding moieties. The resulting bispecific antibody-plasmid-chromatin complexes comprise free binding entities of the second specificity of the bsAbs with a binding specificity for a target on the surface of target cells.

Histones are capable to highly compact DNA by wrapping the DNA double strand around a histone octamer. Histones may also contain sequences/domains that facilitate the cellular uptake (Wagstaff, K. M., et al. Mol. Ther. 15 (2007) 721-731; Rosenbluh, J. et al., J. Mol. Biol. 345 (2005) 387-400; Rosenbluh, J., et al., Biochim. Biophys. Acta 1664 (2004) 230-240; Wagstaff, K. M., et al., Faseb J. 22 (2008) 2232-2242). Histone-DNA complexes, i.e. nucleosomes or chromatin also possess a greatly reduced overall charge compared to negatively charged nucleic acids. Therefore, plasmid DNA was 'packaged' into nucleosomes/plasmid-chromatin to evaluate if size compression and reduction of negative charges is able to facilitate intracellular plasmid delivery, preferentially combined with cell- or tissue-specific delivery.

Assembly of Histones on DNA can be achieved efficiently by in vitro salt gradient dialysis in various scales.

Histone octamers assemble on DNA in a defined manner (about 147 base pairs are wrapped around one Octamer).

Successful formation of nucleosomes/plasmid chromatin results in a decreased overall charge of chromatin compared to histone alone (pos. charge) or plasmid DNA (neg. charge). Because nucleosome bound DNA is also protected against nucleases, nuclease resistance of plasmid DNA thus serves as another parameter by which to assess successful formation of plasmid chromatin.

It has been found that core histones can be efficiently assembled on DNA by salt gradient dialysis. This method is also applicable for supercoiled plasmid DNA to generate plasmid chromatin. This method has been applied to generate plasmid chromatin with an eGFP expression plasmid. As Histone octamers assemble on DNA in a highly defined manner (exactly 147 base pairs are wrapped around one Octamer) quality of chromatin can be analyzed by nuclease digest and subsequent agarose gel-electrophoresis. Nuclease digest of efficiently assembled chromatin generates DNA fragments of multiples of 147 base pairs for short digestion times indicating that more than one histone was assembled on one plasmid in close distance. Furthermore, DNA fragments shorter than 147 bp occur only in a minor fraction as at the utmost slightly visible in the late time-point.

The experimental evaluation of charge- and nuclease resistance of assembled plasmid chromatin is shown in FIG. 2 B (EMSA) and FIG. 2A (nuclease resistance assay).

The results of these analyses revealed successful generation of plasmid chromatin: EMSA assays (FIG. 2B) revealed slight retention, i.e. charge reduction of assembled chromatin compared to plasmid DNA alone. Nuclease sensitivity assays (FIG. 2A) also demonstrated that the plasmid DNA became nuclease resistant as indicated by DNA fragments of multiples of 147 base pairs. This indicated that more than one histone was assembled on one plasmid in close distance. Furthermore, DNA fragments shorter than 147 bp occurred only in a minor fraction (slightly visible at all time-points).

For the conjugation to the hapten different equally well working approaches are possible, such as:
(A) haptenylating chromatin by lysine side chain conjugation
(B) haptenylating chromatin by haptenylation of plasmid DNA prior to nucleosome assembly
(C) haptenylating chromatin by applying haptenylated histones for chromatin assembly.

For biotin as exemplary hapten the results obtained with each of these different approaches are shown in FIG. 3. FIG. 3A shows that after the chemical conjugation reaction plasmid-chromatin binds to streptavidin. This proves that biotin has been chemically attached to the plasmid-chromatin. FIG. 3B shows that the chemical conjugation of biotin to plasmid-DNA also results in biotinylated plasmid-chromatin, as represented by its capability to bind streptavidin. FIG. 3C shows successful complex formation using biotinylated histones in chromatin assembly reactions generate biotinylated plasmid-chromatin.

Previous work by Haas et al. (see, e.g., WO 2011/157715) identified nucleic acid-binding, positively charged human peptides derived from secreted human proteins (i.e. with proposed low immunogenicity in humans) (Haas, A. K. et al., Biochem. J. 442 (2012) 583-593). Some of those positively charged amphipathic peptides displayed the ability to traverse biological membranes, i.e. can be considered to be human Cell Penetrating Peptides (huCPPs). Other peptides contained the same amounts of positive charges, bound DNA, yet without CPP functionality.

To identify peptides suitable for attaching haptens to plasmid DNA, the plasmid-binding features of a subset of peptides described by Haas et al. as well as some mutated derivatives thereof has been analyzed. These included haptenylated (digoxigenylated) NRTN, ASM3B and CPXM2 (effective CPP functionality), WNT (no/low CPP functionality), FALL (low/no CPP functionality), and as references the TAT peptide (CPP), a DNA-binding peptide derived from p53, and a mutated FALL peptide containing histidine instead of lysine or arginine. A fusion peptide composed of NRTN combined with His-Fall was also included.

Interaction of peptides with plasmid DNA was analyzed by EMSA shift assay and/or by Microscale thermophoresis analyses (MST). Both technologies differentiate peptides that bind DNA from those that do not. The results of these experiments (FIG. 4A (EMSA), FIG. 4B (MST), the table below) indicate that several human peptides bind plasmid DNA and hence can be used to attach haptens to plasmid DNA. These include peptides derived from human P53, NRTN, FALL, CPXM2, WNT, ASM3B and derivatives thereof.

| Peptide Name | DNA binding | known CPP functionality |
|---|---|---|
| P53 | +++ | ? |
| WNT | + | − |
| NRTN | + | +++ |
| FALL | +++ | ++ |
| CPXM2 | +++ | ++ |
| HisFALL | − | ? |
| TAT | + | + |
| ASM3B | + | ++ |
| HisFALL-NRTN | + | ? |

Also haptenylated DNA-binding peptides can be attached to plasmid-chromatin. This leads to incorporation of the peptide-bound hapten into plasmid-nucleosomes.

One exemplary peptide that has been used to show this approach was the human cell penetrating peptide CPXM2. This peptide captures plasmid-chromatin via charge interaction with the negatively charged DNA backbone. Successful incorporation of hapten (in this case biotin) into plasmid-chromatin was demonstrated above. FIG. 5 shows in biolayer interferometry (Octet) analyses that biotinylated peptides bind to plasmid-chromatin, enabling it to bind to streptavidin. FIG. 5 demonstrates biotinylation of plasmid-chromatin by attachment of the bio-CPXM2 peptide.

The human protein derived and nucleic acid binding peptide CPXM2 identified by Haas et al. can be used as an exemplary molecule to capture plasmid DNA or chromatin via charge interaction with the negatively charged DNA backbone (Haas, A. K., et al., Biochem. J. 442 (2012) 583-593). To enable binding of CPXM2 peptide to antibodies, a haptenylated, e.g. biotinylated, variant of CPXM2 peptide and hapten, i.e. biotin in this example, binding bispecific antibodies were used. Affinity of antibody-peptide constructs to chromatin was measured by microscale thermophoresis (MST). With this method affinity data was generated in solution without the need to capture antibody or peptide as this would affect affinity in this system due to avidity effects. To identify the most suitable antibody format, monovalent biotin binding triFabs were compared with bivalent biotin binding bispecific antibodies towards affinity and potential aggregation due to crosslinking of the molecules (Mayer, K., et al., Int. J. Mol. Sci. 16 (2015) 27497-27507; Schneider, B., et al., Mol. Ther. Nucleic Acids 1 (2012) e46). Affinity of monovalent anti biotin triFab~biotin CPXM2 constructs to chromatin was in the 3 digits nanomolar range (300 nM). The bivalent anti biotin bispecific antibody~biotin CPXM2 constructs demonstrated further stabilization (to 2 digits nM affinity) without being bound by this theory most likely due to avidity effects as two CPXM2 peptides can be bound by one antibody. No aggregation was observed with both antibody-peptide constructs indicating that no crosslinking occurs with both antibody formats. Specificity was proven by respective controls without peptide. The MST data set is summarized in the following Table.

| Construct | KD [nM] | SEM [nM] |
|---|---|---|
| Chromatin + bio-CPXM2~monovalent anti bio bsAb | 300 | 36 |
| Chromatin + bio-CPXM2~bivalent anti bio bsAb | 73.1 | 3.4 |
| Chromatin + monovalent anti bio bsAb only | No interaction | N.A. |
| Chromatin + bivalent anti bio bsAb only | No interaction | N.A. |

Interaction between chromatin, peptide and antibody was verified by the Octet system. As the strongest interaction was observed when the peptide was coupled to the bivalent bispecific antibody format this system has been used for further studies. As the antibody peptide construct interacts with the negatively charged DNA backbone, it had been checked whether this interaction alters nuclease resistance of plasmid chromatin after antibody-peptide assembly. After incubation of chromatin with antibody and peptide with subsequent nuclease digestion, the pattern of digested DNA after 270 seconds was similar to the pattern of nuclease treated chromatin alone after 20 seconds. This data clearly demonstrates that with formation of the targeted chromatin complex plasmid DNA is further protected against nucleases.

BsAbs that bind cell surface antigens as well as haptens have previously been described to capture haptenylated payloads and form antibody-payload complexes (see e.g. WO 2011/003780; Schneider, B. et al., Mol. Ther. Nucleic Acids 1 (2012) e46; Dengl, S., et al., Immunol. Rev. 270 (2016) 165-177).

The above described simple and robust charging reaction was used to couple biotinylated plasmid-chromatin to bsAbs that bind biotin as well as antigens present on surface of cancer cells, such as LeY or CD33. This involved incubation of biotinylated plasmid-chromatin and bsAb in a 4-to-25 ratio for 30 min at 25° C. Beside antigens present on cancer cells any other antigen, which is specific for a certain subpopulation of cells, can be used. Especially preferred are internalizing cell surface receptors.

The assembly reaction of bsAb and haptenylated plasmid-chromatin was monitored by SPR analyses (ForteBio Octet) as shown in FIG. 6. Therefore, anti-Ley/biotin bispecific antibodies (bio-bsAbs (LeY-Bio)) were captured on protein A dips, subsequently assessing the binding of added biotinylated plasmid-chromatin to biotin-binding bsAbs.

FIG. 6A shows complex formation of the binding of bsAbs to plasmid-chromatin that was biotinylated by chemical conjugation lysine side chains of chromatin.

FIG. 6B shows complex formation of the binding of bsAbs to plasmid-chromatin that was biotinylated by chemical conjugation of plasmid DNA prior to chromatin assembly.

FIG. 6C shows complex formation of the binding to biotinylated plasmid-chromatin that was obtained by adding biotinylated DNA-binding peptides to plasmid-chromatin.

FIG. 6D shows complex formation of the binding to digoxigenylated plasmid-chromatin that was obtained by adding digoxigenylated DNA-binding peptides to plasmid-chromatin. In this example anti-Dig-bsAbs (LeY-Dig) were captured on Protein A dips.

Antibody-mediated targeting of bsAb-DNA complexes and bsAb-chromatin complexes was demonstrated on cells that carry the target antigen recognized by the respective bsAb. Therefore, bsAbs that simultaneously bind the LeY antigen and digoxigenin or that bind the LeY antigen and biotin were used in combination with LeY-expressing MCF7 breast cancer cells.

Thus, in addition to specific formation and prolonged nuclease resistance of the antibody-chromatin complex, DNA delivery to the cell surface via the associated antibodies has been determined. To determine delivery efficacy and specificity, antibodies with specificity against Lewis Y or CD33 in addition to the specificity against biotin were compared on MCF7 cells (LeY+++/CD33-). Furthermore, plasmid DNA labelled with Cy5 fluorophore was used to enable quantification of plasmid DNA on cells by flow cytometry one hour after cell treatment. To elaborate the influence of chromatin assembly on delivery specificity and efficacy, the delivery system for plasmid DNA was applied before and after chromatin assembly. FIG. 14 shows Cy5 signal of MCF7 cells after treatment with plasmid DNA before chromatin assembly complexed with anti LeY (dotted red, right peak) and anti CD33 (dotted blue, left peak) antibody. A distinct fluorescence signal was detected after treatment with anti LeY-DNA-Cy5 complexes demonstrating that DNA delivery is highly efficient. In contrast anti CD33-DNA-Cy5 complexes did not result in Cy5 positive cells proving that DNA delivery is specific and exclusively targeting antibody mediated. After chromatin assembly plasmid DNA delivery efficacy and specificity was not affected as the same distinct fluorescence signal was observed after treatment with anti LeY-chromatin-Cy5 complexes (FIG. 15, solid red, right peak) and no Cy5 signal was detected with anti CD33-chromatin-Cy5 complexes (FIG. 15, solid blue, right peak). To confirm the presence of the antibody in our delivery system, we used anti CD33 and anti LeY antibodies labelled with Cy3 fluorophore together with Cy5 labelled chromatin. As displayed in FIG. 16, MCF7 cells treated with anti CD33-Cy3-chromatin-Cy5 complexes did not show an elevated Cy5 as well as Cy3 signal (blue contours, lower left quadrant) demonstrating that neither antibody nor chromatin is present at the cell surface. In contrast, anti LeY-Cy3-chromatin-Cy5 treatment results in distinct fluorescence signals for Cy3 and Cy5 (FIG. 16, red contours, spanning lower and upper right quadrant), proving antibody at the cell surface and confirming the successful delivery of chromatin. Finally, the second specificity of the targeting antibody against biotin was checked. Therefore, the targeted chromatin delivery system comprising biotinylated-CPXM2 peptide was compared with a targeting system where the biotinylated peptide was exchanged against a peptide with the wrong hapten (digoxigenin). FIG. 16 highlights that both complexes (blue contours in the lower left quadrant with biotin-CPXM2 and green contours in the lower right quadrant with digoxigenin-CPXM2) generate a distinct Cy3 fluorescent signal on MCF7 cells, whereas Cy5 signal was only detected after treatment with biotin-CPXM2 comprising complexes. This clearly demonstrated that despite the cell surface specificity, also the second specificity against the hapten is necessary for chromatin and therefore plasmid DNA delivery. Note the lack of non-specific interaction between antibody and peptide/chromatin.

To analyze targeted delivery of plasmids (without nucleosome/chromatin assembly), a GFP encoding plasmid labelled with Cy5 was incubated in PBS for 1 h with a digoxigenin-labeled peptide (CPXM2) followed by incubation with bispecific anti-LeY/digoxigenin antibody for 30 min. Samples were added to MCF7 cells seeded in an 8-well chamber slide at a final concentration of 4 µg/mL plasmid DNA, 250 nM peptide and 125 nM antibody. Cells were thereafter imaged with a confocal microscope after 1 h, 4 h, 24 h and 48 h.

The results of these analyses are shown in FIG. 7. It can be seen that plasmid DNA was efficiently delivered to MCF7 cells as indicated by internalization of DNA. At early time-points, antibody and DNA is mainly located at the cell surface. At later time-points DNA was found internalized in vesicular compartments.

To analyze bsAb-targeted delivery of haptenylated plasmid-chromatin, complexes of LeY-Dig bsAbs and a GFP encoding Cy5-labeled plasmid assembled to dig-chromatin generated via peptide attachment as described above were added on MCF7 cells. Those cells were seeded in an 8-well chamber slide at a final concentration of complexes containing chromatin harboring 4 µg/mL plasmid DNA assembled to plasmid chromatin, 250 nM peptide and 125 nM antibody. Cells were thereafter imaged with a confocal microscope after 1 h, 4 h, 24 h and 48 h, detecting plasmid-chromatin via Cy5 signals.

The results of these analyses show that plasmid DNA was efficiently delivered to MCF7 cells as indicated by the Cy5 signal of plasmid-chromatin on the cells. At early time-points, antibody and plasmid-chromatin is mainly located at the cell surface. At later time-points plasmid-chromatin was found internalized in vesicular compartments and GFP reporter gene expression was detected indicating that plasmid DNA is also present in the nucleus (FIG. 7, 48 h).

As a control, an anti-CD33/digoxygenin bsAbs was also attached and added to CD33-negative MCF7 cells. With this combination, i.e. without the respective cell surface receptor the plasmid/chromatin was not delivered into cells, proving that targeted delivery is due to the specific binding of the bsAbs to cell surface antigens.

The antibody-mediated targeting of bispecific antibody-DNA complexes enables the uptake thereof into cells. Subsequently, intracellular presence of delivered plasmids enables transient expression (as shown in the examples), or upon integration stable expression and/or functionality.

This has been shown by exposing LeY-expressing MCF7 breast cancer cells to bsAbs that simultaneously bind the LeY antigen and digoxigenin, complexed with plasmids that were digoxigenylated by attachment of dig-peptides (dig-NRTN). As a control for specific targeting, plasmids were complexed in separate experiments to dig-binding bsAbs that recognize the CD33 antigen which is absent on MCF7 cells.

Intracellular uptake and functionality was shown by detecting expression of GFP, which is encoded on an expression cassette within the delivered plasmid, inside the MCF7 cells.

The delivery complexes were generated, applied to MCF7 cells followed by fluorescence microscope imaging of the treated cells. The results of these analyses are shown in FIG. 8. Imaging fluorescence microscopy revealed complete absence of fluorescence in cell populations treated with non-targeting CD33-bsAb-plasmid complexes. In contrast, cells that expressed GFP were detectable in the LeY+++/CD33-MCF7 cells that received with the cell surface targeting LeY-bsAb-plasmid complexes. Treatment with the complex containing the antibody against the cell surface antigen LeY showed unambiguously single GFP expressing cells (~2% of the population, left panel) while cells treated with the complex containing the antibody against CD33 (right panel) did not show any GFP expression above background. Thus, bsAb-targeted specific delivery and accumulation of haptenylated peptide-DNA complexes enables productive uptake into the cytoplasm/nucleus of cells leading to GFP expression to some extent.

Antibody-mediated targeting of bispecific antibody-plasmid-chromatin complexes enables uptake into cells and subsequently intracellular functionality of delivered bsAb-chromatin complexes.

This has experimentally been shown by exposing LeY-expressing MCF7 breast cancer cells to bsAbs that simultaneously bind the LeY antigen and digoxigenin, complexed with plasmid-chromatin assemblies that were digoxigenylated by attachment of dig-peptides (e.g. digoxigenylated CPXM2, p53 and others. As a control for specific targeting, plasmid-chromatin was complexed in separate experiments to Dig-binding bsAbs that recognize the CD33 antigen which is absent on MCF7 cells.

An overview of the experimental setup and generation of delivery vehicles is shown in FIG. 9A.

Intracellular uptake and functionality (transcription and translation of the encoded GFP mRNA) was assessed by detecting and quantifying GFP expressing cells in FACS analyses.

Delivery complexes were generated by incubating haptenylated plasmid-chromatin (harboring GFP expression plasmids) with bispecific LeY-hapten-binding bsAbs. Two different bsAb-formats were used. The first format applied was the TriFab format described by Mayer et al. (Mayer, K. et al., Int. J. Mol. Sci. 16 (2015) 27497-27507). This bsAb harbors two cell surface binding sites and one hapten binding site. The second format was a tetravalent IgG-derivative which harbors two cell surface binding sites and two hapten binding sites (see e.g. WO 2011/003780; Schneider, B. et al., Mol. Ther. Nucleic Acids 1 (2012) e46; Killian, T. et al., Sci. Rep. 7 (2017) 15480). To evaluate intracellular delivery and functionality, the bsAb-hapten-plasmid-chromatin complexes were added to MCF7 cells seeded in a 12-well plate to a final concentration of 8 µg/mL plasmid-DNA (assembled to chromatin via addition of digoxigenylated DNA-binding peptides), 500 nM peptide and 250 nM antibody.

Intracellular activity was addressed by treatment of MCF7 cells and quantification of eGFP plasmid expression by flow cytometry 48 h after treatment. The results of these analyses are shown in FIGS. 9B-E.

After Chromatin treatment without peptide and antibody, no GFP expressing cells were detected. Furthermore, treatment with Chromatin complexes comprising a triple Fab that does not bind at the cell surface (anti-CD33) also did not generate GFP expressing MCF7 cells. Targeted delivery of DNA not assembled into Chromatin by cell surface binding triple Fab (anti LeY) resulted in about 0.5% fluorescent cells. In contrast, the targeted Chromatin construct showed GFP delivery efficacy stronger than the PEI transfection positive control (FIG. 9B). The use of bispecific antibodies with bivalent hapten binding instead of triple Fabs with one valency against the hapten further improves delivery efficiency without reduction of specificity (0% GFP positive cells) (FIG. 9C). Chromatin can be delivered by attaching haptens to chromatin via peptides of different sequences.

FIG. 9D shows that productive delivery into cells is not strictly dependent on peptide identity as different peptides, incl. CPXM2 and P53-derived peptides and others can be applied to attach haptens for targeted intracellular delivery.

Plasmid-chromatin that to which haptens are attached via chemical conjugation can also be specifically delivered to and into MCF7 target cells and result in GFP expression as shown in FIG. 9F.

The entities according to the current invention can be constructed with histone of different sources. This includes recombinant human histones as well as histones isolated from natural sources, such as, e.g., histones from calf thymus or from chicken erythrocytes. In consequence, histones of different sources have been used for plasmid-chromatin assembly in the examples provided herewith to demonstrate that the herein reported delivery system is generally applicable and not restricted to the use of particular histones. Therefore, targeted-delivery entities were assembled using histones of different sources. The results are shown in FIG. 10.

FIG. 10A shows that Histones from chicken erythrocytes (which also contains histone H1 that is absent in the other histone sources) enabled targeted specific intracellular delivery of GFP expression plasmids.

FIG. 10B shows that unmodified human recombinant histones showed delivery efficiency comparable to calf thymus histones. Biotinylated versions of human recombinant histones can also be used to assemble complexes that enable targeted specific intracellular delivery of GFP expression plasmids. Quality analyses of the assembled chromatin showed that biotinylation of histone H3 affects chromatin assembly resulting in plasmid chromatin of lower quality (FIG. 10C). The correlation of chromatin quality and delivery efficacy demonstrates that proper histone assembly is the pre-requisite for functional intracellular delivery of the composition as reported herein.

In one embodiment the histone is recombinant human histone or calf thymus histone. In one embodiment the recombinant human histone is not modified, i.e. it is not chemically derivatized.

Another example for intracellular delivery and activity of large nucleic acids is the targeted delivery of CRISPR components encoded on plasmids to the cell nucleus. Therefore, the GFP expression cassette was replaced by expression cassettes encoding CRISPR/Cas9 components that address the human DPH1 gene. It has previously been described that gene-editing mediated inactivation of DPH1, combined with assessment of cellular sensitivity towards Diphtheria Toxin (DT), can be used to quantify efficacy of gene editing (WO 2018/060238; Killian, T. et al., Sci. Rep. 7 (2017) 15480). It is essential for CRISPR-mediated gene editing that the encoding expression plasmids enter cells and become expressed at sufficient levels. Inactivation of all cellular copies of DPH1 (as consequence of gene editing) in turn renders cells resistant to DT. This generates a very robust readout which can be quantified by counting DT-resistant colonies following gene editing.

To assess targeted intracellular delivery of CRISPR/Cas9, gRNA against DPH1 and Cas9 nuclease encoding plasmids were used. Subsequently, efficiency of intracellular delivery and expression of the editing components was assessed by exposing cells to DT and subsequent determination of DT-resistant colonies as previously described by Killian et al. (Killian, T. et al., Sci. Rep. 7 (2017) 15480; WO 2018/060238). The results are shown in FIG. 11.

FIG. 11 shows that plasmids that encode CRISPR/Cas9 entities become specifically targeted and elicit effective intracellular expression upon delivery as antibody-targeted plasmid-chromatin. Plasmid chromatin that becomes targeted by antibodies to the surface of cells leads to a high degree of cells in which the target gene is edited/inactivated (high colony number of DT-resistant cells). In contrast, intracellular delivery and CRISPR/Cas9-mediated editing is not observed in cells that received plasmid-chromatin that was not targeted to cells.

Thus, with the complexes according to the current invention efficient on cell delivery and specificity as well as high nuclear delivery efficacy (as quantified by GFP reporter gene expressing cells with flow cytometry) can be achieved.

With the quantification by GFP reporter gene expressing cells with flow cytometry it is also possible to directly depict the influence of chromatin assembly on intracellular plasmid DNA delivery as only on cell DNA delivery is equally efficient with and without chromatin assembly. To address reporter gene expression MCF7 cell were treated with various complexes for 48 hours and subsequently GFP expressing cells were identified via flow cytometry. The ratio of GFP positive cells was determined by comparison with respective vehicle or antibody only control. Incubation of MCF7 cells in presence of DNA or chromatin did not generate cells expressing detectable levels of GFP, indicating no unspecific uptake of plasmid DNA before and after chromatin assembly. Moreover, association of antibody-peptide constructs does also not generate GFP positive cells when the antibody does not bind the cell surface as shown for anti CD33-DNA as well as anti CD33-chromatin complexes (see FIGS. 14 to 16; no unspecific uptake of antibody-DNA and antibody-chromatin was detected). Targeting of plasmid DNA by associated antibody-peptide constructs does generate single GFP positive cells (as observed under the microscope) but not to a significant extent despite efficient delivery to the cell surface as shown in FIG. 14. In contrast, the same antibody-peptide constructs now targeting chromatin raises the ratio of GFP positive cells from single exceptions to the vast major population (more than 90% positive cells). Finally, Lipofection was used as a positive control, resulting in about 60% reporter gene expressing cells.

Next, the cytotoxicity of the different treatments was measured by LDH release relative to vehicle control and complete cell lysis. Lipofection mediated cytotoxicity to a certain extent (about 15% to lysis control), usual for most transfection reagents. None of the other treatments showed detectable cytotoxic effects.

Thus, the impact of chromatin assembly on functional plasmid DNA delivery was surprisingly high.

Following the intracellular distribution of antibody and DNA after treatment with different complexes was assessed by confocal microscopy. FIG. 7 highlights the distribution of antibody-Cy3 (green) and DNA-Cy5 (red) in living cells 4 hours after treatment with targeted (LeY-) chromatin, targeted (LeY-) DNA or untargeted (CD33-) chromatin. Antibody as well as DNA was present at the cell surface as well as the vesicular system after targeting of chromatin as well as DNA. Overlay of both fluorescence signals indicates that most of antibody and DNA is co-localized and not separated. These data clearly demonstrate that targeted DNA gets delivered to the cell surface and internalized via the targeting antibody with as well as without chromatin assembly. Specificity of the targeting system was confirmed by confocal microscopy of MCF7 cells after incubation with the untargeted chromatin complex, as neither antibody nor DNA was detected at the cell surface as well as inside vesicles. Further, chromatin targeting does not only result in strong DNA accumulation at the cell surface and inside the vesicular system (cyan) but also in GFP expression (green). For imaging of GFP signal after 3 days, unlabeled antibody was used as labelling reduced chromatin delivery efficacy. To visualize the antibody in a more detailed imaging, cells were fixed and the antibody was counterstained with anti-human IgG Cy3 antibody. Accumulation of antibody (red) as well as DNA (pseudo color representation) inside the vesicular system was confirmed.

It has also been addressed if chromatin delivery can be applied with plasmid DNA of larger size and with more complex function. Therefore, a plasmid encoding a CRISPR/Cas9 knock-out system against Diphthamide synthesis gene 1 (DPH1) was used in combination with the previously published Diphtheria toxin (DT) based assay for quantification of CRISPR/Cas9 mediated gene editing (Killian, T., et al., Sci. Rep. 7 (2017) 15480). This assay utilizes DT resistance mediated by homozygous DPH1 knock-out for identification of cell clones were gene editing by Cas9 was successful. So only cells were DPH1 was knocked out homozygous survive and display colony formation after 2 weeks of continuous DT selection. First of all, the chromatin assembly on the DPH1 gRNA Cas9 expression plasmid was transferred and thereby it was demonstrated that assembly conditions are suitable to generate high quality chromatin independent of the plasmid. Afterwards this chromatin was used for delivery of Cas9 DPH1 gRNA encoding plasmid in the same manner as for the GFP expression plasmid as outlined above. After treatment of MCF7 cells with targeted (LeY-) Cas9 DPH1 gRNA chromatin, untargeted (CD33-) Cas9 DPH1 gRNA chromatin and targeted (LeY-) GFP chromatin and incubation for 3 days, cells were exposed to DT for two weeks. Finally, cells were fixed and colonies were counted under the microscope. The ratio of colony number and number of initially seeded cells is displayed as percentage of DT resistant clones and therefore percentage of clones with homozygous gene knock-out. Targeted delivery of Cas9 DPH1 gRNA chromatin results in almost 4% DT resistant clones whereas targeted delivery of GFP control chromatin does not result in any resistant colony, confirming that colony formation can only occur by expression of the CRISPR/Cas9 editing system. In line with the specificity of the chromatin targeting system as shown above for GFP, MCF7 treatment with untargeted (CD33-) Cas9 DPH1 gRNA chromatin does also not result in formation of DT resistant colonies. If compared with the determined absolute CRISPR/Cas9 knock-out frequency from the previous experiments, the determined percentage of DT resistant clones is equal to more than 60% of Cas9 expressing cells.

DISCUSSION

The development of a targeted gene delivery system faces multiple challenges as it must overcome several hurdles and therefore needs well-balanced properties (Ibraheem, D., et al., Int. J. Pharm. 459 (2014) 70-83; Mann, A., et al., Mol. Pharm. 11 (2014) 683-696). For example, a DNA delivery system must have affinity to the target cells to efficiently mediate the uptake of DNA but in parallel must not interact with serum components or the cell membrane of other cells and tissues to minimize loss of DNA and avoid off-target effects along the delivery route (Moffatt, S., et al., Gene Ther. 13 (2006) 761-772; Schatzlein, A. G., J. Biomed. Biotechnol. (2003) 149-158; Varkouhi, A. K., et al., J. Cont. Rel. 151 (2011) 220-228). Furthermore, DNA has to be translocated over the membrane barrier to enter the cytosol and finally reach the nucleus to enable transgene expression (Cervia, L. D., et al., PLoS One 12 (2017) e0171699; Sanders, N., et al., Adv. Drug Deliv. Rev. 61 (2009) 115-127). So the required membrane interaction for DNA translocation has to be efficient but at the same time gentle enough to avoid cell cytotoxicity.

These requirements are fulfilled by the composition according to the current invention. It is presented a highly flexible and modular gene delivery system. It could be demonstrated that the plasmid DNA uptake is solely mediated by the antibody-antigen interaction at the targeted cell surface. This means that, in contrast to other delivery systems just with preference to the target cells, the composition according to the invention provides for a system with absolute specificity with activity in the presence of serum components (cf. Wolff, J. A. and Rozema, D. B., Mol. Ther. 16 (2008) 8-15; McCaskill, J., et al., Mol. Ther. Nucleic Acids 2 (2013) e96; Novo, L., et al., Exp. Opin. Drug Deliv. 12 (2015) 507-512).

The composition according to the current invention mediates nuclear plasmid DNA delivery in over 90% of treated cells without cytotoxicity. Thus, it is provided a mechanism for efficient but gentle DNA membrane translocation comparable to optimized viral delivery systems (cf. Munch, R. C., et al., Mol. Ther. 21 (2013) 109-118; Veldwijk, M. R., et al., Cancer Gene Ther. 7 (2000) 597-604).

Moreover, the data generated with the composition according to the current invention clearly show that the essential component facilitating DNA membrane translocation is the organization of plasmid DNA into plasmid chromatin. Although it is possible to deliver plasmid DNA with and without chromatin assembly to target cells with comparable efficiency and specificity, only correctly assembled (and thereby functional) plasmid chromatin mediates high ratios of transgene expressing cells. Thus and in contrast to previous observations, histone assembly does not affect DNA uptake by unspecific membrane binding and but plasmid chromatin facilitates membrane translocation and nuclear DNA transport without the need for engineering of histone subunits (cf. Wagstaff, K. M., et al., Mol. Ther. 15 (2007) 721-731 and FASEB J. 22 (2008) 2232-2242). Additionally, no major differences in antibody mediated DNA or chromatin cell surface binding was observed.

Remarkably, despite being non-toxic, flexible, highly potent and specific, the gene delivery system, i.e. the composition, according to the current invention exclusively consists of proteins and peptides of mammalian origin. Thus, concerns about safety and the risk of immunogenicity of compounds of bacterial or viral origin are expected to be rather low.

In conclusion, herein is reported a novel system to deliver plasmid DNA with viral-based-system-like efficiency and absolute specificity exclusively by mammalian entities without toxicity. In addition, the composition according to the invention allows to expand targeted DNA delivery from reporter gene expression to therapeutically relevant systems, like e.g. CRISPR/Cas9.

The results of the experiments presented hereinabove and blow show that bsAb-targeted delivery of plasmid-chromatin enables very effective intracellular delivery of large nucleic acids. This delivery system enables efficacies (GFP-expressing cells) of up to >80%, i.e. comparable in efficacy to viral transfections and better than most nanoparticle/transfection approaches.

Comparative Example

The influence of proper plasmid-chromatin assembly on targeted intracellular delivery efficiency has been examined.

To address the question, whether improper chromatin assembly with irregular or unspecific histone binding influences functionality, modified histones have been used for assembly, whereby the modification(s) influence chromatin formation. Performing the assembly reaction under the same conditions as outlined above for the composition according to the invention, the sample with modified histones has a reduced quality of plasmid chromatin compared to the sample with unmodified histones (see FIG. 12). Comparison of both chromatin qualities on targeted delivery clearly demonstrates that proper assembly is important for delivery efficiency as chromatin with reduced quality is only half as potent as high quality chromatin (see FIG. 13).

Specific Embodiments

1. A composition for the targeted delivery of large nucleic acids to the nucleus of a eukaryotic cell comprising
   a histone (one or more histone polypeptides),
   a large nucleic acid,
   a hapten, and
   a bispecific binder that has a first binding specificity to the hapten and a second binding specificity to a cell-surface target present on the eukaryotic cell (a bispecific binder that has a first binding site specifically binding to the hapten and a second binding site specifically binding to a (cell-surface) target present on the eukaryotic cell),
   wherein
   the histone and/or the nucleic acid is/are covalently bound/conjugated to the hapten,
   the histone and the large nucleic acid are associated (non-covalently) with each other/form a non-covalent complex/form a nucleosome, and
   the hapten and the bispecific binder are associated with each other/bound to each other by the first binding specificity of the bispecific binder.
2. The composition according to embodiment 1, wherein the composition comprises a sufficient number of histone polypeptides in order to assemble the large nucleic acid into one or more nucleosomes.
3. The composition according to any one of embodiments 1 to 2, wherein at most/approximately/about 1 nucleosome per 150 bp of large nucleic acid DNA/plasmid DNA.
4. The composition according to any one of embodiments 1 to 2, wherein the composition comprises about 8 histone polypeptide per at most 150 bp of the large nucleic acid/1 nucleosome per at most 150 bp of the large nucleic acid
5. The composition according to any one of embodiments 1 to 4, wherein the histone is (one or more histone polypeptides are) a mixture of histone H2A, H2B, H3 and H4 (polypeptides).
6. The composition according to any one of embodiments 1 to 5, wherein the histone polypeptides are calf thymus histones, chicken erythrocyte histones, recombinant human histones, or mixtures thereof.
7. The composition according to any one of embodiments 1 to 6, wherein the histone is (one or more histone polypeptides are) recombinant human histone (polypeptides).
8. The composition according to embodiment 7, wherein the recombinant human histone polypeptide(s) is(are) not chemically derivatized or conjugated to a hapten.
9. The composition according to any one of embodiments 1 to 6, wherein the histone is (one or more histone polypeptides are) calf thymus histone (polypeptides).
10. The composition according to any one of embodiments 1 to 9, wherein the histone is (one or more histone polypeptides are) a mixture of histone H2A and histone H3 (polypeptides).
11. The composition according to any one of embodiments 1 to 10, wherein the histone (polypeptide) is recombinant human histone H3.
12. The composition according to embodiment 11, wherein the recombinant human histone (polypeptide) is recombinant human histone 3.1 or 3.3.
13. The composition according to any one of embodiments 1 to 12, wherein
    i) human histone H2A has the amino acid sequence of SEQ ID NO: 01,
    ii) bovine histone H2A has the amino acid sequence of SEQ ID NO: 02,
    iii) chicken histone H2A has the amino acid sequence of SEQ ID NO: 03,
    iv) human histone H2B has the amino acid sequence of SEQ ID NO: 04,
    v) bovine histone H2B has the amino acid sequence of SEQ ID NO: 05,
    vi) chicken histone H2B has the amino acid sequence of SEQ ID NO: 06,
    vii) human histone H3.1 has the amino acid sequence of SEQ ID NO: 07,
    viii) human histone H3.3 has the amino acid sequence of SEQ ID NO: 08,
    ix) bovine histone H3.3 has the amino acid sequence of SEQ ID NO: 09,
    x) chicken histone H3.3 has the amino acid sequence of SEQ ID NO: 10,
    xi) human histone H4 has the amino acid sequence of SEQ ID NO: 11,
    xii) bovine histone H4 has the amino acid sequence of SEQ ID NO: 12,
    xiii) chicken histone H4 has the amino acid sequence of SEQ ID NO: 13.
14. The composition according to any one of embodiments 1 to 13, wherein the large nucleic acid is one large nucleic acid molecule.
15. The composition according to any one of embodiments 1 to 14, wherein the large nucleic acid is selected from an expression plasmid comprising at least one expression cassette.
16. The composition according to any one of embodiments 1 to 15, wherein the large nucleic acid comprises between 1,000 and 100,000 nucleotides or base pairs.
17. The composition according to embodiment 16, wherein the large nucleic acid comprises between 1,250 and 20,000 nucleotides or base pairs.
18. The composition according to any one of embodiments 16 to 17, wherein the large nucleic acid comprises between 1,500 and 10,000 nucleotides or base pairs.
19. The composition according to any one of embodiments 1 to 18, wherein the histone is calf thymus histone and the composition comprises about 2 µg histone per µg large nucleic acid.
20. The composition according to any one of embodiments 1 to 18, wherein the histone is recombinant human histone and the composition comprises about 0.8-1 µg histone per µg large nucleic acid.

21. The composition according to any one of embodiments 1 to 18, wherein the histone is chicken erythrocyte histone and the composition comprises about 1 histone per μg large nucleic acid.
22. The composition according to any one of embodiments 1 to 21, wherein the composition comprises at least one hapten molecule.
23. The composition according to any one of embodiments 1 to 22, wherein the composition comprises two or more hapten molecules and the two or more hapten molecules are the same hapten molecule or different hapten molecules.
24. The composition according to any one of embodiments 1 to 23, wherein the hapten is selected from biotin, digoxygenin, theophylline, bromodeoxyuridine, fluorescein, DOTAM and helicar motif polypeptides.
25. The composition according to any one of embodiments 1 to 24, wherein the hapten is chemically conjugated to the (one or more) histone (polypeptides) or large nucleic acid.
26. The composition according to any one of embodiments 1 to 24, wherein the hapten is conjugated to a DNA binding peptide which is attached to the large nucleic acid.
27. The composition according to any one of embodiments 1 to 26, wherein each histone polypeptide is conjugated to a single hapten molecule and/or the large nucleic acid molecule is conjugated to at least one hapten molecule.
28. The composition according to any one of embodiments 1 to 27, wherein the bispecific binder is selected from a bispecific antibody, a bispecific scaffold, a bispecific peptide, a bispecific aptamer, a bispecific low-molecular-weight-structure.
29. The composition according to any one of embodiments 1 to 28, wherein the bispecific binder is selected from a bispecific full-length antibody, a bispecific CrossMab, a bispecific T-cell bispecific, a DAF, and a DutaMab.
30. The composition according to any one of embodiments 1 to 29, wherein the bispecific binder is a bispecific binder fragment.
31. The composition according to any one of embodiments 1 to 30, wherein the bispecific binder fragment is selected from a DutaFab, a F(ab')2, tandem scFv, diabody, tandAb, scFv2-CH1/CL, and VHH2-CH1/CL.
32. The composition according to any one of embodiments 1 to 31, wherein the (cell-surface) target is an internalizing cell-surface receptor.
33. The composition according to any one of embodiments 1 to 32, wherein the cell surface target is an internalizing cell-surface receptor that is selected from the group consisting of cell type specific carbohydrates, receptor tyrosine kinases such as HER1, HER2, HER3, IGF1R, cell type specific antigens, such as Mesothelin, PSMA, CD19, CD20, CD44, TfR, LRPs, IL-receptors.
34. The composition according to any one of embodiments 1 to 33, wherein the composition comprises one or more molecules of the bispecific binder.
35. The composition according to any one of embodiments 1 to 34, wherein the hapten is biotin, the bispecific binder is a bispecific antibody and the first binding specificity is a pair of an antibody light chain variable domain and an antibody heavy chain variable domain comprising (a) a HVR-H1 comprising the amino acid sequence of SEQ ID NO: 23, (b) a HVR-H2 comprising the amino acid sequence of SEQ ID NO: 24, (c) a HVR-H3 comprising the amino acid sequence of SEQ ID NO: 25, (d) a HVR-L1 comprising the amino acid sequence of SEQ ID NO: 27, (e) a HVR-L2 comprising the amino acid sequence of SEQ ID NO: 28, and (f) a HVR-L3 comprising the amino acid sequence of SEQ ID NO: 29.
36. The composition according to any one of embodiments 1 to 34, wherein the hapten is digoxygenin, the bispecific binder is a bispecific antibody and the first binding specificity is a pair of an antibody light chain variable domain and an antibody heavy chain variable domain comprising (a) a HVR-H1 comprising the amino acid sequence of SEQ ID NO: 15, (b) a HVR-H2 comprising the amino acid sequence of SEQ ID NO: 16, (c) a HVR-H3 comprising the amino acid sequence of SEQ ID NO: 17, (d) a HVR-L1 comprising the amino acid sequence of SEQ ID NO: 19, (e) a HVR-L2 comprising the amino acid sequence of SEQ ID NO: 20, and (f) a HVR-L3 comprising the amino acid sequence of SEQ ID NO: 21.
37. The composition according to any one of embodiments 1 to 34, wherein the hapten is theophylline, the bispecific binder is a bispecific antibody and the first binding specificity is a pair of an antibody light chain variable domain and an antibody heavy chain variable domain comprising (a) a HVR-H1 comprising the amino acid sequence of SEQ ID NO: 31, (b) a HVR-H2 comprising the amino acid sequence of SEQ ID NO: 32, (c) a HVR-H3 comprising the amino acid sequence of SEQ ID NO: 33, (d) a HVR-L1 comprising the amino acid sequence of SEQ ID NO: 35, (e) a HVR-L2 comprising the amino acid sequence of SEQ ID NO: 36, and (f) a HVR-L3 comprising the amino acid sequence of SEQ ID NO: 37.
38. The composition according to any one of embodiments 1 to 34, wherein the hapten is fluorescein, the bispecific binder is a bispecific antibody and the first binding specificity is a pair of an antibody light chain variable domain and an antibody heavy chain variable domain comprising (a) a HVR-H1 comprising the amino acid sequence of SEQ ID NO: 39, (b) a HVR-H2 comprising the amino acid sequence of SEQ ID NO: 40, (c) a HVR-H3 comprising the amino acid sequence of SEQ ID NO: 41, (d) a HVR-L1 comprising the amino acid sequence of SEQ ID NO: 43, (e) a HVR-L2 comprising the amino acid sequence of SEQ ID NO: 44 and (f) a HVR-L3 comprising the amino acid sequence of SEQ ID NO: 45.
39. The composition according to any one of embodiments 1 to 34, wherein the hapten is bromodeoxyuridine, the bispecific binder is a bispecific antibody and the first binding specificity is a pair of an antibody light chain variable domain and an antibody heavy chain variable domain comprising (a) a HVR-H1 comprising the amino acid sequence of SEQ ID NO: 47, (b) a HVR-H2 comprising the amino acid sequence of SEQ ID NO: 48, (c) a HVR-H3 comprising the amino acid sequence of SEQ ID NO: 49, (d) a HVR-L1 comprising the amino acid sequence of SEQ ID NO: 51, (e) a HVR-L2 comprising the amino acid sequence of SEQ ID NO: 52, and (f) a HVR-L3 comprising the amino acid sequence of SEQ ID NO: 53.
40. The composition according to any one of embodiments 1 to 34, wherein the hapten is a helicar motif polypeptide of SEQ ID NO: 57, the bispecific binder is a bispecific antibody and the first binding specificity is a pair of an antibody light chain variable domain and an antibody heavy chain variable domain comprising a HVR-H1, a HVR-H2 and a HVR-H3 of SEQ ID NO: 55, and a HVR-L1, a HVR-L2 and a HVR-L3 of SEQ ID NO: 56.
41. The composition according to any one of embodiments 1 to 40, wherein each hapten is specifically bound by one/a single bispecific binder.
42. The composition according to any one of embodiments 1 to 41, wherein the large nucleic acid encodes CRISPR/Cas9.
43. The composition according to any one of embodiments 1 to 41, wherein the large nucleic acid comprises:
CRISPR/Cas-system nucleic acids, and/or
an expression cassette for a polypeptide endogenous to the mammalian cell, and/or
an expression cassette for polypeptides that encodes enzymes or other proteins/peptides with therapeutic function, and/or
a transcription system for non-coding RNA with therapeutic function like micro RNA, short interfering RNA, long non-coding RNA, RNA decoys, RNA aptamers and ribozymes.
44. A pharmaceutical formulation comprising the composition according to any one of embodiments 1 to 43 and a pharmaceutically acceptable carrier.
45. The composition according to any one of embodiments 1 to 43 for use as a medicament.
46. The composition according to any one of embodiments 1 to 43 for use in gene therapy.
47. Use of the composition according to any one of embodiments 1 to 43 in the manufacture of a medicament.
48. A method of treating an individual having a genetic disease comprising administering to the individual an effective amount of the composition according to any one of embodiments 1 to 43.
49. A method of modifying gene expression in the cells of an individual comprising administering to the individual an effective amount of the composition according to anyone one of embodiments 1 to 43 to modify gene expression.
50. A method for preparing a composition according to any one of embodiments 1 to 43 comprising the following steps:
a) incubating the large nucleic acid and the histone to form a large-nucleic-acid-histone-complex, wherein either the large nucleic acid or the histone or both are conjugated to at least one hapten molecule,
b) incubating the large-nucleic-acid-histone-complex formed in a) with a bispecific binder to generate a bispecific-binder-large-nucleic-acid-histone-complex,
c) isolating and/or purifying the bispecific-binder-large-nucleic-acid-histone-complex complex formed in step b) and thereby producing the composition according to any one of embodiments 1 to 43.
51. A method for introducing a large nucleic acid into a eukaryotic cell comprising the following step(s):
a) incubating the eukaryotic cell with a composition according to any one of embodiments 1 to 43 under conditions suitable for the binding of the bispecific binder to the cell-surface target,
b) isolating a cell comprising the large nucleic acid or a functional fragment thereof, and thereby introducing a large nucleic acid into a eukaryotic cell.
52. A method for transfecting a eukaryotic cell comprising the following step(s):
a) incubating the eukaryotic cell with a composition according to any one of embodiments 1 to 43 under conditions suitable for the binding of the bispecific binder to the cell-surface target,
b) isolating a cell comprising the large nucleic acid or a functional fragment thereof, and thereby transfecting a eukaryotic cell.
53. A method for transporting a nucleic acid into a eukaryotic cell comprising the following step(s):
a) incubating the eukaryotic cell with a composition according to any one of embodiments 1 to 43 under conditions suitable for the binding of the bispecific binder to the cell-surface target,
b) isolating a cell comprising the large nucleic acid or a functional fragment thereof, and thereby transporting a large nucleic acid into a eukaryotic cell.
54. A method for transporting a nucleic acid into the nucleus of a eukaryotic cell comprising the following step(s):
a) incubating the eukaryotic cell with a composition according to any one of embodiments 1 to 43 under conditions suitable for the binding of the bispecific binder to the cell-surface target,
b) isolating a cell comprising the large nucleic acid or a functional fragment thereof, and thereby transporting a large nucleic acid into the nucleus of a eukaryotic cell.
55. Use of a composition according to any one of embodiments 1 to 43 for the targeted delivery of a large nucleic acid into a eukaryotic cell.
56. Use of a composition according to any one of embodiments 1 to 43 for the introduction of a large nucleic acid or a functional fragment thereof into the nucleus of a eukaryotic cell.
57. The composition according to any one of embodiments 1 to 43, wherein the composition is for the introduction of a large nucleic acid or functional fragment thereof in a eukaryotic cell.
58. The composition according to any one of embodiments 1 to 43, wherein the composition is for the transfection of a eukaryotic cell with a large nucleic acid or functional fragment thereof
59. A cell obtained with a method according to any one of embodiments 51 to 54 and the progeny thereof
60. A method for transfecting a defined subpopulation of a population of eukaryotic cells with a large nucleic acid comprising the following step:
incubating a population of eukaryotic cells comprising at least two sub-populations differing in at least one cell-surface antigen with a composition according to any one of claims 1 to 43, wherein the second binding specificity of the bispecific binder specifically binds to a cell-surface antigen that is only present on a sub-population of the population of eukaryotic cells, and thereby transfecting a defined sub-population of a population of eukaryotic cells with a large nucleic acid.

The following examples, sequences and figures are provided to aid the understanding of the present invention, the true scope of which is set forth in the appended claims. It is understood that modifications can be made in the procedures set forth without departing from the spirit of the invention.

A: haptens are chemically conjugated to plasmid-chromatin;

B: haptens are attached via DNA-binding peptides.

Figure 1:
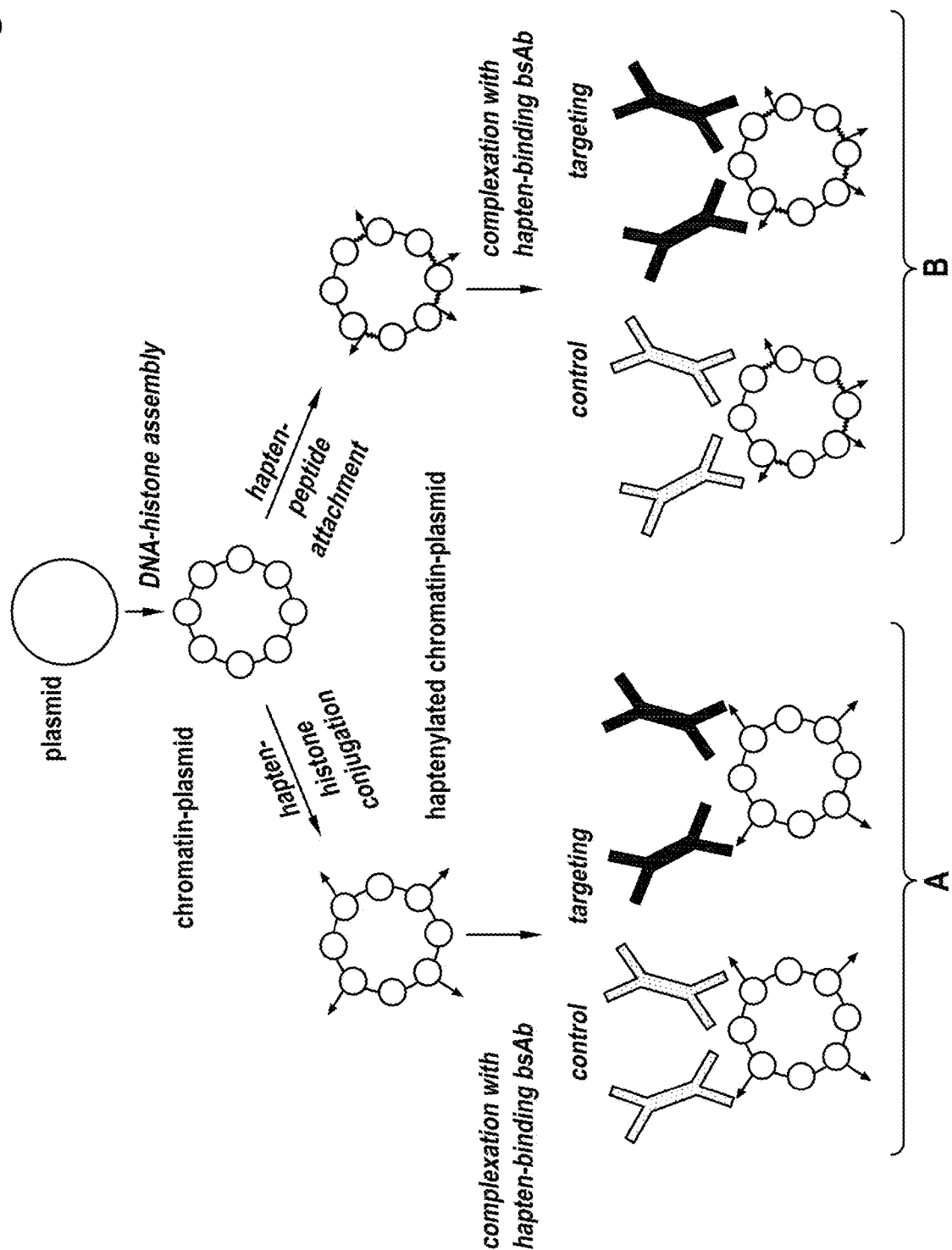
FIG. 1 Schematic overview of the modules applied and process steps for generating entities that enable specifically targeted and efficient intracellular delivery of plasmids.
Figure 2:
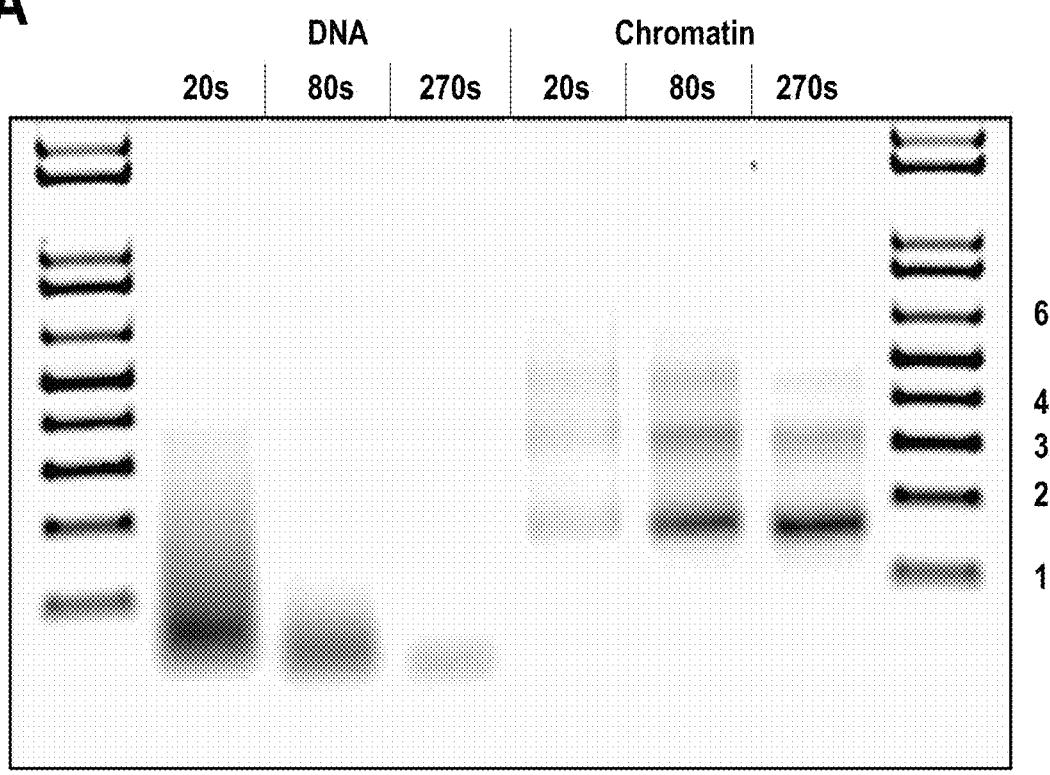
Figure 2:
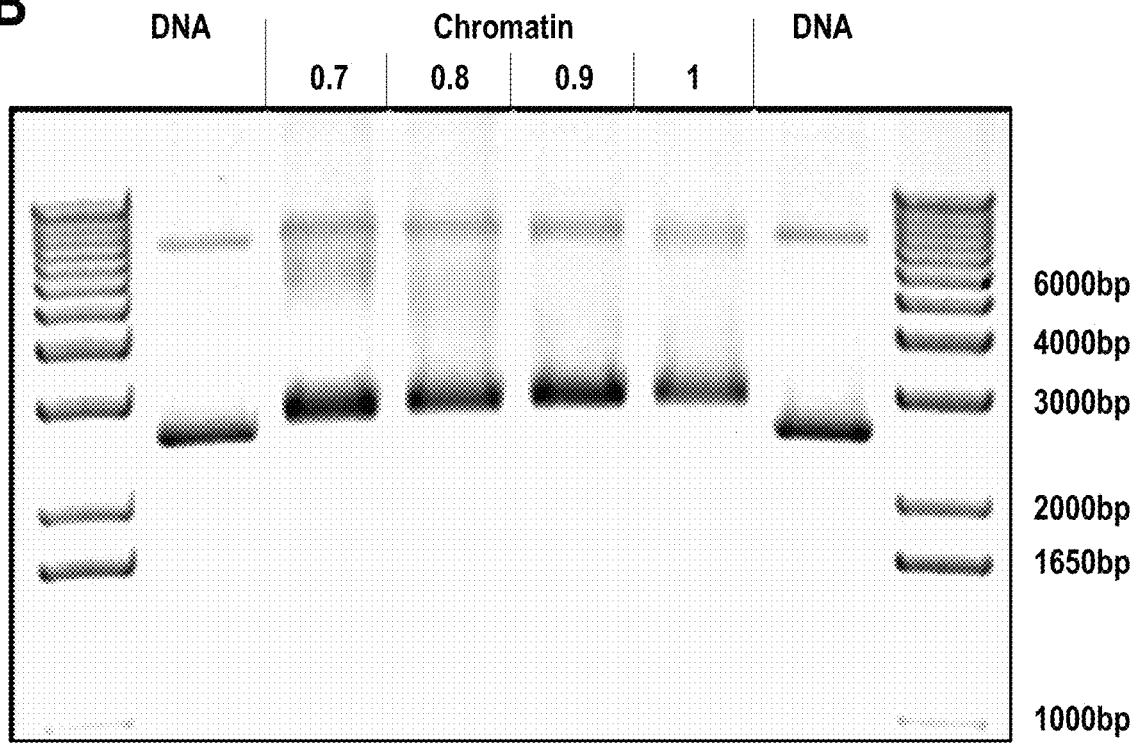

FIG. 2 Analysis of assembled Chromatin by agarose gel electrophoresis; Chromatin was assembled with calf thymus Histone octamers and an eGFP expression plasmid.

A: Analysis of Chromatin quality by micrococcal nuclease digestion; peGFP was treated with MNase for the indicated time points (20, 80 and 270 seconds) before (DNA) and after (chromatin) histone assembly.

B: EMSA shift assay with plasmid DNA alone and Chromatin assembled with indicated ratios of ng (histone): ng (DNA).

Figure 3:
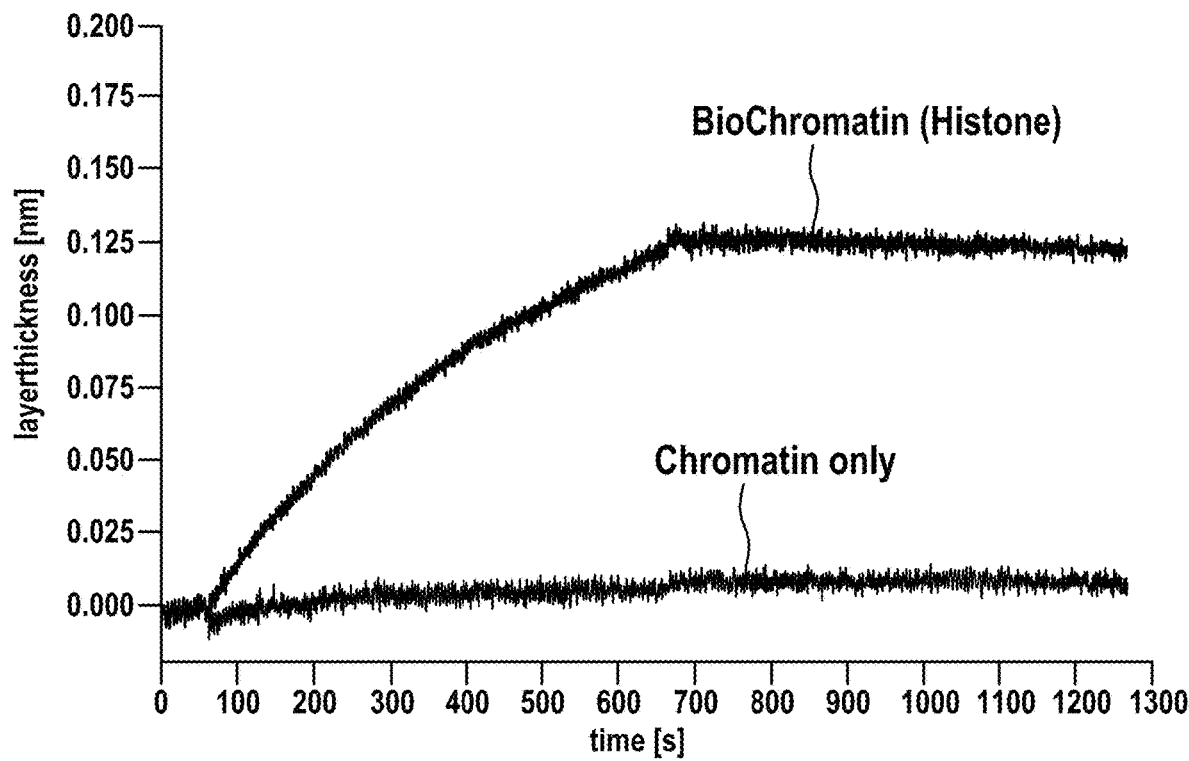
Figure 3:
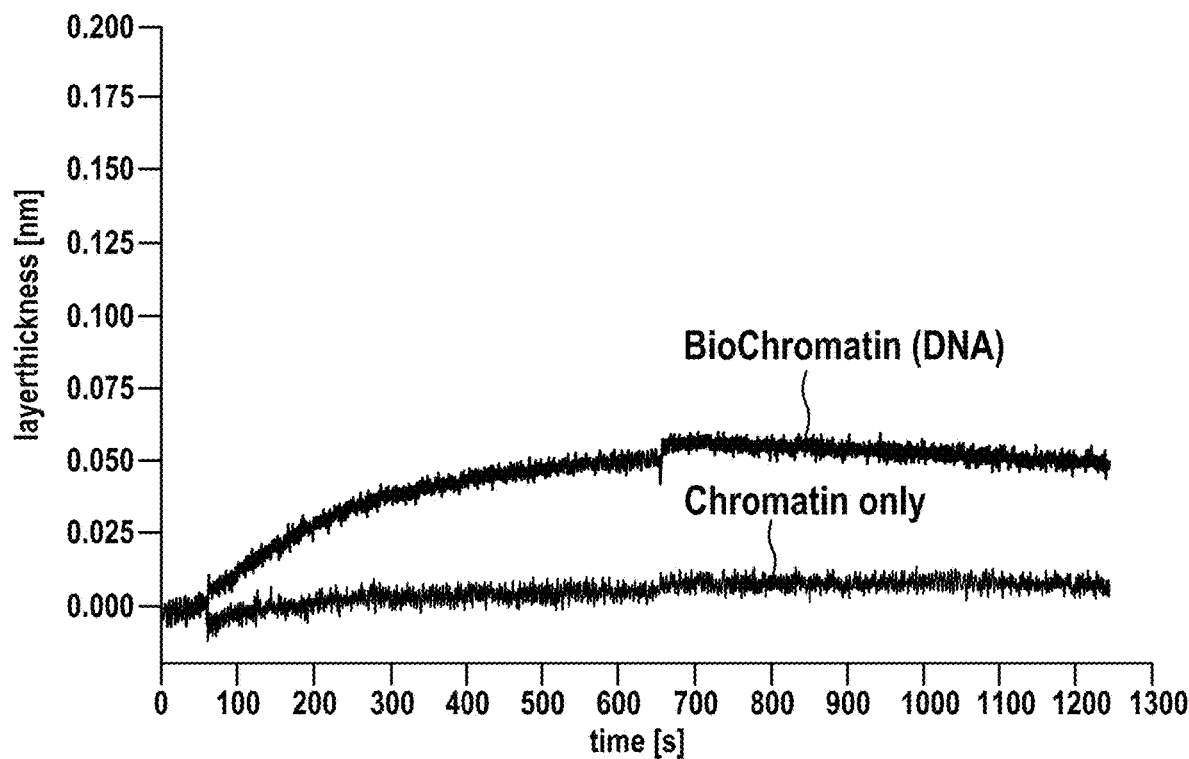
Figure 3:
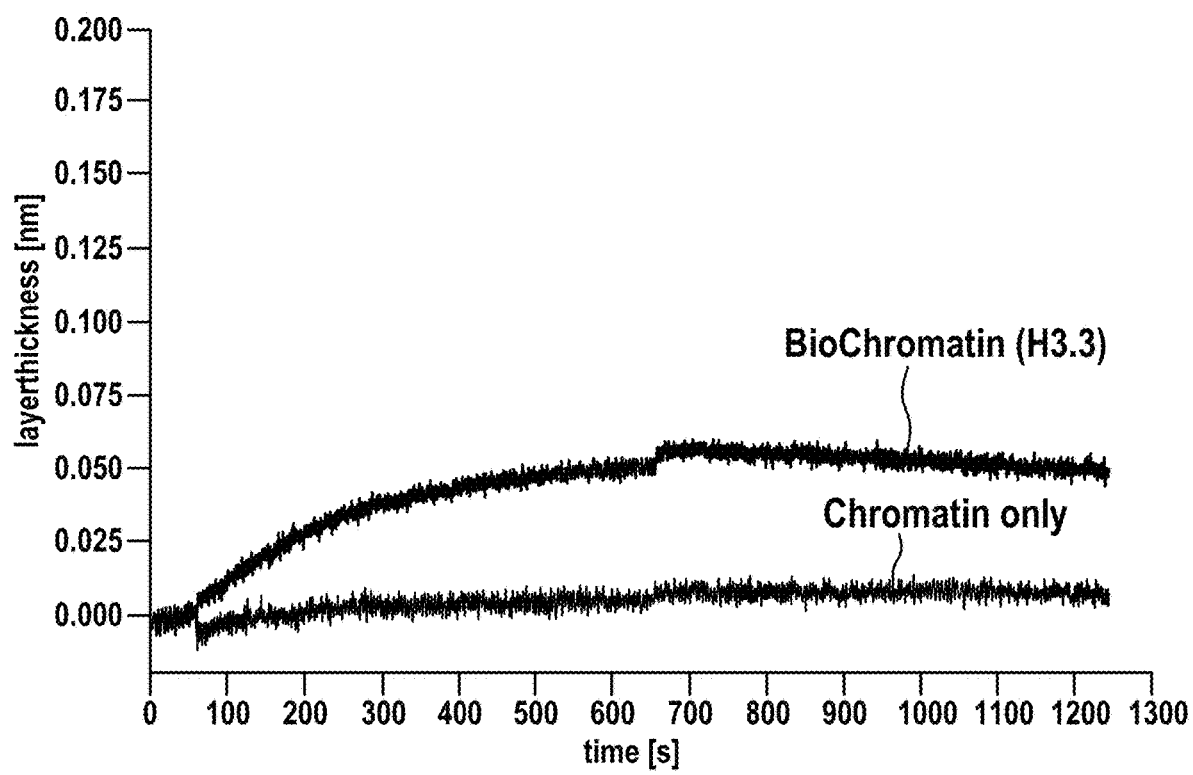

FIG. 3 Generation of haptenylated plasmid-chromatin by chemical conjugation and analysis via interaction with Streptavidin. 8 µg/mL Chromatin was incubated with Streptavidin dips for 10 min. (displayed in time frame 60 s-660 s). Gain of layer thickness indicates binding Chromatin to the dips of the Octet system measured by increase of absorbance:

A: Streptavidin binding of biotinylated chromatin generated by lysine side conjugation;

B: Streptavidin binding of biotinylated chromatin generated by biotinylation of plasmid DNA prior to nucleosome assembly;

C: Streptavidin binding of biotinylated chromatin generated by applying biotinylated histones for chromatin assembly.

Figure 4:
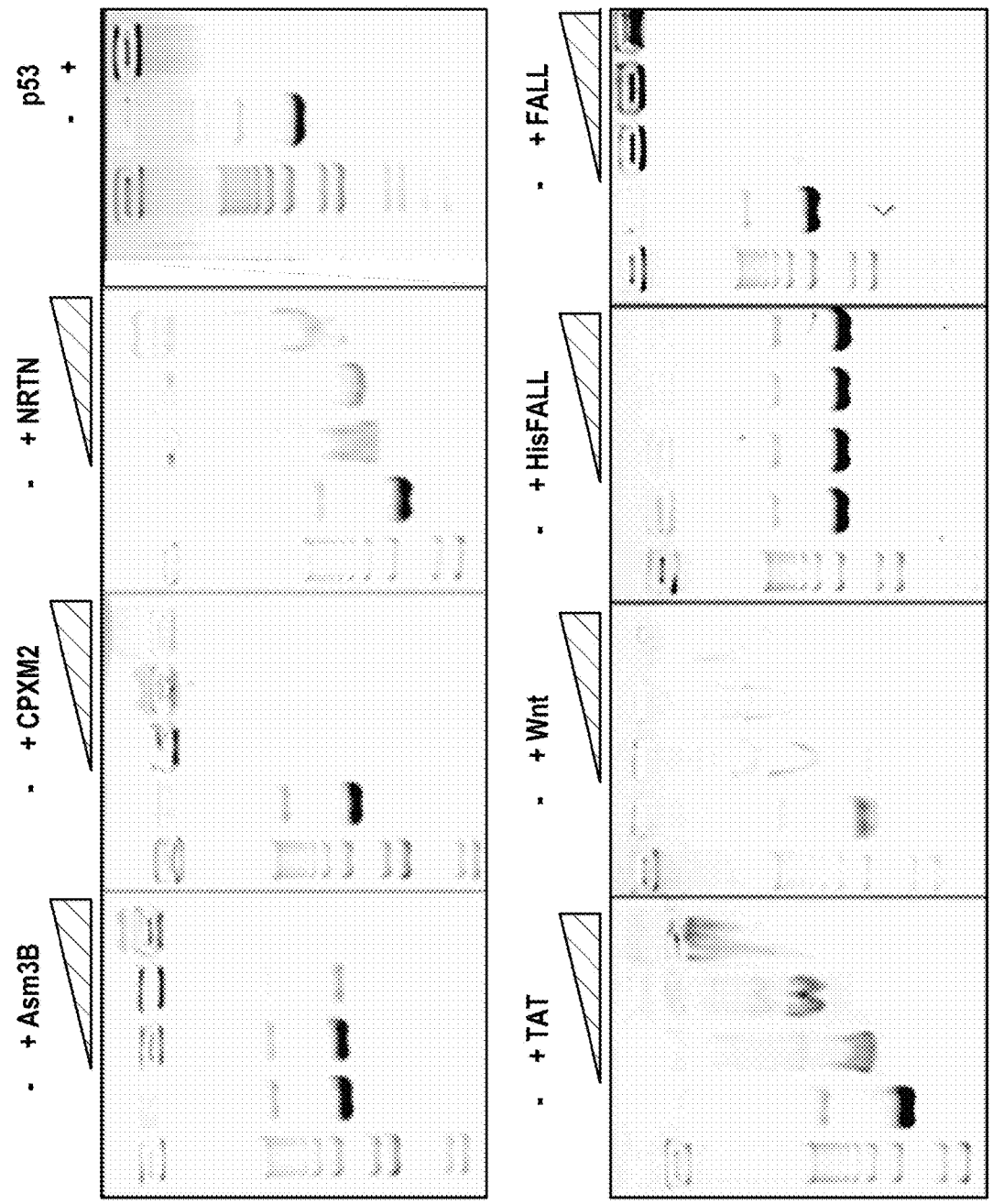
Figure 4:
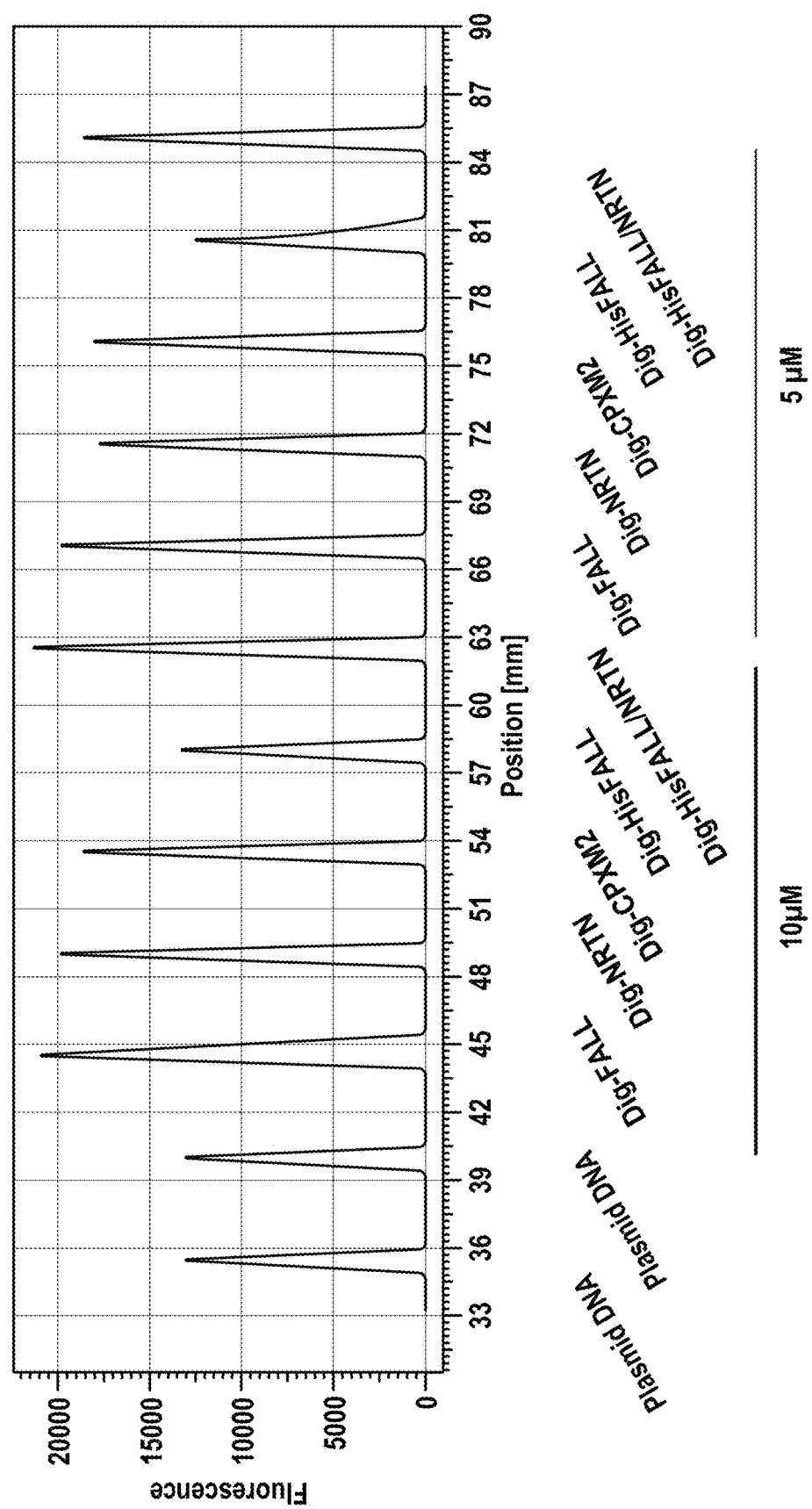

FIG. 4 Assembly of plasmid DNA with peptides:

A: EMSA shift to determine DNA binding properties of cell-penetrating peptides: gel shift was performed after incubation of DNA with constant amount (0.5 µg) with various peptides at increasing amounts (1 µg, 2 µg, 4 µg) indicated by triangle.

B: Microscale thermophoresis analysis (MST): MST was performed for indicated peptides at 5 µM and 10 µM peptide concentration. Incubation of DNA with the peptides FALL NRTN and CPXM2 resulted in an increase of fluorescence. Incubation of DNA with the uncharged HisFALL peptide did not result in an increase of fluorescence signal.

Figure 5:
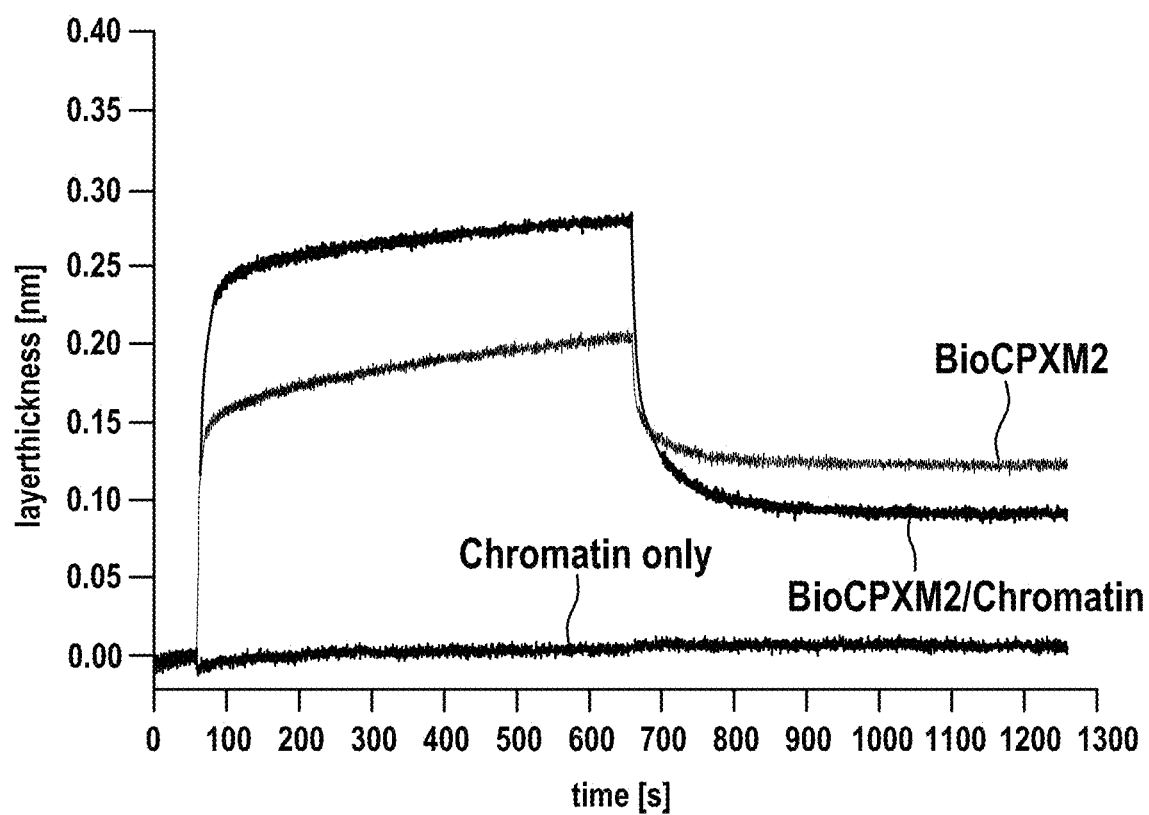

FIG. 5 Generation of haptenylated plasmid-nucleosomes by attachment of haptenylated DNA-binding peptides:

10 µg/mL chromatin was incubated with Streptavidin dips for 15 min. Gain of layer thickness indicates binding Chromatin to the dips of the Octet system measured by increase of absorbance. The figure shows biotinylated plasmid-chromatin generated by attachment of the bio-CPXM2 peptide.

Figure 6:
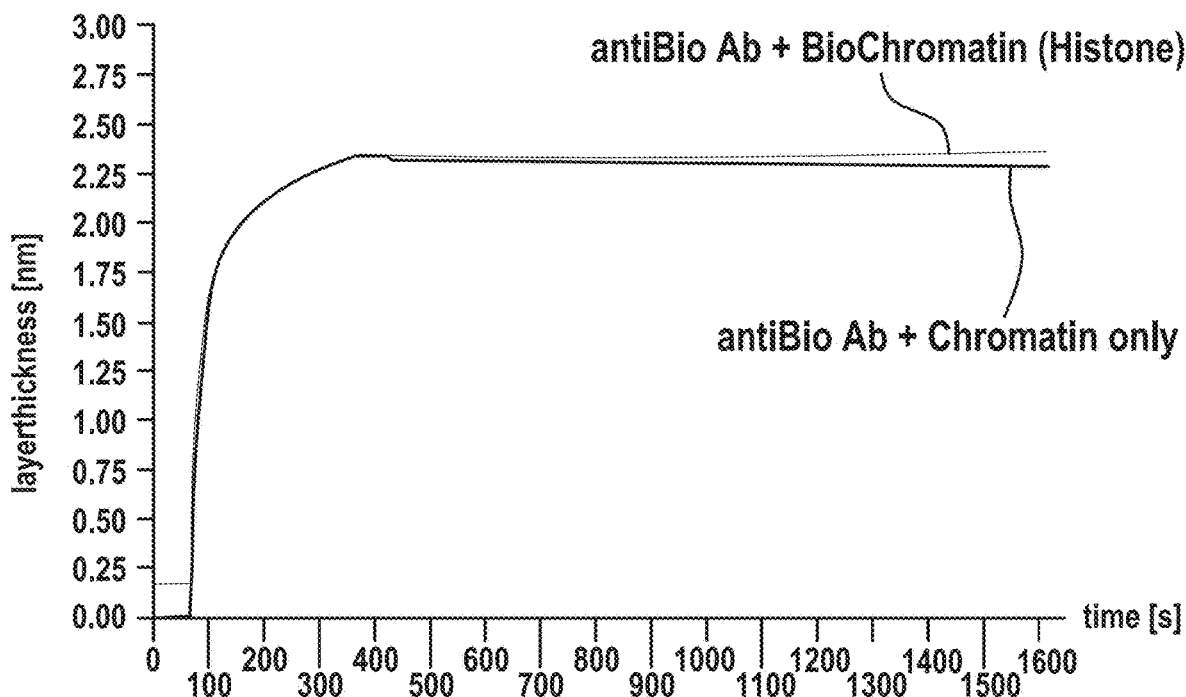
Figure 6:
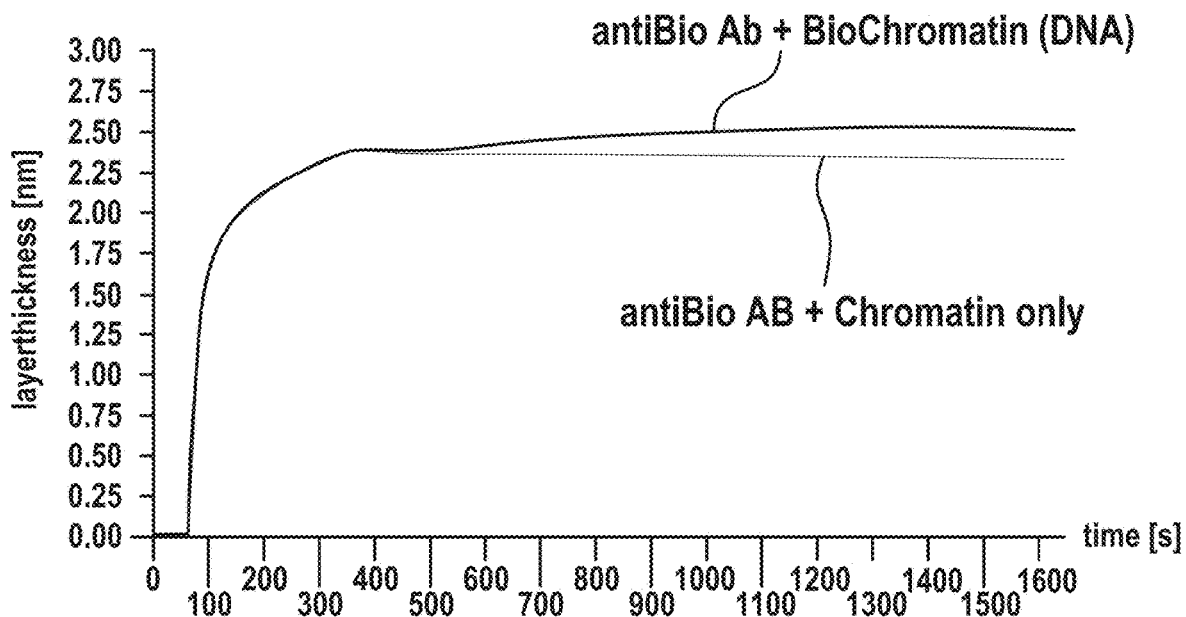
Figure 6:
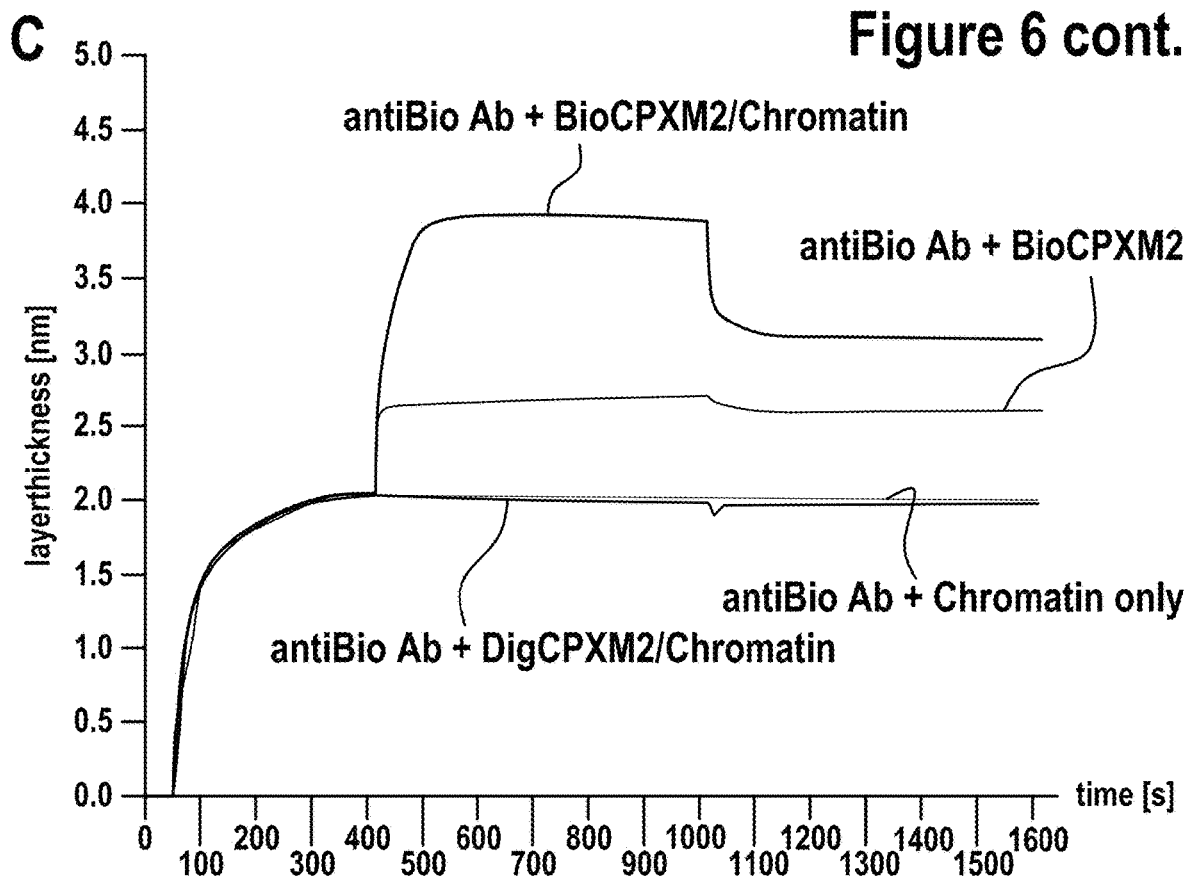
Figure 6:
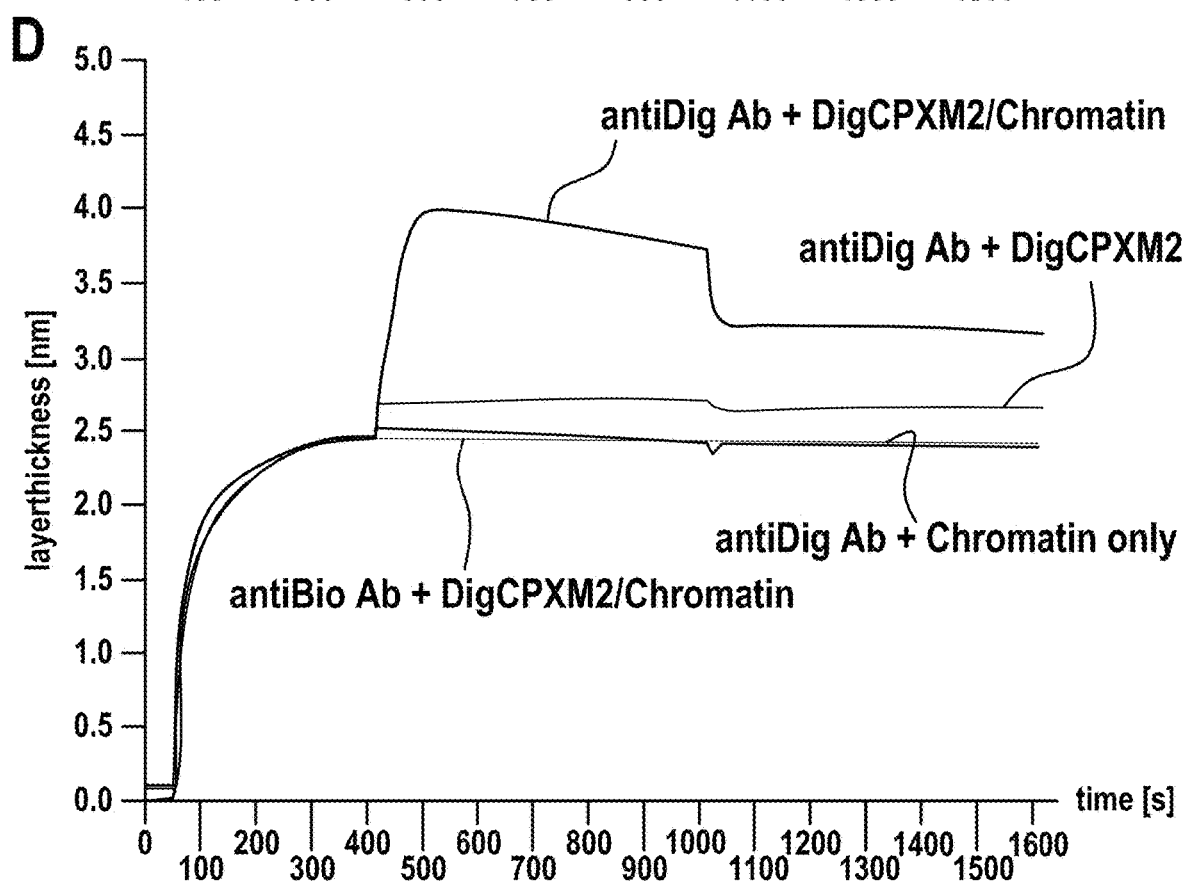

FIG. 6 Complexation of biotinylated plasmid-chromatin with hapten-binding bsAbs. Protein A dips were exposed to and bind biotin- or digoxigenin-binding bsAbs (1st binding curve). Subsequent exposure to and binding of biotinylated or digoxigenylated plasmid-chromatin is represented by the 2nd binding curve:

A: Complex formation of bsAbs to plasmid-chromatin that was biotinylated by chemical conjugation of chromatin;

B: Complex formation of bsAbs to plasmid-chromatin that was biotinylated by chemical conjugation of plasmid DNA prior to chromatin assembly;

C: Complex formation of the binding of bsAbs to biotinylated plasmid-chromatin that was obtained by adding biotinylated DNA-binding peptides to plasmid-chromatin;

D: Complex formation of the binding of bsAbs to digoxigenylated plasmid-chromatin that was obtained by adding digoxigenylated DNA-binding peptides to plasmid-chromatin.

Figure 7:
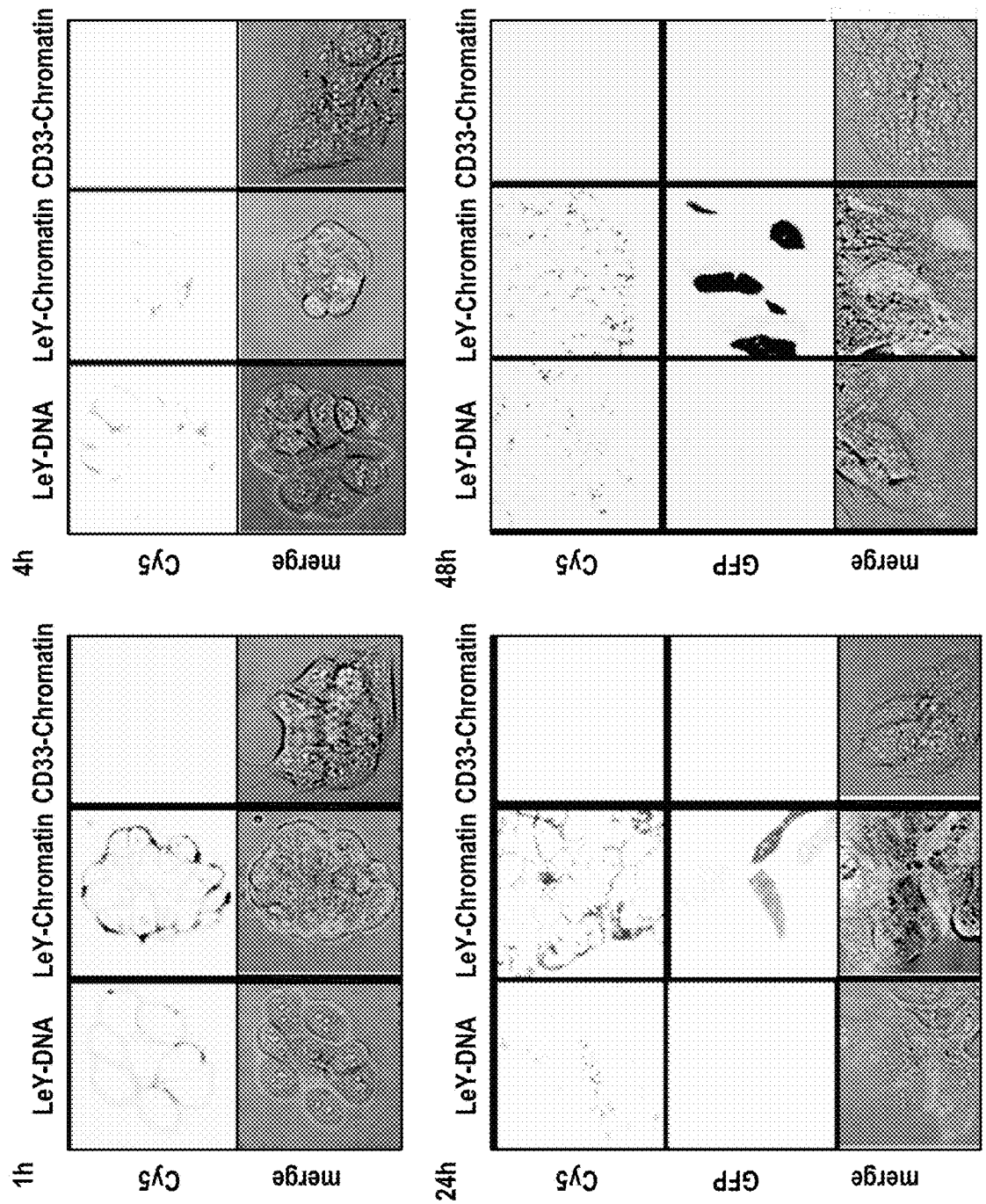

FIG. 7 Delivery of bsAb-targeted plasmids and plasmid-chromatin to target cells: BsAb—targeted delivery and internalization of haptenylated plasmid DNA (LeY-DNA); bsAb—targeted delivery and internalization of plasmid-chromatin haptenylated via peptide attachment (LeY-Chromatin); treatment with control bsAb and plasmid chromatin haptenylated via peptide attachment (CD33-Chromatin).

Figure 8:
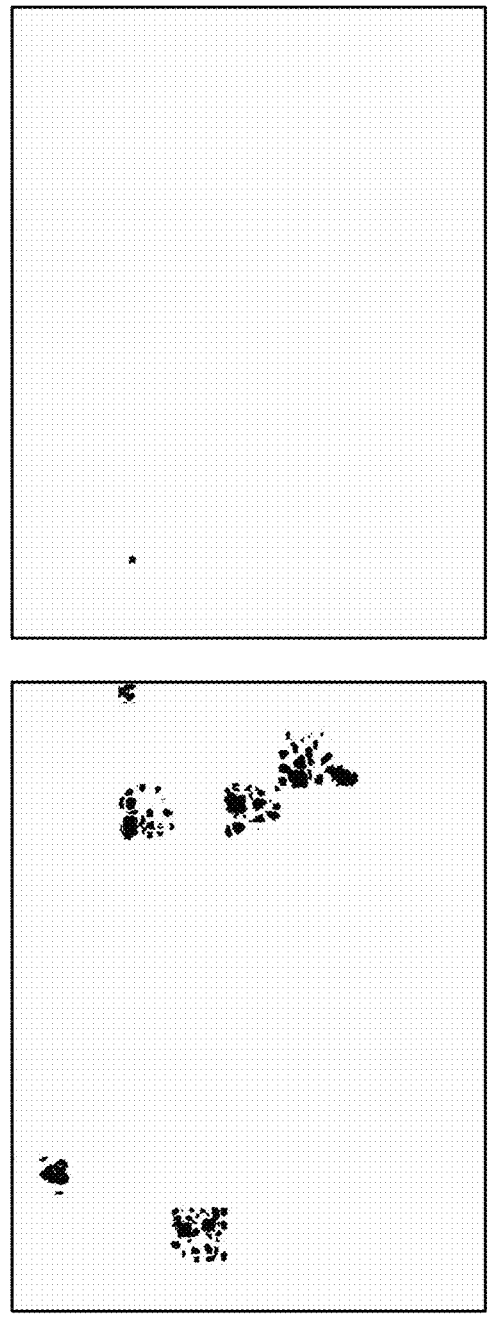

FIG. 8 Intracellular delivery & intracellular functionality of bsAb-targeted peptide-plasmid assemblies.

bsAb-targeted intracellular plasmid delivery enables GFP expression in target cells (left panel) but not in non-target cells (right panel).

Figure 9:
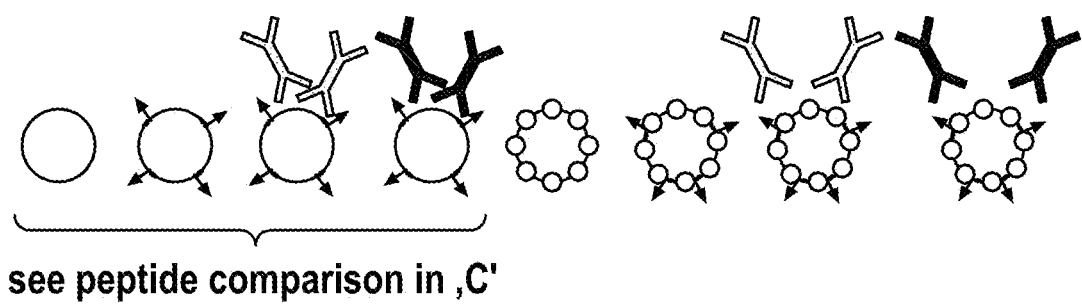
Figure 9:
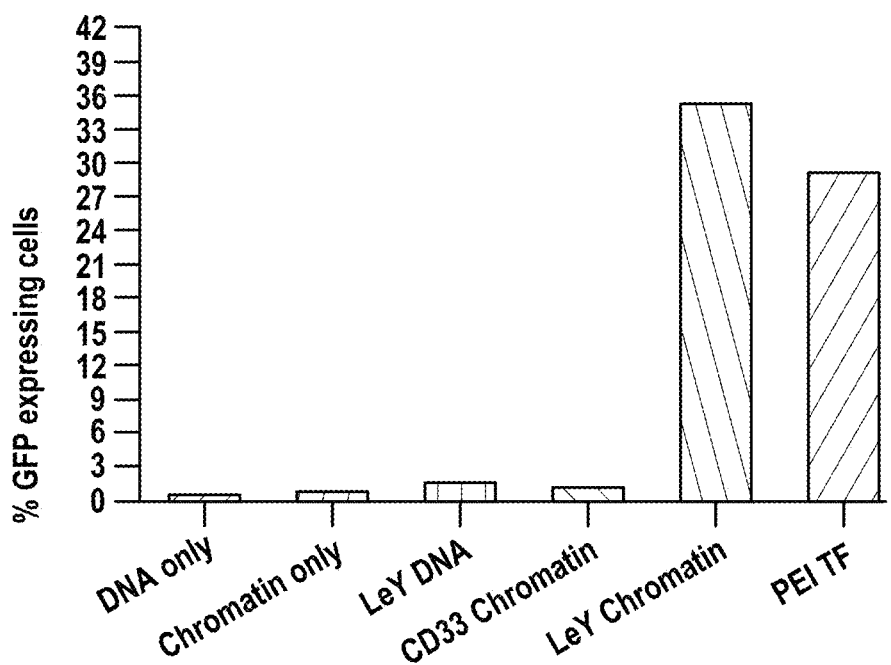
Figure 9:
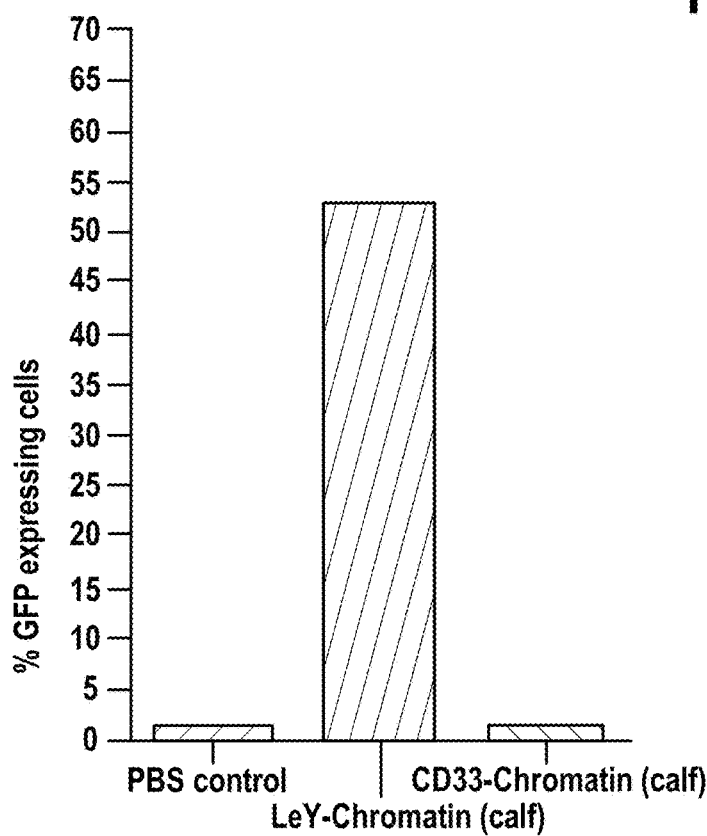
Figure 9:
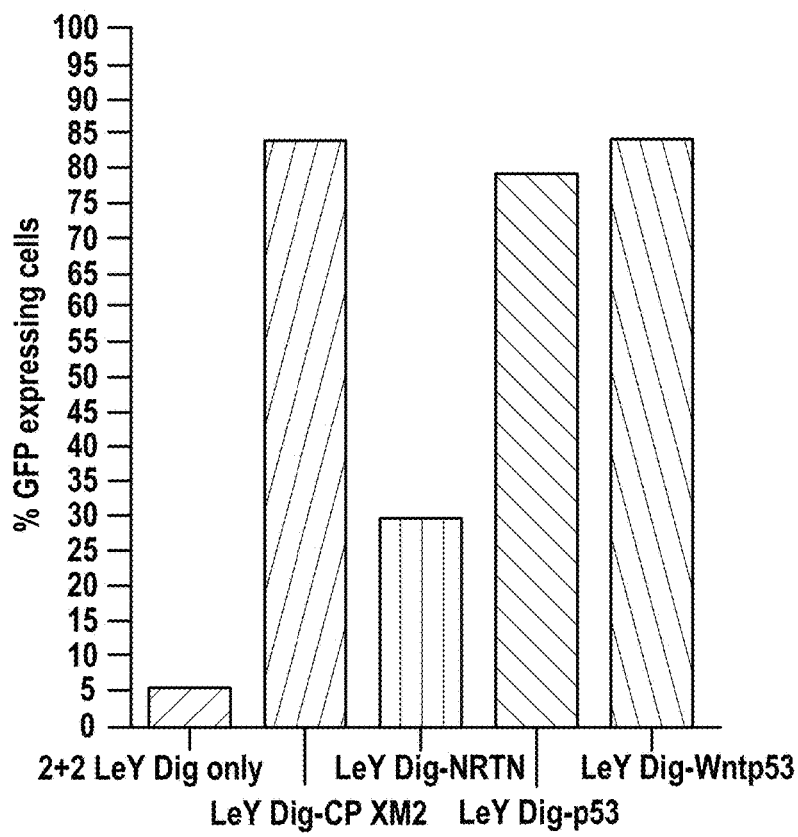
Figure 9:
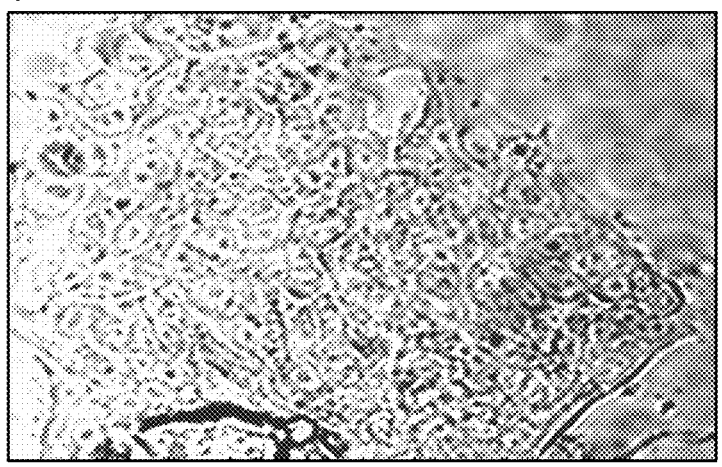
Figure 9:
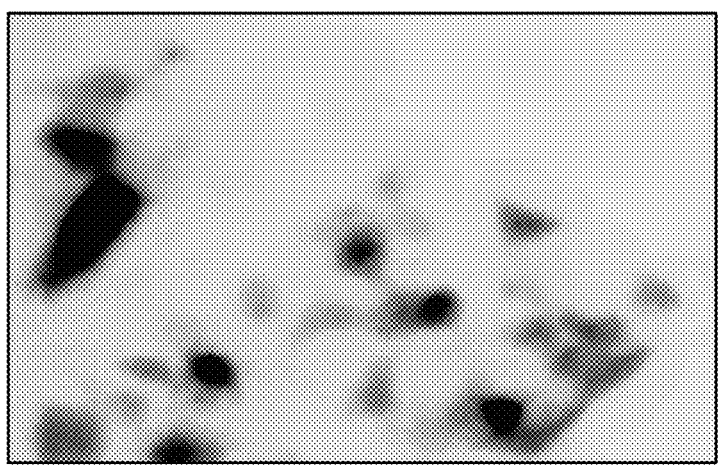
Figure 9:
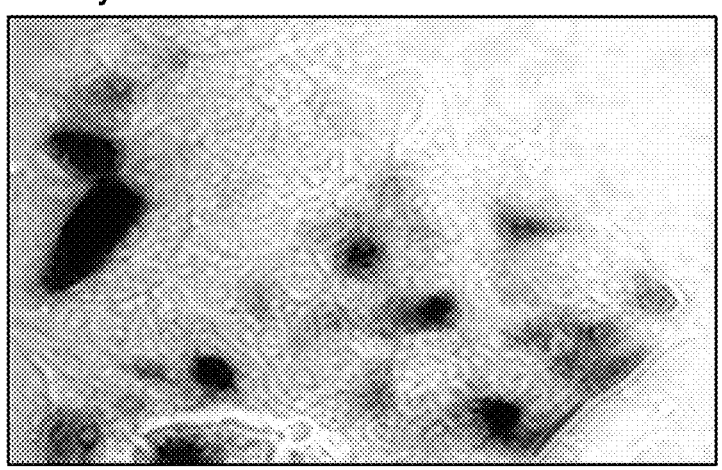
Figure 9:
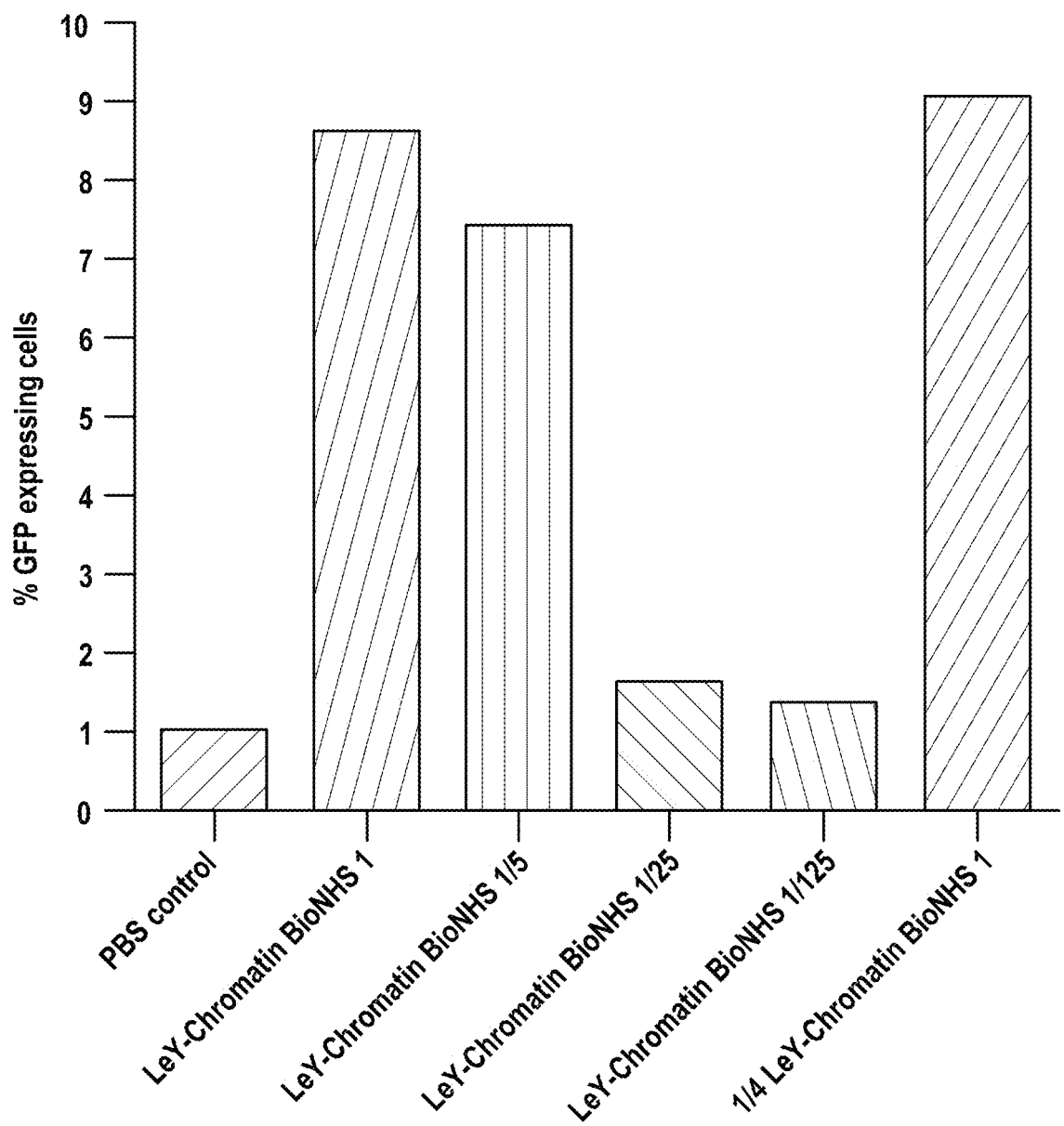

FIG. 9 Intracellular delivery & functionality of bsAb-targeted plasmid-chromatin complexes:

A: Generation of bsAb-targeted peptide-plasmid-chromatin delivery components;

B: 2+1 TriFab format; comparison of chromatin (digoxigenylated by peptide addition) delivery by bispecific tripleFabs with PEI transfection;

C: 2+2 bsAb format; targeting of chromatin (digoxigenylated by peptide addition) by bivalent bispecific antibodies;

D: Comparison of delivery efficacy of complexed chromatin with different dig-peptides;

E: Fluorescence microscopic image of targeted Chromatin by bispecific antibody and CPXM2 peptide;

F: TriFab-mediated targeting of Chromatin that was biotinylated by chemical conjugation: Chromatin labelled with indicated amounts of NHS-Biotin was incubated with anti LeY anti Biotin TriFab. MCF7 cells were treated with the pre-incubated TriFab-Chromatin at a final concentration of 8 µg Chromatin/mL and 120 nM TriFab or one fourth of both concentrations.

Figure 10:
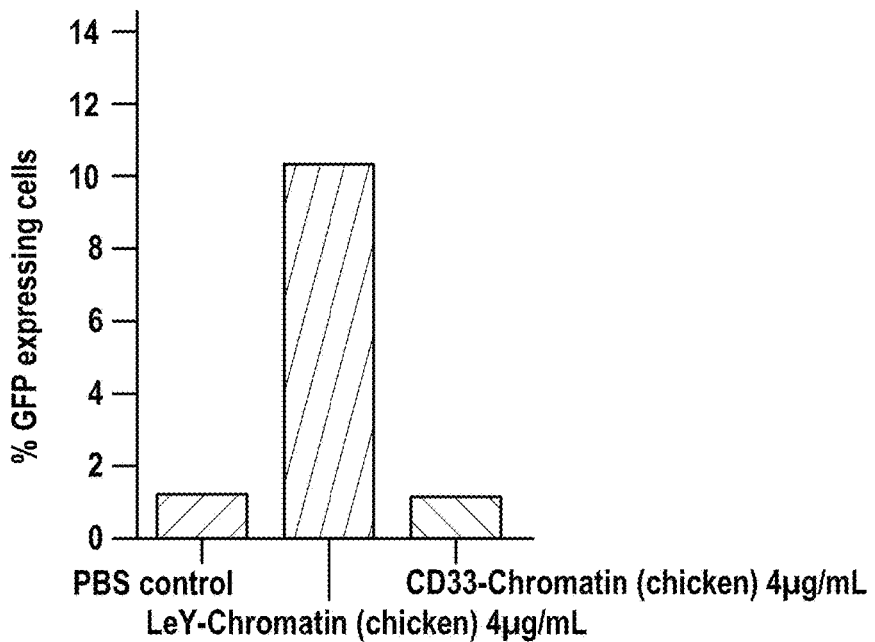
Figure 10:
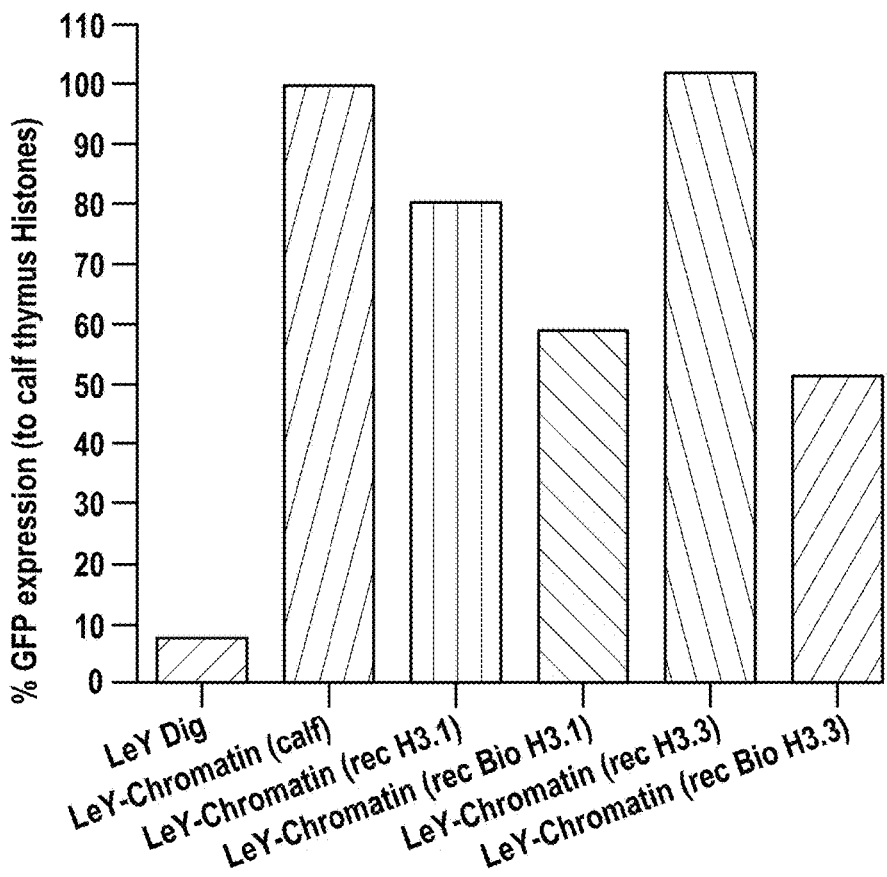
Figure 10:
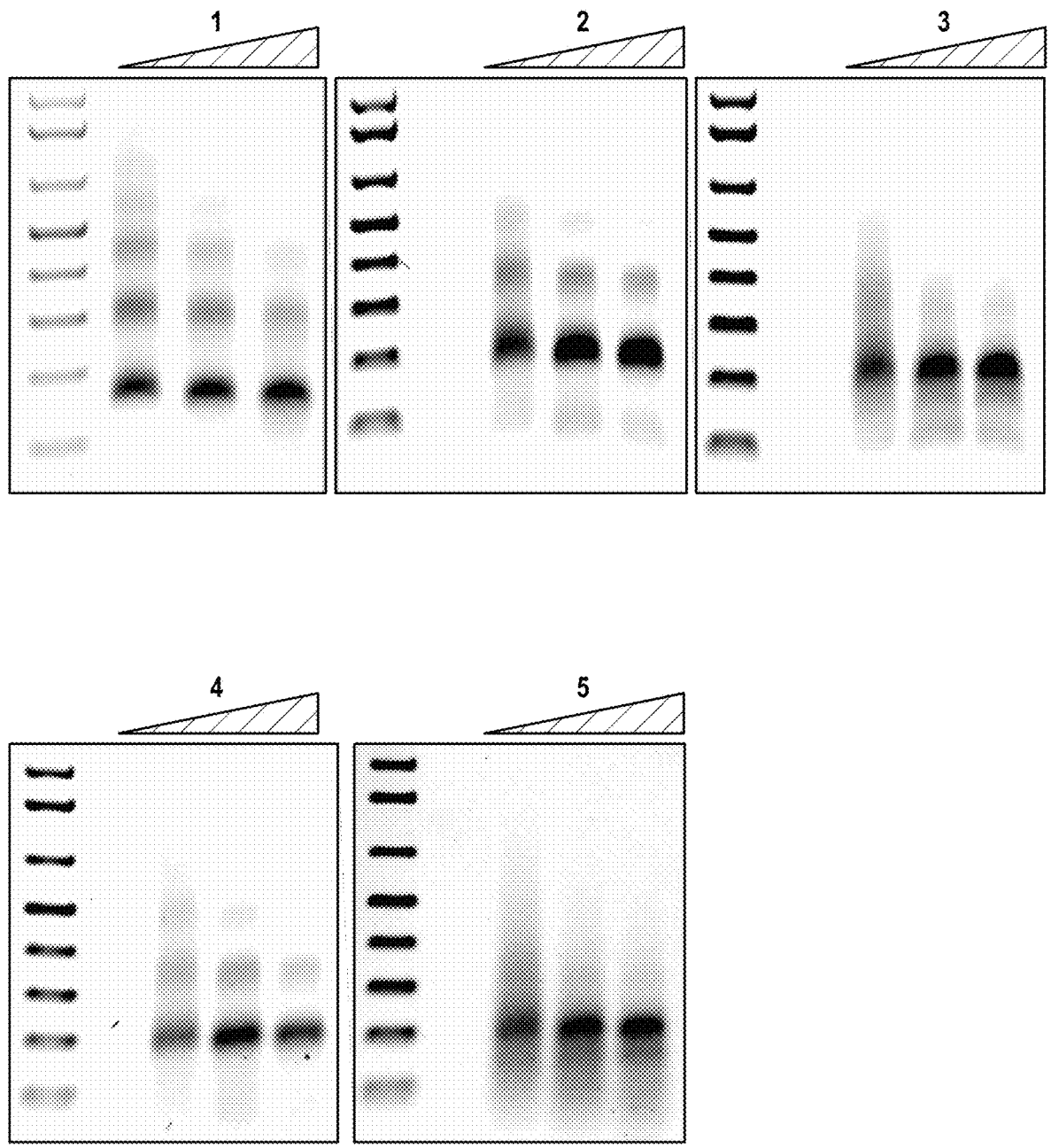

FIG. 10 Targeted delivery of plasmid-chromatin harboring chicken histones or recombinant human histone:

A: treatment with Chromatin targeting system comprising bispecific antibody, peptide and Chromatin assembled with chicken erythrocyte histones. 48 h after treatment with cell surface targeting construct (LeY-Chromatin) results in 10% fluorescent cell in contrast to the non-targeting construct (CD33-Chromatin) with a fluorescence signal at background level;

B: Various recombinant histone octamers were compared to calf thymus histones. The targeting system comprising a recombinant histone Octamer with an unmodified histone 3.3 subunit shows delivery efficacy comparable to calf thymus histones whereas chromatin comprising subunit 3.1 shows a slightly reduced delivery efficacy. Specific biotinylation of subunit H3 reduces delivery efficacy in comparison to the respective unmodified versions;

C: Quality of chromatin assembled with histones tested in B above. High quality chromatin was obtained with calf thymus histones (1), recombinant histone octamers with human H3.1 (2) and human H3.3 (4) because of distinct band pattern and only slight sub-nucleosomal DNA. Chromatin assembly with biotinylated versions of recombinant histone octamers with human H3.1 (3) and human H3.3 (5) results in low quality chromatin as only one band is predominant with a broad sub-nucleosomal smear.

Figure 11:
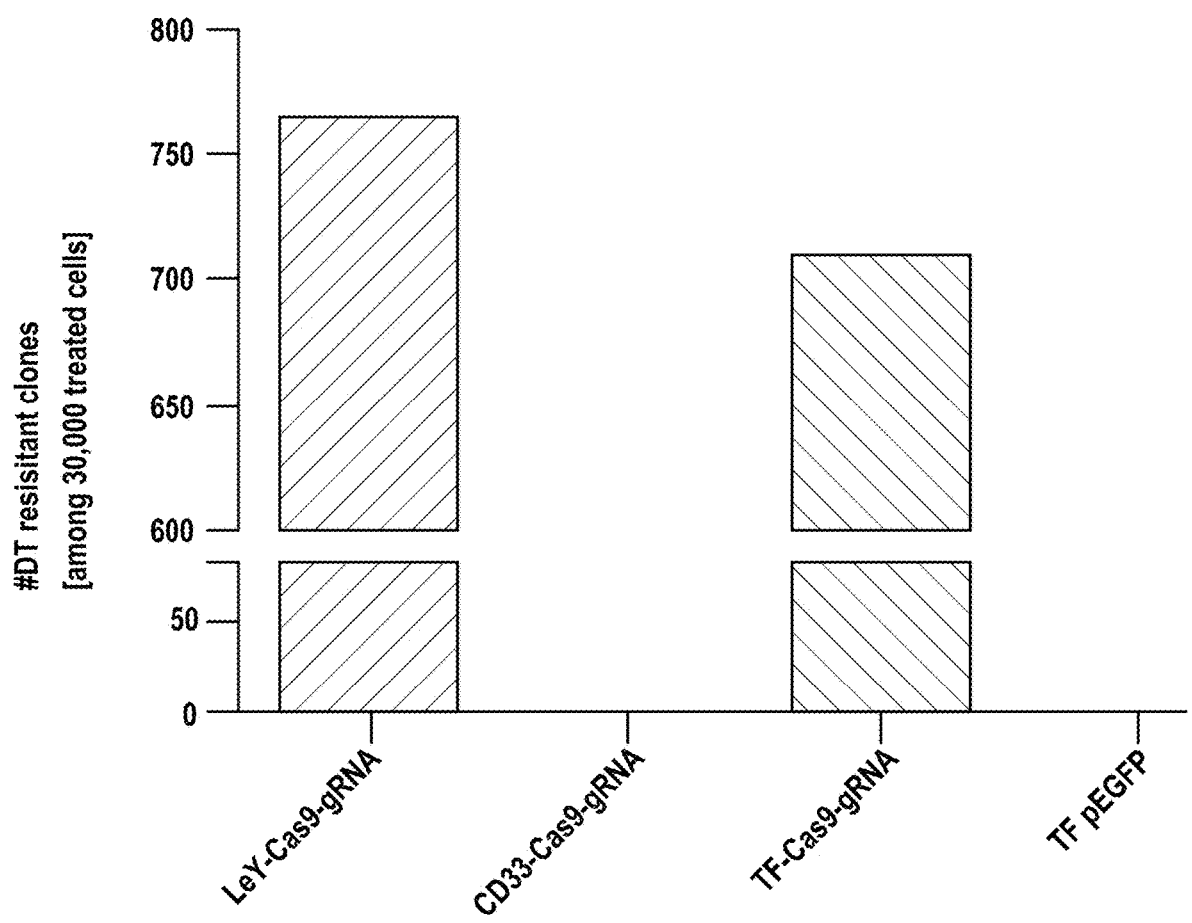

FIG. 11 Intracellular delivery and activity of CRISPR/Cas9 encoding plasmids that are delivered in form of antibody-targeted plasmid-chromatin. MCF7 cells (LeY+++, CD33-) exposed to LeY-targeted plasmid-chromatin become DT resistant as consequence of DPH1 gene inactivation via targeted plasmid delivery. DT/resistance indicative for DPH1 gene inactivation is not observed in cell populations that received plasmid-chromatin that was not targeted to cells by antibodies.

Figure 12:
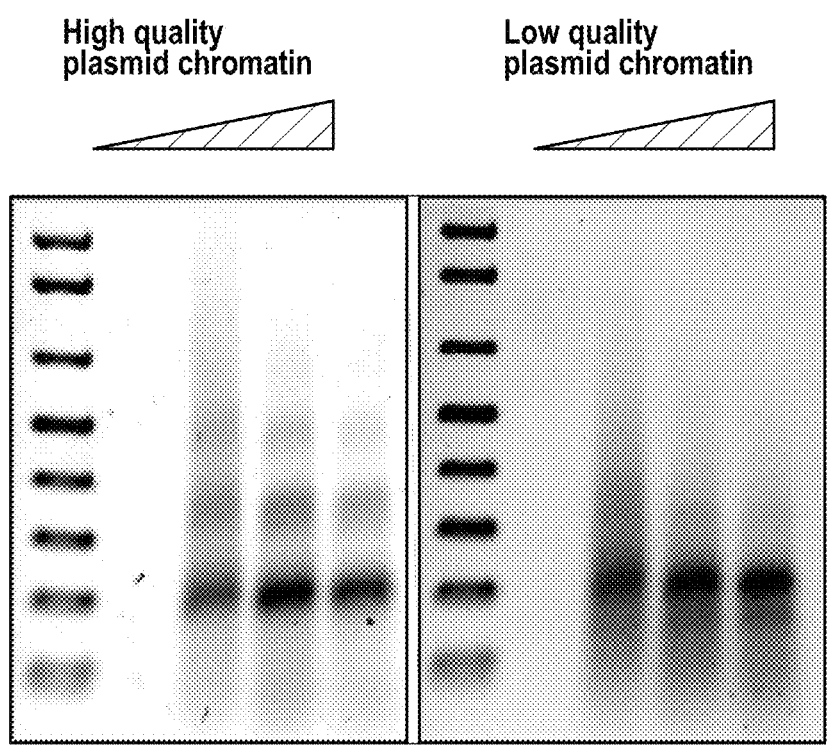

FIG. 12 Visualization of high and low quality plasmid chromatin by analytic nuclease digest and agarose gel electrophoresis. Arrows indicate increasing MNase incubation times. High quality plasmid chromatin is obtained with human recombinant histone octamers as analytic nuclease digest results in a distinct band pattern with only slight sub-nucleosomal DNA. Low quality plasmid chromatin is obtained with human recombinant histone octamers comprising biotinylated H3.3 subunit as analytic nuclease digest does not result in a distinct band pattern with high portion of sub-nucleosomal DNA. Partial and irregular binding of Histones is confirmed by the dominating band at 150-200 bp.

Figure 13:
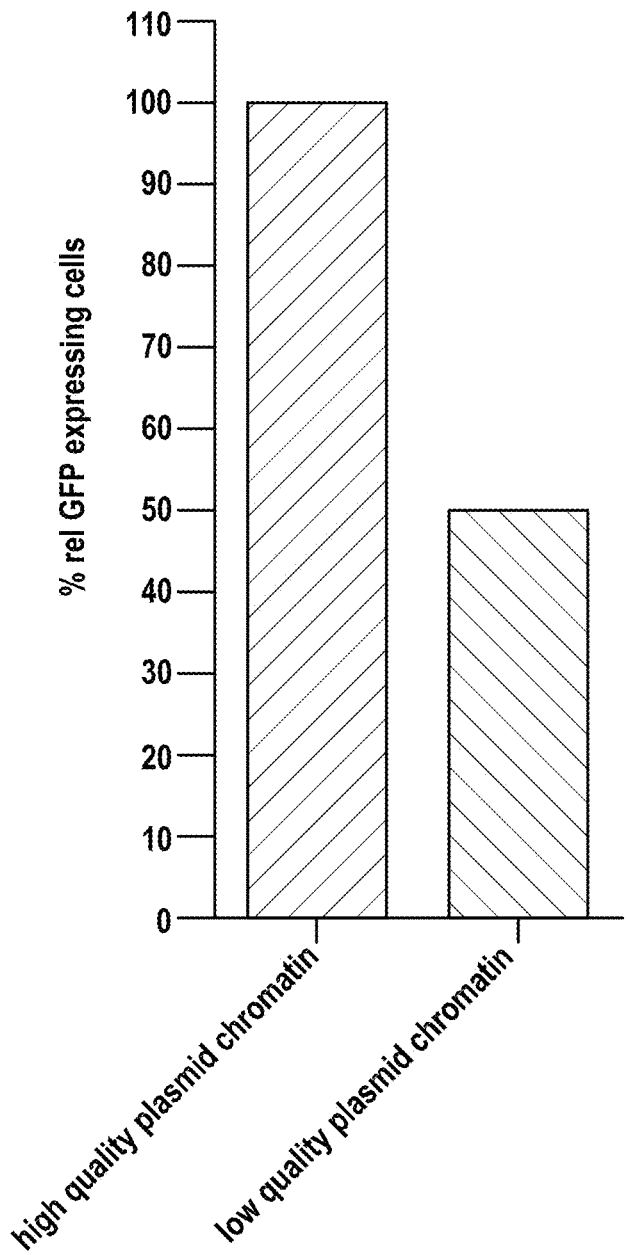

FIG. 13 Chromatin of high and low quality was tested towards delivery efficacy. Low quality chromatin samples showed reduced delivery efficacy, highlighting the importance of proper chromatin assembly on DNA delivery efficacy.

Figure 14:
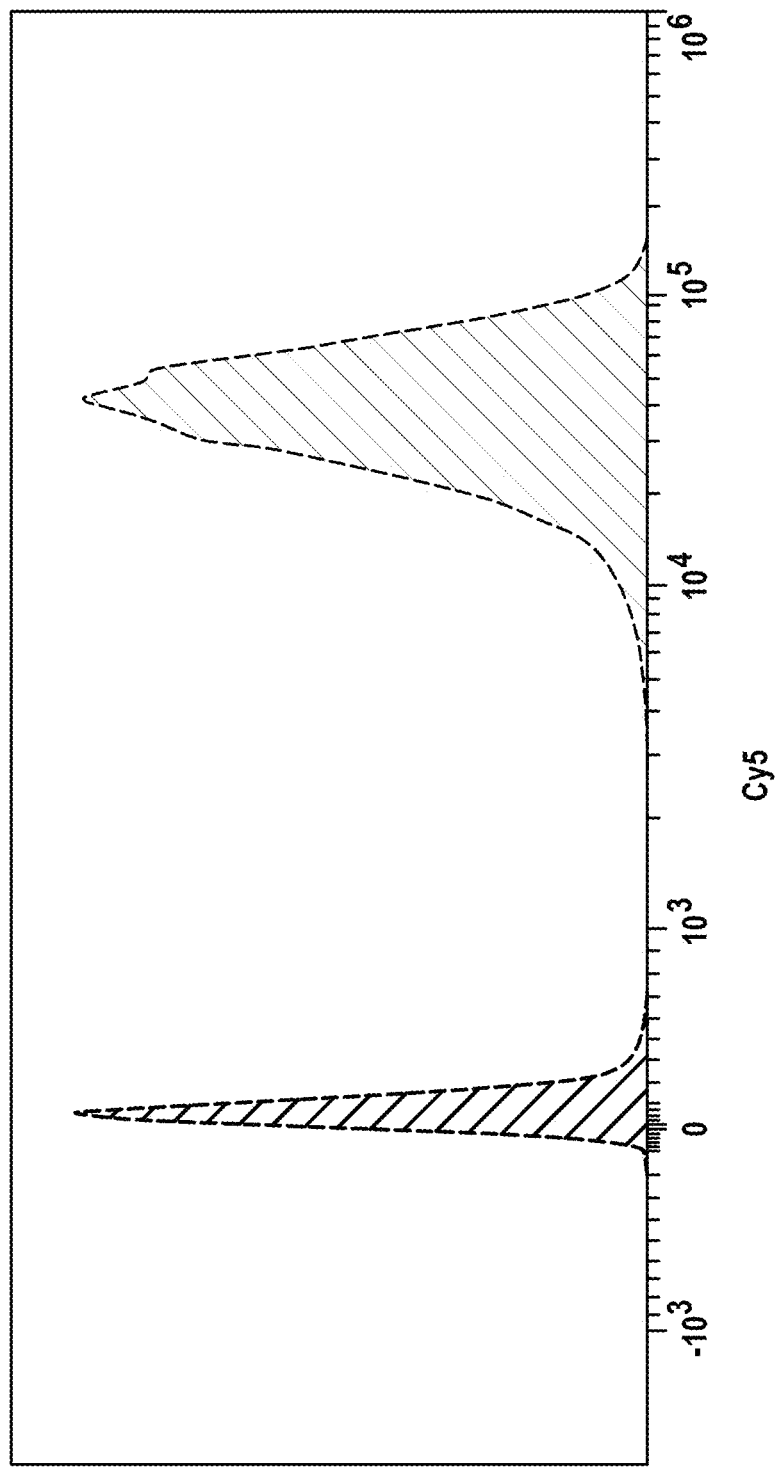

FIG. 14 Flow cytometric determination of delivery specificity; Binding and uptake of antibody-Cy3 and DNA-Cy5 (before and after chromatin assembly) was analyzed by flow cytometry after incubation for 1 h. Histogram of MCF7 cells after treatment with targeted (anti LeY; dotted red) and untargeted (anti CD33; dotted blue) DNA-Cy5 complexes. Cy5 signal was detected only after treatment with the targeted DNA-Cy5 construct.

Figure 15:
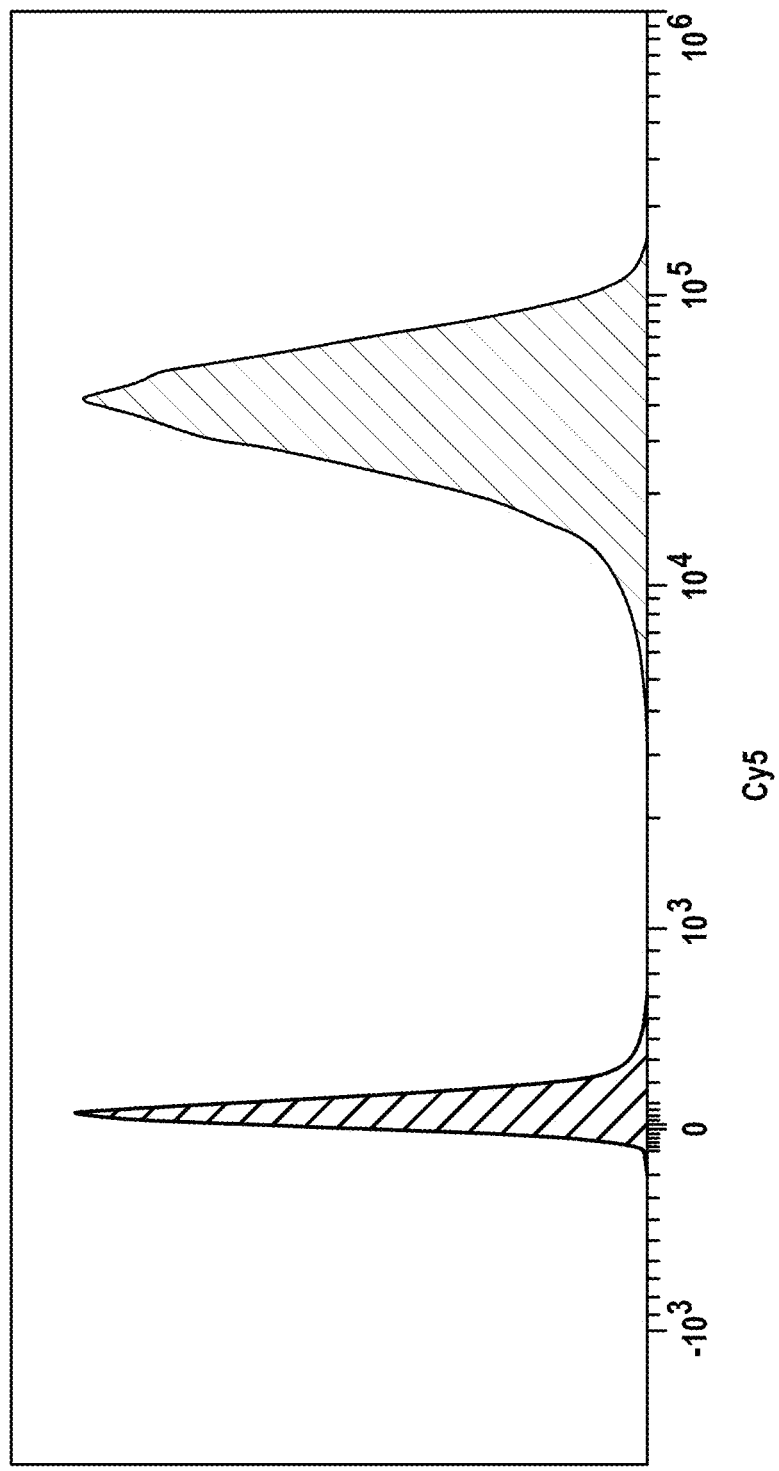

FIG. 15 Flow cytometric determination of delivery specificity; Binding and uptake of antibody-Cy3 and DNA-Cy5 (before and after chromatin assembly) was analyzed by flow cytometry after incubation for 1 h. Histogram of MCF7 cells after treatment with targeted (red) and untargeted (blue) chromatin-Cy5 complexes. Results are comparable to results after DNA-Cy5 delivery.

Figure 16:
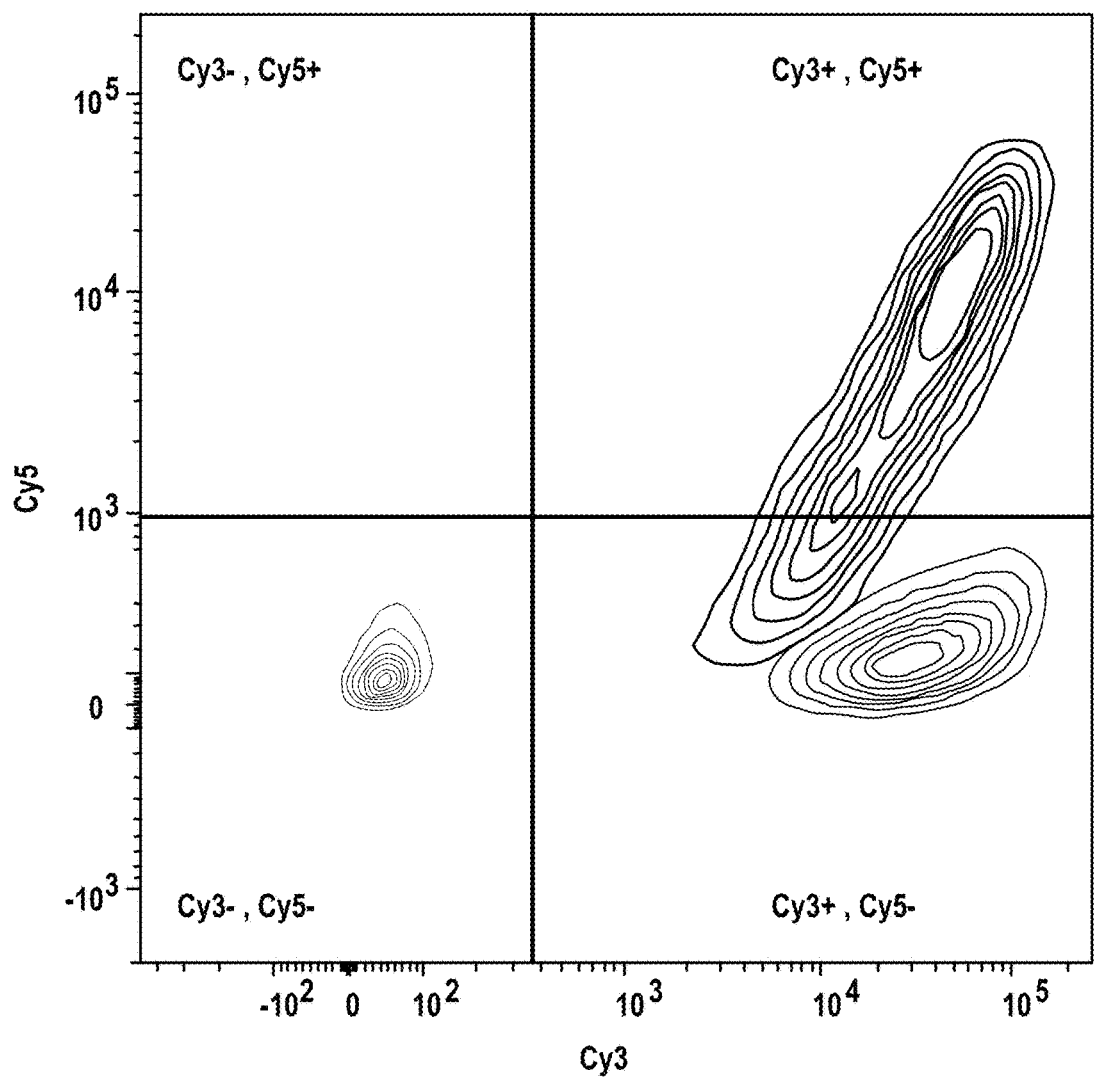

FIG. 16 Flow cytometric determination of delivery specificity; Binding and uptake of antibody-Cy3 and DNA-Cy5 (before and after chromatin assembly) was analyzed by flow cytometry after incubation for 1 h. Contours plot of MCF7 Cy3 (x-axis) and Cy5 (y-axis) signals after treatment with various antibody chromatin complexes comprising Cy3 labelled antibody and Cy5 labelled DNA. Cells were treated with complexes comprising antibody without specificity against cell surface antigen but against CPXM2 peptide do not show Cy3 as well as Cy5 signal (blue). Cells treated with complexes comprising antibody with specificity against the cell surface but not against bio-CPXM2 (anti digoxigenin instead of anti-biotin bsAb) display Cy3 signal but no Cy5 signal, demonstrating that antibody but not chromatin is present at the cell surface (green). Cells treated with complexes comprising antibody with specificity against the cell surface and CPXM2 display Cy3 signal and Cy5 signal, demonstrating that antibody as well as chromatin is present at the cell surface (red).

EXAMPLES

Example 1

Assembly of Plasmid DNA with Histones to Generate Plasmid-Chromatin

Assembly of histones and DNA can be achieved efficiently by in vitro salt gradient dialysis in various scales.

A reaction mixture was prepared with 150-400 µg/mL plasmid DNA in 300 µL 200 ng/mL BSA (Sigma) 1-fold low salt buffer (10 mM Tris-HCl pH 7.6, 50 mM NaCl, 1 mM EDTA, 0.05% w/v Igepal CA630), 2 M NaCl and different amount of histone octamer (calf thymus: 2 µg histone per µg pEGFP plasmid DNA or Cas9 DPH1 gRNA plasmid DNA; human recombinant histones: 0.8-1 µg histone per µg pEGFP plasmid DNA; chicken erythrocyte histones: 1 µg histone per µg pEGFP plasmid DNA). The reaction mixture was transferred into 3.5 kDa MWCO mini dialysis devices (Thermo Fisher Scientific) equilibrated for 15 min. in high salt buffer (10 mM Tris-HCl pH 7.6, 2 M NaCl, 1 mM EDTA, 0.05% w/v Igepal CA630). Afterwards a 4 L beaker was prepared with 300 mL high salt buffer containing 1 mM beta-mercaptoethanol and a second beaker with 3 L 1-fold low salt buffer containing 1 mM beta-mercaptoethanol. The floater and a magnetic stir bar were added into the beaker with high salt buffer. The salt gradient dialysis was performed over night at 4° C. Therefore, the beaker was placed on a magnetic stirrer to allow slow mixing and a peristaltic pump was set to transfer the 3 L of low salt buffer into the beaker containing high salt buffer with a velocity of about 300 mL/h. After buffer dilution, samples were transferred into protein low bind tubes (Eppendorf) and the volume was determined by pipetting.

The plasmids used for chromatin assembly comprised the following elements:
  pEGFP-AmpR (3967 bp):—eGFP expression cassette (CMV promoter;
    eGFP coding sequence; SV40 PolyA)
    F1 origin of replication
    ampicillin resistance gene
  Cas9 DPH1 gRNA (8033 bp):—hU6 Promoter
    transcript template for DPH1 gRNA
    CMV promoter for Cas9 transcription initiation
    Cas9 coding sequence including Myc-Tag and Flag-Tag
    pBR322 origin of replication
    ampicillin resistance gene Example 2

Evaluation of Charge-Resistance of Assembled Plasmid Chromatin Using EMSA

Overall charge of chromatin was analyzed by EMSA shift assay using 500 ng of DNA before and after histone assembly loaded on a 1% ethidium bromide agarose gel with shifts performed at 180 V for 45 min.

Example 3

Evaluation of Nuclease-Resistance of Assembled Plasmid Chromatin

For nuclease sensitivity assays, 2 µg of DNA assembled with chromatin was diluted in buffer (10 mM Tris-HCl, pH 7.6, 80 mM KCl, 10% v/v glycerol, 1.5 mM MgCl$_2$, 1 mM DTT) and 1 µL BSA to a final volume of 50 4. To stop the reaction, 1.5 mL tubes were prepared with 4 µL stop-buffer (100 mM EDTA, 4% w/v sodium dodecyl sulfate). The nuclease digestion was started by addition of 50 µL MNase mix (6 mM CaCl$_2$, 200 µg/4 BSA and 40 U MNase). After the indicated time-points, 30 µL of the reaction mix were transferred to the tubes containing stop-buffer. The DNA was de-proteinized by addition of 1 µL Proteinase K and incubation for 1 h at 50° C. The DNA was purified by ethanol precipitation and analyzed by agarose gel-electrophoresis.

Example 4

Generation of Haptenylated Plasmid-Chromatin

To couple haptens to plasmid-chromatin, chromatin was purified after assembly of histones with an eGFP encoding plasmid (see Example 1 for details) by size exclusion chromatography. Subsequently biotin was attached to lysine side chains of assembled histone octamers by chemical conjugation of NHS-biotin reagents. Therefore, after purification, 100 µg DNA assembled to chromatin was subjected to reactions of the Biotin-XX Microscale Protein Labeling Kit (Thermo Fisher Scientific) according manufacturer's instructions. After biotinylation, free unreacted biotinylation reagent was removed by 7 kDa MWCO Zeba spin desalting columns (Thermo Fischer Scientific). Attachment of biotin to the chromatin was subsequently assessed by determining binding of the resulting conjugates to streptavidin using the ForteBio Octet system using Streptavidin coated dips. For Octet analysis, biotin conjugated plasmid-chromatin (Bio-Chromatin) was diluted to a final concentration of 8 µg/mL in 210 µL PBST buffer. Analyses thereafter were performed under constant shaking at 1000 rpm at 30° C. FIG. 3A shows that after the chemical conjugation reaction plasmid-chromatin binds to streptavidin (Octet analyses). This proves that biotin has been attached to the plasmid-chromatin.

An alternative method to couple biotin to plasmid-chromatin is the chemical conjugation of biotin to plasmid-DNA (applying the Label IT® Nucleic Acid Labeling kit, Mirus, according to the manufacturer's specification) prior to performing the nucleosome/chromatin assembly described in Example 1. FIG. 3B shows that this procedure also results in biotinylated plasmid-chromatin, as represented by its capability to bind streptavidin.

Finally, commercially available biotinylated histones (Active Motif)) can be applied in chromatin assembly reactions as described in Example 1 to generate biotinylated plasmid-chromatin (FIG. 3C).

Example 5

Binding of Haptenylated Peptides Derived from Human Proteins to Plasmid DNA

Interaction of peptides with plasmid DNA was analyzed by EMSA shift assay and/or by Microscale thermophoresis analyses (MST).

For EMSA, 500 ng of DNA was incubated with various amounts of peptide for 30 min. DNA samples with or without peptides were loaded on an ethidium bromide containing 1% agarose gel. EMSA shift was performed at 180 V for 45 min. and analyzed by a gel imager under UV-light (BioRad).

MST measures the movement of plasmid DNA after application of a temperature gradient. This movement is altered, if a ligand (e.g. peptide) binds to the plasmid DNA molecule. So if the movement is altered in the presence of peptide, interaction between peptide and DNA occurs. MST was performed by 2bind GmbH (Regensburg) with peptide concentrations of 5 µM and 10 µM, detecting increase of fluorescence upon incubation with DNA as readout for binding of peptide to DNA.

The results of these analyses are shown in FIG. 4A (EMSA shift assay) and FIG. 4B (MST). Both technologies differentiate peptides that bind DNA from those that do not. The results of these experiments (summarized in the table below) indicate that several human peptides bind plasmid DNA and hence can be used to attach haptens to plasmid DNA. These include peptides derived from human P53, NRTN, FALL, CPXM2, WNT, ASM3B and derivatives thereof.

| Peptide Name | DNA binding | known CPP functionality |
|---|---|---|
| P53 | +++ | ? |
| WNT | + | − |
| NRTN | + | +++ |
| FALL | +++ | ++ |
| CPXM2 | +++ | ++ |
| HisFALL | − | ? |
| TAT | + | + |
| ASM3B | + | ++ |
| HisFALL-NRTN | + | ? |

Example 6

Intracellular Delivery & Functionality of bsAb-Targeted Peptide-Plasmid Assemblies This has been shown by exposing LeY-expressing MCF7 breast cancer cells to bsAbs that simultaneously bind the LeY antigen and digoxigenin, complexed with plasmids that were digoxigenylated by attachment of dig-peptides (dig-NRTN). As a control for specific targeting, plasmids were complexed in separate experiments to dig-binding bsAbs that recognize the CD33 antigen which is absent on MCF7 cells.

Intracellular uptake and functionality was shown by detecting expression of GFP, which is encoded on an expression cassette within the delivered plasmid, inside the MCF7 cells.

The delivery complexes were generated by incubating the GFP expression plasmids in PBS for 1 h with digoxigenin labeled NRTN-peptide and bispecific LeY-Dig bsAb. Thereafter the complexes were added to MCF7 cells seeded in a 96-well plate to a final concentration of 4 µg/mL plasmid DNA, 10 µM peptide and 300 nM antibody. This was followed 48 hrs. later by fluorescence microscope imaging of the treated cells. The results of these analyses are shown in FIG. 8. Imaging fluorescence microscopy revealed complete absence of fluorescence in cell populations treated with non-targeting CD33-bsAb-plasmid complexes. In contrast, cells that expressed GFP were detectable in the LeY+++/CD33-MCF7 cells that received with the cell surface targeting LeY-bsAb-plasmid complexes. Treatment with the complex containing the antibody against the cell surface antigen LeY showed unambiguously single GFP expressing cells (~2% of the population, left panel) while cells treated with the complex containing the antibody against CD33 (right panel) did not show any GFP expression above background. Thus, bsAb-targeted specific delivery and accumulation of haptenylated peptide-DNA complexes enables productive uptake into the cytoplasm/nucleus of cells leading to GFP expression to some extent.

Example 7

Intracellular Delivery & Functionality of bsAb-Targeted Peptide-Chromatin Assemblies
eGFP Fluorescence To show intracellular delivery & functionality of bsAb-targeted peptide-chromatin assemblies LeY-expressing MCF7 breast cancer cells were exposed to bsAbs that simultaneously bind the LeY antigen and digoxigenin or biotin, complexed with digoxigenylated or biotinylated peptides (e.g. Dig-CPXM2, Dig-p53 and Dig-Wntp53 or Bio-CPXM2). As a control for specific targeting, plasmid chromatin was complexed in separate experiments to dig or bio-binding bsAbs that recognize the CD33 antigen, which is absent on MCF7 cells.

Intracellular uptake and functionality was shown by detecting expression of GFP, which is encoded on an expression cassette within the delivered plasmid, inside the MCF7 cells.

The delivery complexes were generated by incubating the GFP expression plasmids in PBS for at least one hour with dig/bio labeled peptide (e.g. Dig-CPXM2 or Bio-CPXM2) and bispecific LeY-Dig/Bio bsAb or bispecific CD33-Dig/Bio bsAb as control antibody. Thereafter the complexes were added to MCF7 cells seeded in a 12-well plate (80,000 cells/well) to a maximal final concentration of 8 μg/mL plasmid DNA assembled to chromatin, 500 nM peptide and 250 nM antibody. This was followed 48 hrs. later by quantification of fluorescent cells by flow cytometry with FACSCanto II (BD Biosciences).

CRISPR/Cas:

Likewise, the targeted delivery of plasmids encoding a CRISPR/Cas9 knock-out system to the cell nucleus has been analyzed to show intracellular delivery and activity of large nucleic acids by the composition as reported herein.

Therefore, the chromatin assembly reaction was performed as described above with a CRISPR/Cas9 encoding plasmid against the DPH1 gene instead of the eGFP plasmid. It has previously been described that gene-editing mediated inactivation of DPH1, combined with assessment of cellular sensitivity towards Diphtheria Toxin (DT), can be used to quantify efficacy of gene editing (see, e.g., WO 2018/060238; Killian, T. et al., Sci. Rep. 7 (2017) 15480). Inactivation of all cellular copies of DPH1 (as consequence of gene editing) in turn renders cells resistant to DT. This generates a very robust readout, which can be quantified by counting DT-resistant colonies following gene editing.

The complexes were added to MCF7 cells seeded in a 12-well plate (2,000 cells/well) to a maximal final concentration of 8 μg/mL plasmid DNA assembled to chromatin, 500 nM peptide and 250 nM antibody. Seventy-two hours after treatment, medium was removed and cells were exposed to medium containing DT at a final concentration of 2 nM. DT exposure was continued for two weeks with medium exchange every 3 to 4 days. After this period, cells were stained with methylene blue and efficiency of intracellular delivery and expression of the editing components was assessed by determination of DT-resistant colonies as previously described by Killian et al. (Killian, T. et al., Sci. Rep. 7 (2017) 15480; WO 2018/060238). The results are shown in FIG. 11.

Example 8

Intracellular Routing and Functionality of Targeted Plasmid DNA or Chromatin Monitored by Confocal Microscopy

To enable fluorescence microscopic analysis of plasmid DNA and plasmid chromatin targeting and routing, Cy5 fluorescent dye was chemically conjugated to plasmid-DNA applying the Label IT® Nucleic Acid Labeling kit, Mirus, according to the manufacturer's specification. To generate fluorescent plasmid chromatin, chromatin assembly was performed with Cy5 labeled plasmid as described in Example 1.

For live cell imaging, MCF7 cells (NCI) were cultured in phenol red-free RPMI medium supplemented with 10% fetal calf serum (FCS) and 100 U/ml penicillin and 100 μg/ml streptomycin. 20,000 cells/well were seeded into 8-well chamber slides (Lab-Tek™, Thermo Fisher Scientific, Braunschweig, Germany) and allowed to adhere overnight. Glass surfaces had been coated with 30 μg/ml fibronectin in PBS for one hour at 37° C. Antibody plasmid DNA-Cy5 and antibody-plasmid chromatin-Cy5 complexes were formed as described in Example 7. Samples were added to MCF7 at a final concentration of 4 μg/mL plasmid DNA, 250 nM peptide and 125 nM antibody. 1 h, 4 h, 24 h and 48 h after addition, internalization of antibody-chromatin complexes and GFP expression were followed by live cell fluorescence microscopy carried out on a Leica SP5 laser scanning confocal microscope using a 63×/1.2 NA water immersion objective lens (Leica, Mannheim, Germany). Temperature, $CO_2$ level and humidity were maintained at 37° C. and 5% $CO_2$ using a stage-top incubation chamber (Oko-touch, Okolab, Ottaviano, Italy). Sequential scans were performed using white light laser excitation at 488 nm (561 nm) and 633 nm. Fluorescence emission was detected at 495-548 nm (GFP), 570-628 nm (Cy3) and 647-732 nm (Cy5) using HyD detectors. Images were processed with ImageJ (NIH, Bethesda, MD, USA).

The invention claimed is:

1. A composition for the targeted delivery of large nucleic acids to the nucleus of a eukaryotic cell comprising
one or more histone polypeptides, wherein the one or more histones comprise a polypeptide according to an amino acid sequence selected from the group consisting of SEQ ID NOs: 01-13,
a large nucleic acid comprising between 1,000 and 100,000 nucleotides or base pairs,
a hapten, wherein the hapten is selected from biotin, digoxygenin, and theophylline and
a bispecific binder comprising a polypeptide according to an amino acid sequence selected from the group consisting of SEQ ID NOs: 15-38 and that has a first binding site specifically binding to the hapten and a second binding site specifically binding to a cell-surface target present on the eukaryotic cell,
wherein
the histone and/or the nucleic acid is conjugated to the hapten,
the histone and the large nucleic acid form a nucleosome,
the hapten and the bispecific binder are bound to each other by the first binding site of the bispecific binder, and
the histone, hapten, and bispecific binder are not conjugated to a virus.

2. The composition according to claim 1, wherein the one or more histone polypeptides are a mixture of histone H2A, H2B, H3 and H4.

3. The composition according to claim 1, wherein the one or more histone polypeptides are a mixture of histone H2A and histone H3.

4. The composition according to claim 1, wherein the histone polypeptides are calf thymus histone polypeptides.

5. The composition according to claim 1, wherein the histone polypeptides are recombinant human histone 3.1 or 3.3.

6. The composition according to claim 1, wherein the large nucleic acid is a plasmid and comprises between 1,500 and 10,000 base pairs.

7. The composition according to claim 1, wherein the composition comprises one hapten molecule.

8. The composition according to claim 1, wherein the hapten is chemically conjugated to the histone or large nucleic acid.

9. The composition according to claim 1, wherein the hapten is conjugated to a DNA binding peptide which is attached to the large nucleic acid.

10. The composition according to claim 1, wherein the bispecific binder is a bispecific antibody.

11. The composition according to claim 1, wherein the composition comprises one or more molecules of the bispecific binder.

12. The composition according to claim 1, wherein the large nucleic acid comprises:
CRISPR/Cas-system nucleic acids, and/or
an expression cassette for a polypeptide endogenous to the mammalian cell, and/or
an expression cassette for polypeptides that encodes enzymes or other proteins/peptides with therapeutic function, and/or
a transcription system for non-coding RNA with therapeutic function like micro RNA, short interfering RNA, long non-coding RNA, RNA decoys, RNA aptamers and ribozymes.

\* \* \* \* \*